United States Patent
Creswell et al.

(10) Patent No.: US 6,472,418 B1
(45) Date of Patent: Oct. 29, 2002

(54) NON-PEPTIDE NK$_1$ RECEPTORS ANTAGONISTS

(75) Inventors: Mark Wallace Creswell, Chelsea, MI (US); Michael Higginbottom, Cambridgeshire (GB); David Christopher Horwell, Cambridge (GB); Russel Andrew Lewthwaite, Cambridge (GB); Martyn Clive Pritchard, Cambrigeshire (GB); Jennifer Raphy, Herts (GB)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/868,449

(22) PCT Filed: Dec. 14, 1999

(86) PCT No.: PCT/US99/29592

§ 371 (c)(1),
(2), (4) Date: Jun. 18, 2001

(87) PCT Pub. No.: WO00/37462

PCT Pub. Date: Jun. 29, 2000

Related U.S. Application Data
(60) Provisional application No. 60/112,725, filed on Dec. 18, 1998.

(51) Int. Cl.$^7$ ................... A61K 31/404; C07D 209/40; C07D 209/42
(52) U.S. Cl. ................... 514/422; 548/467; 548/490; 548/494
(58) Field of Search ................... 548/452, 454, 548/469, 490, 494; 514/414, 415, 419, 422

(56) References Cited

U.S. PATENT DOCUMENTS

| | | |
|---|---|---|
| 5,594,022 A | 1/1997 | Horwell et al. ............. 514/419 |
| 5,716,979 A | 2/1998 | Horwell et al. ............. 514/415 |

FOREIGN PATENT DOCUMENTS

| | | |
|---|---|---|
| EP | 0443132 | 8/1991 |
| WO | 9514017 | 5/1995 |
| WO | 9533744 | 12/1995 |
| WO | 9807718 | 2/1998 |
| WO | 9952903 | 10/1999 |

OTHER PUBLICATIONS

English Abstract Caplus DN 101: 7615, El–Naggar et al., "Synthesis Of 2–furyl . . . " 1983 vol. 26(1) pp. 75–81.*
English Abstract Caplus DN 131:110809, Atherton James P et al "Sample pooling to enhance . . . " 1999 vol. 20(1–2) pp. 39–47.*
PCT International Search Report, PCT/US99/29592.
Qi et al., "L–Trptophan Urea Amides as NK1/NK2 Dual Antagonists", *Bioorganic & Medicinal Chemistry Letters*, vol. 8, 1998, pp. 2259–2262.
Horwell et al., "Quantitative Structure–Activity Relationships (QSARs) of N–Terminus Fragments of NK1 Tachykinin Antagonists: A Comparison of Classical QSARs and Three–Dimensionas QSARs from Similarity Matrices", *J. Med. Chem.*, vol. 38, No. 22, 1995, pp. 4454–4462.
Goldstein et al., "Bioactive conformations of peptides and mimetics as milestones in drug design: Investigation of NK1 receptor antagonists", *Letters in Peptide Science*, vol. 2, 1995, pp. 125–134.

* cited by examiner

*Primary Examiner*—Alan L. Rotman
*Assistant Examiner*—Rita Desai
(74) *Attorney, Agent, or Firm*—David R. Kurlandsky; Charles W. Ashbrook

(57) ABSTRACT

Non-peptide acetamide derivatives of Formula I are specific NK$_1$ antagonist,

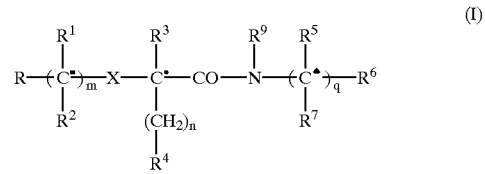

where R is aryl, R$^1$ and R$^2$ are H or alkyl, m, n and q are integers from 0 to 4, X is NR$^8$ or NHCONH, R$^3$ and R$^9$ are H or alkyl, R$^4$ is naphthyl or indolyl, R$^5$ and R$^2$ are H or alkyl, and R$^6$ is aryl.

The compounds are useful agents for treating inflammatory and allergic disorders, pain, anxiety, depression, schizophrenia and emesis.

18 Claims, No Drawings

NON-PEPTIDE NK$_1$ RECEPTORS ANTAGONISTS

This application is a 371 Application of PCT/US99/29592 filed Dec. 14, 1999, which claims the benefit of priority to U.S. Provisional Application Serial No. 60/112,725 filed Dec. 18, 1998.

BACKGROUND OF THE INVENTION

The neurokinins are a family of mammalian neuropeptides that are involved with numerous biological activities such as pain transmission, vasodilation, smooth muscle contraction, bronchoconstriction, activation of the immune system, and neurogenic inflammation. One such neuropeptide known as substance P is widely distributed throughout the peripheral and central nervous system of mammals, and is known to mediate a variety of biological actions via interaction with three neurokinin (NK or tachykinin) receptor types known as NK$_1$, NK$_2$, and NK$_3$.

Substance P binds with higher affinity to the NK$_1$ receptor than it does to the other receptors. Accordingly, compounds capable of antagonizing the effects of substance P at the NK$_1$ receptor are useful for treating and controlling disorders mediated by such interactions, including disorders such as anxiety, pain, depression, schizophrenia, and emesis.

Since 1991, a number of high-affinity nonpeptide tachykinin antagonists have been reported; for a review see Sprecher A, et al (*IDrugs*, 1:73–91, 1998).

U.S. Pat. Nos. 5,594,022 and 5,716,979 describe nonpeptides that are relatively specific NK$_1$ antagonists.

Since substance P mediate various biological actions, including smooth muscle contraction, pain transmission, neuronal excitation, secretion of saliva, angiogenesis, broncho-constriction, activation of the immune system and neurogenic inflammation via an interaction with NK receptors, preferably NK$_1$, thus compounds capable of antagonising the effects of substance P at NK$_1$ receptors will be useful in treating or preventing a variety of: brain disorders including pain (inflammatory, surgical and neuropathic), anxiety, panic, depression, schizophrenia, neuralgia, stress, sexual dysfunction, bipolar disorders, movement disorders, cognitive disorders, obesity and addiction disorders; inflammatory diseases such as arthritis, asthma, bronchitis and psoriasis; gastrointestinal disorders including colitis, Crohn's disease, irritable bowel syndrome, and satiety; allergic responses such as eczema and rhinitis; vascular disorders such as angina and migraine; neuropathological disorders including scleroderma and emesis.

The compounds of the invention, NK$_1$ receptor antagonists, are useful as anti-angiogenic agents for the treatment of conditions associated with aberrant neovascularization such as rheumatoid arthritis, atherosclerosis and tumour cell growth. They will also be useful as agents for imaging NK$_1$ receptors in vivo in conditions such as ulcerative colitis and Crohn's disease.

SUMMARY OF THE INVENTION

This invention provides NK$_1$ receptor antagonists characterized as non-peptide acetamide derivatives. The compounds of the invention differ from those of U.S. Pat. Nos. 5,716,979 or 5,594,022 in that the compounds of Formula I below are not (N-substituted aryl-methyl) carbamates, i.e. they do not have a —O—C(O)—N— link in the backbone; certain final products being more stable than known compounds, they should show improved oral bioavailability and improved CNS penetration. The invention compounds are defined by Formula I:

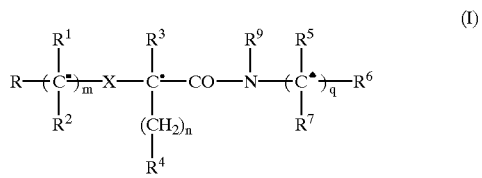

and the pharmaceutically acceptable salts thereof, wherein

■, ●, and ▲ indicate all stereoisomers,

R is:
  pyridyl,
  thienyl,
  furyl,
  pyrrolyl,
  pyrazolyl,
  quinolyl,
  isoquinolyl,
  naphthyl,
  indolyl,
  benzofuryl,
  benzothiophenyl,
  benzimidazolyl, and
  benzoxazolyl, wherein each of the foregoing is unsubstituted, mono-, di- or trisubstituted by alkyl, hydroxy, alkoxy, halogen, —CF$_3$, carboxy, sulfonamide, or nitro;

R can also be:

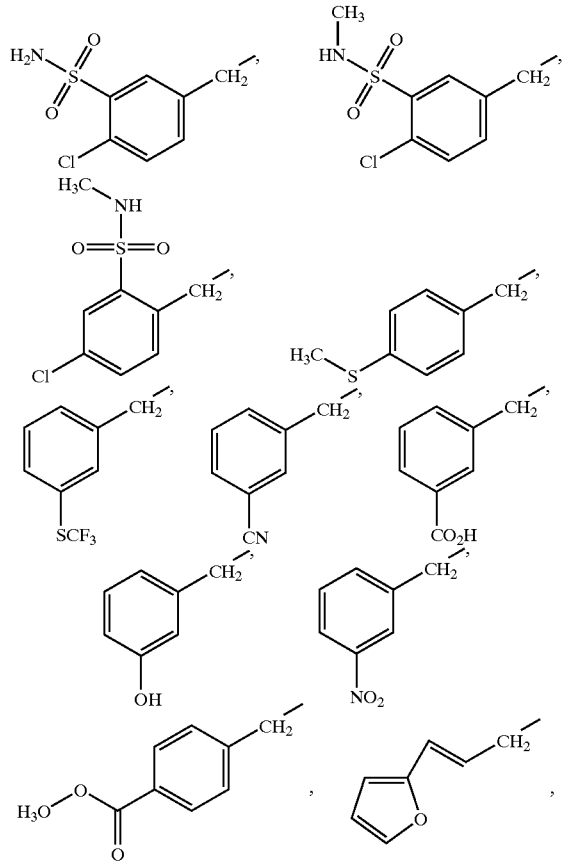

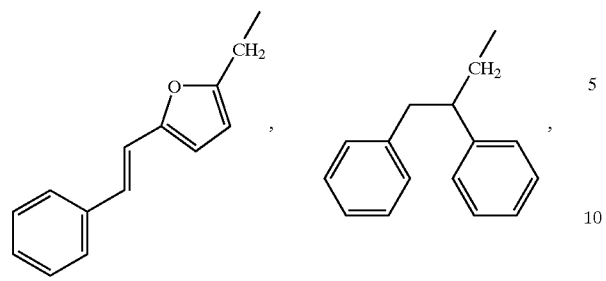
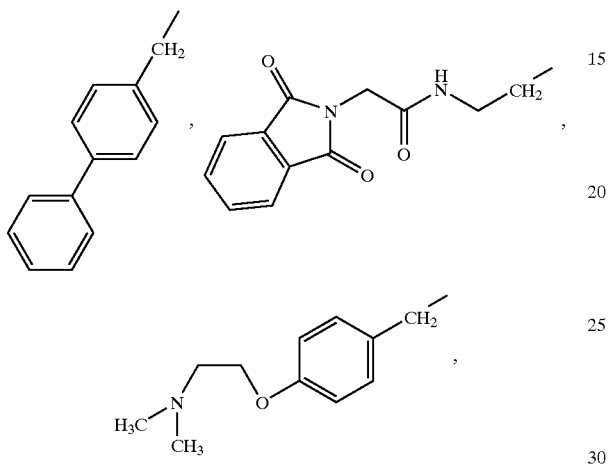
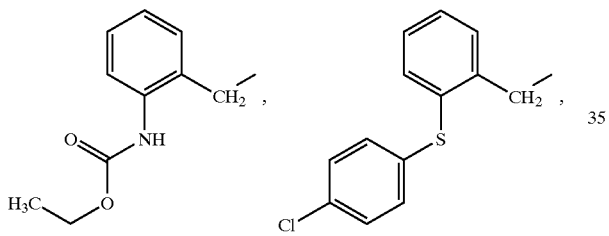
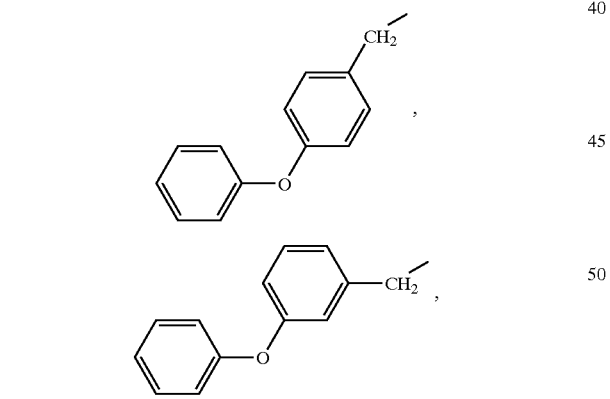
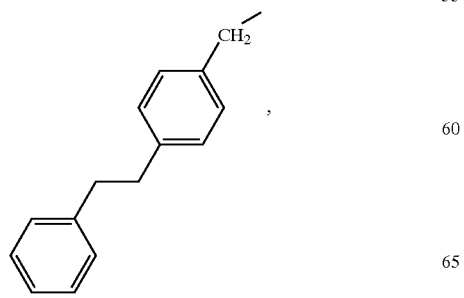
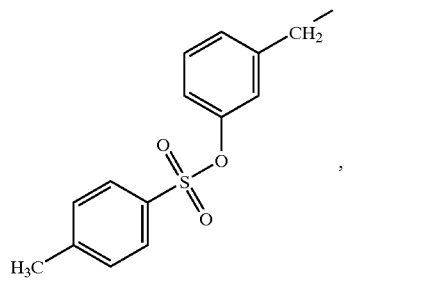
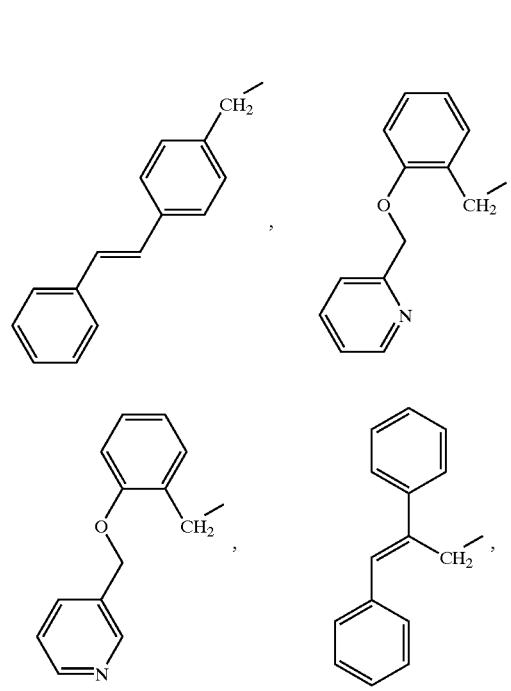

-continued

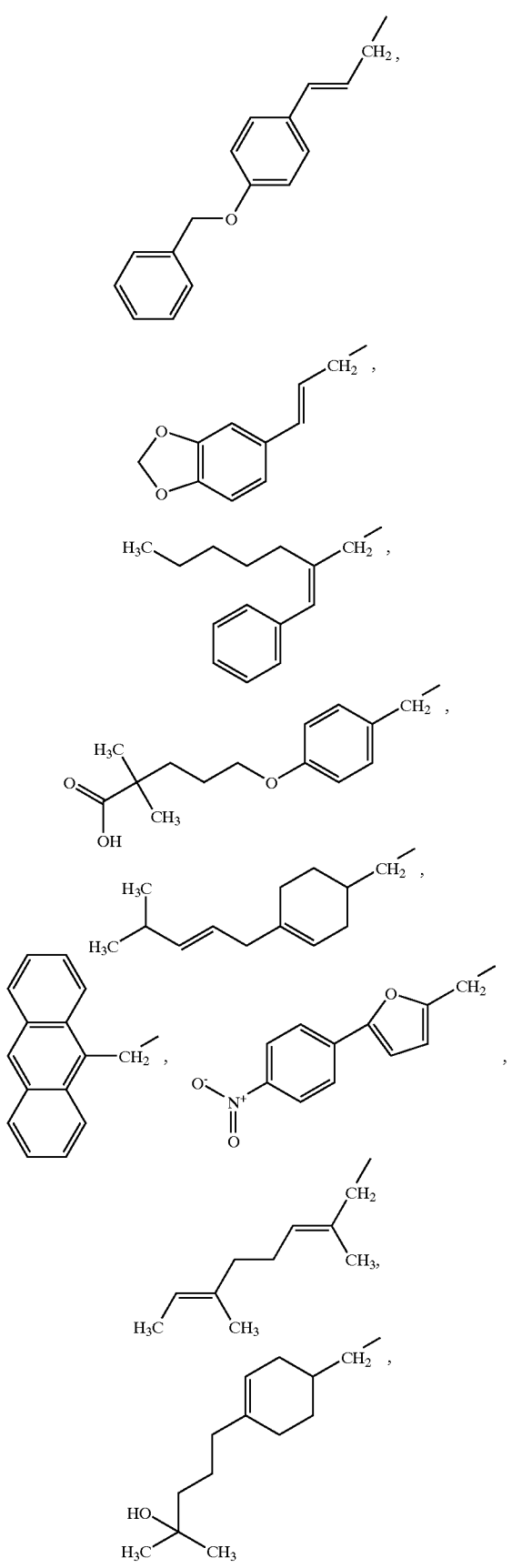

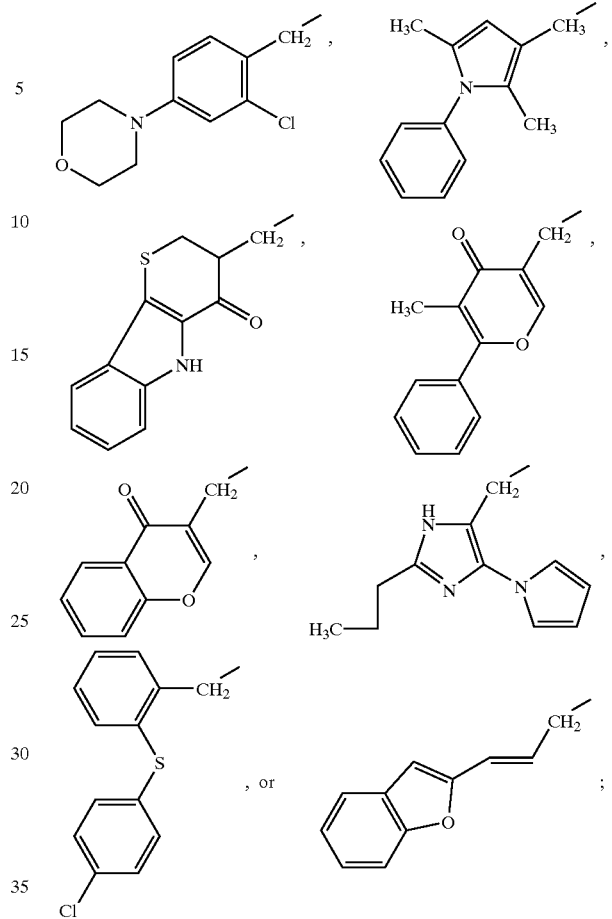

$R_1$ and $R_2$ are each independently H or $C_1$–$C_4$ alkyl;
m is an integer from 0 to 3,
X is NHCONH, or $NR^8$ where $R^8$ is H or $C_1$–$C_4$ alkyl;
$R^3$ is hydrogen or $C_1$–$C_4$ alkyl;
n is an integer from 1 to 2;
$R^4$ is naphthyl or indolyl, wherein said groups are unsubstituted, mono-, di- or trisubstituted by alkyl, hydroxy or formyl;
$R^9$ is hydrogen or $C_1$–$C_4$ alkyl;
$R^5$ and $R^7$ are each independently hydrogen or $(CH_2)_p R^{10}$ where:
  p is an integer of 1 to 3, and
  $R^{10}$ is H, $CH_3$, CN, OH, $OCH_3$, $CO_2CH_3$, $NH_2$, $NHCH_3$, or $N(CH_3)_2$;
q is an integer of 0 to 4;
$R^6$ is phenyl,
  pyridyl,
  thienyl,
  furyl,
  pyrrolyl,
  pyrazolyl,
  imidazolyl,
  quinolyl,
  isoquinolyl,
  naphthyl,
  indolyl,
  benzofuryl,
  benzothiophenyl, benzimidazolyl, or
benzoxazolyl, wherein each of the foregoing is
  unsubstituted, mono-, di- or trisubstituted by
    alkyl,
    hydroxy,
    alkoxy,
    halogen,
    $CF_3$,
    $NO_2$,
    $N(CH_3)_2$,
    $OCF_3$,
    $SONH_2$,
    $NH_2$,
    $CONH_2$,
    $CO_2CH_3$, or
    $CO_2H$,
or $R^6$ is:
  straight alkyl of from 1 to 3 carbons,
  branched alkyl of from 3 to 8 carbons,
  cycloalkyl of from 5 to 8 carbons or
  heterocycloalkyl,
    each of which can be substituted with up to one or two
      substituents selected from
      OH,
      $CO_2H$,
      $N(CH_3)_2$,
      $NHCH_3$ and
      $CH_3$; and
$R^5$ and $R^6$, when joined by a bond, can form a ring;
$R^6$ is also

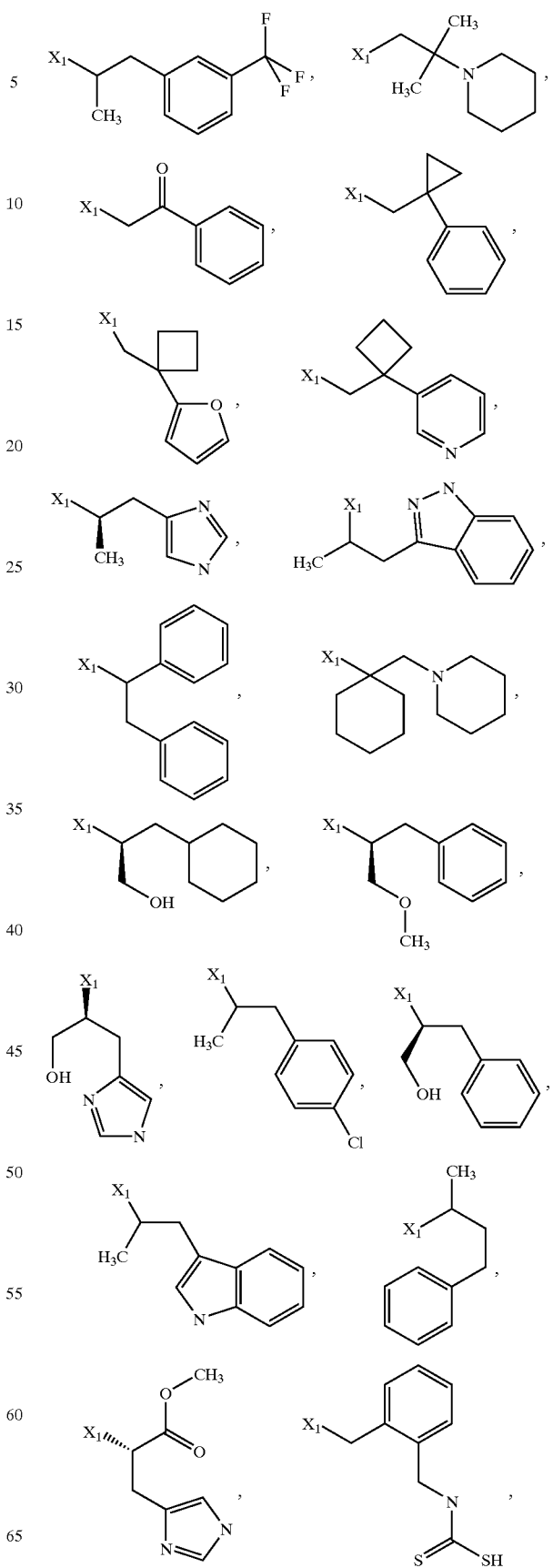

-continued

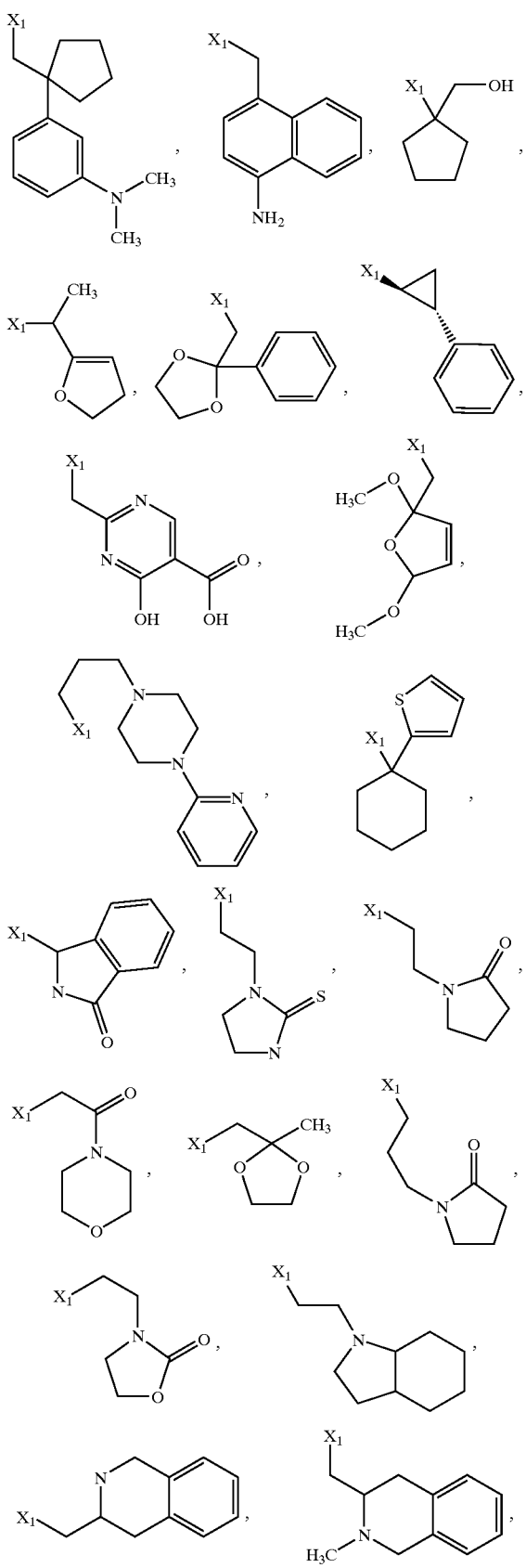

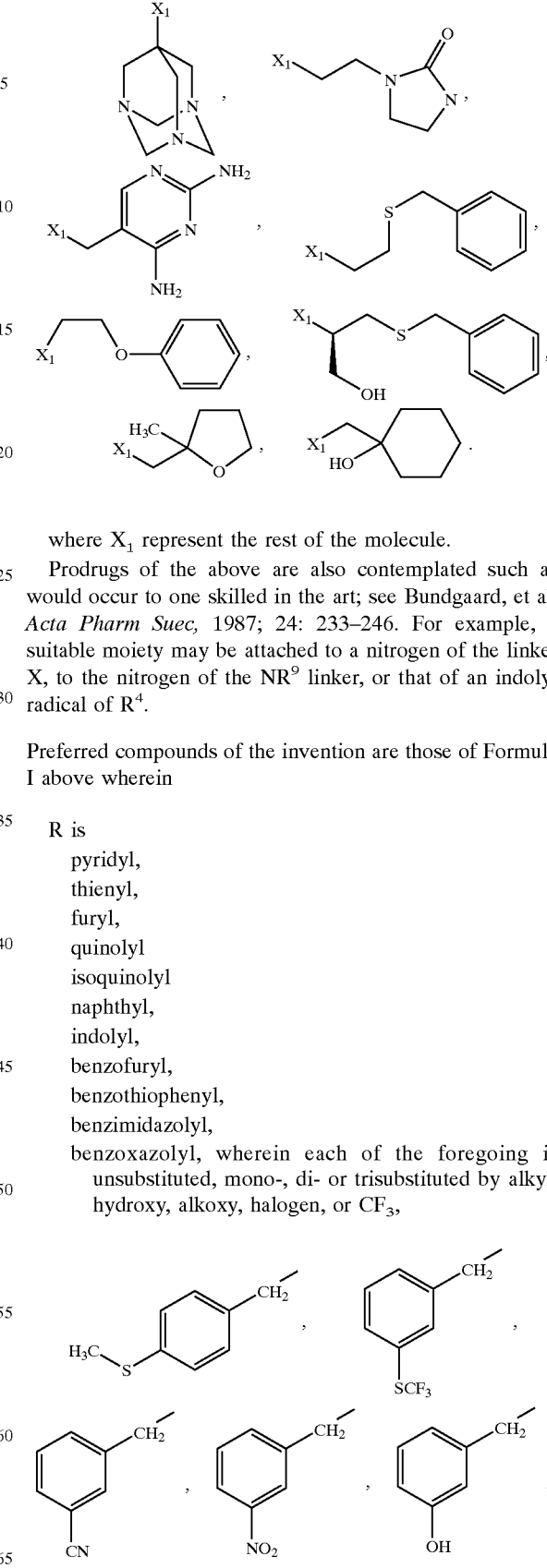

where $X_1$ represent the rest of the molecule.

Prodrugs of the above are also contemplated such as would occur to one skilled in the art; see Bundgaard, et al, *Acta Pharm Suec,* 1987; 24: 233–246. For example, a suitable moiety may be attached to a nitrogen of the linker X, to the nitrogen of the $NR^9$ linker, or that of an indolyl radical of $R^4$.

Preferred compounds of the invention are those of Formula I above wherein

R is
  pyridyl,
  thienyl,
  furyl,
  quinolyl
  isoquinolyl
  naphthyl,
  indolyl,
  benzofuryl,
  benzothiophenyl,
  benzimidazolyl,
  benzoxazolyl, wherein each of the foregoing is unsubstituted, mono-, di- or trisubstituted by alkyl, hydroxy, alkoxy, halogen, or $CF_3$, -continued m is an integer from 1 to 3;
R⁶ is
  phenyl
  pyridyl,
  thienyl,
  furyl,
  pyrrolyl,
  quinolyl,
  isoquinolyl,
  naphthyl,
  indolyl,
  benzofuryl,
  benzothiophenyl,
  benzimidazolyl, or
  benzoxazolyl,
    wherein each of the foregoing is unsubstituted, mono-, di- or trisubstituted by
      alkyl,
      hydroxy,
      alkoxy,
      halogen,
      $CF_3$,
      $NO_2$
      $N(CH_3)_2$,
      $OCF_3$,
      $SONH_2$,
      $NH_2$,
      $CONH_2$,
      $CO_2CH_3$, or
      $CO_2H$,
  cycloalkyl of from 5 to 6 carbons or heterocycloalkyl, with up to one or two substituents selected from OH,
    $CO_2H$,
    $N(CH_3)_2$,
    $NHCH_3$ and
    $CH_3$; and
  $R^5$ and $R^6$ when joined by a bond can form a ring.
More preferred compounds of the invention are those of Formula I above wherein
  R is
    pyridyl,
    thienyl,
    furyl,
    quinolyl,
    naphthyl,
    benzofuryl,
    benzothiophenyl,
    benzimidazolyl, or
    benzoxazolyl, where each of the foregoing is unsubstituted, mono-, di- or trisubstituted by alkyl, hydroxy, alkoxy, halogen, or —$CF_3$, $R^1$ and $R^2$ are each H;
m is an integer from 1 to 3;
X is $NR^8$ or NHCONH, where $R^8$ is H or methyl;
$R^9$ is hydrogen or alkyl of 1 to 3 carbon atoms;
$R^6$ is
  phenyl,
  pyridyl,
  thienyl,
  furyl,
  pyrrolyl,
  benzimidazolyl, where each of the foregoing is unsubstituted, mono-, di- or trisubstituted by
    alkyl,
    hydroxy,
    alkoxy,
    halogen,
    $CF_3$,
    $NO_2$,
    $N(CH_3)_2$;
cyclohexyl or heterocycloalkyl, with up to one or two substituents selected from OH,
CO₂H,
N(CH₃)₂,
NHCH₃ and
CH₃; and
R⁵ and R⁶, when joined by a bond, can form a ring.

The most preferred compounds of the invention have Formula II:

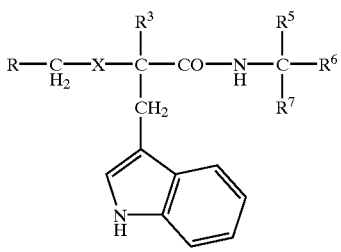

(II)

wherein:
R is
  benzofuryl,
  benzoxazolyl,
  3-cyanophenyl,
  3-nitrophenyl, or
  3-trifluoromethylphenyl;
R³ is hydrogen or methyl;
X is NH or NHCONH;
R⁵ and R⁷ independently are hydrogen or CH₂R¹⁰, where R¹⁰ is H, CH₃ or OH;
R⁶ is
  phenyl,
  substituted phenyl,
  pyridyl, or,
  cyclohexyl;
and the pharmaceutically acceptable salts thereof.

Most preferred compounds of the invention are:
2-[(Benzofuran-2-ylmethyl)-amino]-3-(1H-indol-3-yl)-2-methyl-N-(1-phenyl-ethyl)-propionamide, [R-(R*,S*)]
2-[(Benzofuran-2-ylmethyl)-amino]-3-(1H-indol-3-yl)-2-methyl-N-(1-pyridin-4-yl-ethyl)-propionamide, [R-(R*,S*)]
2-[(Benzofuran-2-ylmethyl)-amino]-3-(1H-indol-3-yl)-2-methyl-N-[1-(4-nitro-phenyl)-ethyl]-propionamide, [R-(R*,R*)]
2-[(Benzofuran-2-ylmethyl)-amino]-N-(2-hydroxy-1-phenyl-ethyl)-3-(1H-indol-3-yl)-2-methyl-propionamide, [R-(R*,R*)]
[R-(R*,S*)]2-[(Benzofuran-2-ylmethyl)-amino]-N-(1-cyclohexyl-ethyl)-3-(1H-indol-3-yl)-2-methyl-propionamide
[R-(R*,S*)]2-[(Benzofuran-2-ylmethyl)-amino]-3-(1H-indol-3-yl)-2-methyl-N-(1-p-tolyl-ethyl)-propionamide
2-[(Benzofuran-2-ylmethyl)-amino]-3-(1H-indol-3-yl)-N-(1-p-tolyl-ethyl)-propionamide, [R-(R*,S*)]
2-(3-Cyano-benzylamino)-3-(1H-indol-3-yl)-N-(1-phenyl-ethyl)-propionamide, [R-(R*,S*)]
3-(1H-Indol-3-yl)-2-(3-nitro-benzylamino)-N-(1-phenyl-ethyl)-propionamide, [R-(R*,S*)]
3-(1H-Indol-3-yl)-N-(1-phenyl-ethyl)-2-(3-trifluoromethoxy-benzylamino)-propionamide, [R-(R*,S*)]
2-[(Benzofuran-2-ylmethyl)-amino]-3-(1H-indol-3-yl)-N-(1-pyridin-4-yl-ethyl)-propionamide, [R-(R*,S*)]
2-[(Benzofuran-2-ylmethyl)-amino]-3-(1H-indol-3-yl)-N-(1-phenyl-ethyl)-propionamide, [R-(R*,S*)]
2-[(Benzoxazol-2-ylmethyl)-amino]-3-(1H-indol-3-yl)-N-(1-phenyl-ethyl)-propionamide
2-(2-Benzofaran-2-yl-ethylamino)-3-(1H-indol-3-yl)-N-(1-phenyl-ethyl)-propionamide, [R-(R*,S*)], and
2-(3-Benzofuran-2-ylmethyl-ureido)-3-(1H-indol-3-yl)-2-methyl-N-(1-phenyl-ethyl)-propionamide, [R-(R*,S*)].

The invention additionally provides pharmaceutical formulations comprising a compound of Formula I admixed with a pharmaceutically acceptable carrier, diluent or excipient therefor. Especially preferred formulations comprise a compound of Formula II. The invention also provides a method for antagonizing NK₁ receptors in a mammal comprising administering to a mammal an NK₁ binding amount of a compound of Formula I. The invention further provides a method for treating a CNS disorder including pain, anxiety, depression, obesity, or schizophrenia; an allergic or inflammatory disease; a gastrointestinal disorder; a vascular disorder; or a neuropathological disorder including emesis; comprising administering to a mammal in need of treatment an effective amount of a compound of Formula I. An especially preferred method of treatment utilizes a compound of Formula II.

DETAILED DESCRIPTION OF THE INVENTION

Throughout this application, the following abbreviations have the meanings listed below:
Boc tertiary butyloxycarbonyl
DCE dichloroethane
DCM dichloromethane
HBTU O-Benzotriazol-1-yl-N,N,N',N'-tetramethyluronium hexafluorophosphate
DIPEA N,N-diisopropylethylamine
DMF N,N-dimethylformamide
DCC 1,3-dicyclohexylcarbodiimide
EEDQ 2-ethoxy-1-ethoxycarbonyl-1,2-dihydroquinoline
EtOAc ethyl acetate
EtOH ethanol
MeOH methanol
KOH potassium hydroxide
DIBAL Diisobutylaluminium hydride
NMM N-methyl-morpholine
NMR nuclear magnetic resonance
Trp Tryptophan The term "alkyl" means a straight or branched hydrocarbon having from one to 12 carbon atoms and includes, for example, methyl, ethyl, n-propyl, isopropyl, n-butyl, sec-butyl, tert-butyl, n-pentyl, n-hexyl, n-heptyl, n-octyl, undecyl, dodecyl, and the like unless stated specifically otherwise.

The term "cycloalkyl" means a saturated hydrocarbon ring which contains from 3 to 12 carbon atoms, for example cyclopropyl, cyclobutyl, cyclopentyl, cyclohexyl except as otherwise stated.

The term "alkoxy" means an alkyl as described above attached through an oxygen atom.

The term "halogen" is chlorine, bromine, fluorine or iodine.

The ring formed by joining R⁵ and R⁶ is from 4 to 6 atoms total and is unsubstituted.

The compounds of Formula I are capable of forming pharmaceutically acceptable acid addition salts. All of these forms are within the scope of the present invention.

Pharmaceutically acceptable acid addition salts of the compound of Formula I include salts derived from inorganic acids such as hydrochloric, nitric, phosphoric, sulfuric, hydrobromic, hydroiodic, hydrofluoric, phosphorous, and the like as well as the salts derived from nontoxic organic acids, such as the aliphatic mono- and dicarboxylic acids, phenyl-substituted alkanoic acids, hydroxy-alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, trifluoroacetate, propionate, caprylate, isobutyrate, oxalate, malonate, succinate, suberate, sebacate, fumarate, maleate, mandalate, benzoate, chlorobenzoate, methylbenzoate, dinitrobenzoate, phthalate, benzenesulfonate, toluenesulfonate, phenylacetate, citrate, lactate, tartrate, methanesulfonate, and the like. Also contemplated are salts of amino acids such as arginate and the like. For example, see Berge S. M., et al., Pharmaceutical Salts, *J. Pharm. Sci.*, 66:1–19 (1977) incorporated herein by reference.

The acid addition salts of the compounds of Formula I are prepared by contacting the free base form of the compound with a sufficient amount of the desired acid to produce the salt in the conventional manner. Preferably, a compound of Formula I can be converted to an acidic salt by treating an aqueous solution of the desired acid, such that the resulting pH is less than four. The solution can be passed through a C18 cartridge to absorb the compound, washed with copious amounts of water, the compound eluted with a polar organic solvent such as, for example methanol, acetonitrile, aqueous mixtures thereof, and the like, and isolated by concentrating under reduced pressure followed by lyophilisation. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for the purpose of the present invention.

Certain of the compounds of the present invention can exist in unsolvated forms as well as solvated forms, including hydrated forms. In general, the solvated forms, including hydrated forms are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of the present invention can be prepared and administered in a wide variety of oral and parenteral dosage forms. Thus, the compounds of the present invention can be administered by injection, that is intravenously, intramuscularly, intracutaneously, subcutaneously, intraduodenally, or intraperitoneally. In addition, the compounds of the present invention can be administered by inhalation, for example intranasally. Additionally, the compounds of the present invention can be administered transdermally. It will be obvious to those skilled in the art that the following dosage forms may comprise as the active component, either a compound of Formula I or a corresponding pharmaceutically acceptable salt of the compound of Formula I.

For preparing pharmaceutical compositions from the compounds of the present invention, pharmaceutically acceptable carriers can be either solid or liquid. Solid form preparations include powders, pills, tablets, capsules, cachets, suppositories and dispersible granules. A solid carrier can be one or more substances that may also act as diluents, flavouring agents, binders, preservatives, tablet disintegrating agents, or an encapsulating material.

In powders, the carrier is a finely divided solid that is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax such as a mixture of fatty acid glycerides or cocoa butter, is first melted and the active component is dispersed homogeneously therein, as by stirring. The molten homogeneous mixture is then poured into convenient sized moulds, allowed to cool, and thereby to solidify.

Liquid form preparations include solutions, suspensions and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavours, stabilizing and thickening agents as desired.

Aqueous suspensions suitable for oral use can be made by dispersing the finely divided active component in water with viscous material, such as natural or synthetic gums, resins, methylcellulose sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilising agents and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet or lozenge itself, or it can be the appropriate number of any of these in packaged form.

The quantity of active component in a unit dose preparation may be varied or adjusted from 0.1 mg to 200 mg, preferably 0.5 mg to 100 mg according to the particular application and the potency of the active component. The composition can, if desired, also contain other compatible therapeutic agents.

In therapeutic use, the highly selective and competitive antagonists of the $NK_1$ receptor and compounds utilized in the pharmaceutical method of this invention are administered at the initial dosage of about 0.01 mg/kg to about 500 mg/kg daily. A daily dose range of about 0.01 mg/kg to about 100 mg/kg is preferred. The dosages, however, may be varied depending upon the requirements of the patient, the severity of the condition being treated and the compound being employed. Determination of the proper dosage for a particular situation is within the skill of the art. Generally, treatment is initiated with smaller doses, which are less than the optimum dose of the compound. Thereafter, the dosage is increased by small increments until the optimum effect under the circumstances is reached. For convenience, the total daily dosage may be divided and administered in portions during the day, if desired.

The compounds of Formula I can be prepared by any several synthetic processes well known to those skilled in the art of organic chemistry.

In a typical synthesis, a carboxylic acid of the formula

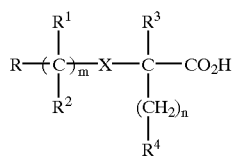

is coupled to an amine of the formula

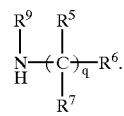

The coupling can be achieved by routine acylation, e.g. by converting the acid to an acid halide, followed by reaction with the amine, or by utilizing a common coupling reagent such as 1,3-dicyclohexylcarbodiimide (DCC) or 2-ethoxy-1-ethoxycarbonyl-1,2-dihydroquinoline (EEDQ). The synthesis can be carried out on racemic reactants, to provide invention compounds in racemic form, which can then be resolved by conventional methods, if desired. Alternatively, the invention compounds can be prepared in optically active form by using enantiomeric reactants.

In a typical synthesis, an optically active acetic acid is first prepared by conventional methods.

Schemes 1–5 illustrate the preparation of intermediates utilized in Examples 1–5, which illustrate the synthesis of specific compounds of Formula I in optically active form.

Scheme 1 describes the synthesis of intermediates I and II, which are required for Examples 1 to 5. The N-terminal benzofuran moiety is introduced by the reductive amination of either tryptophan methyl ester or alpha-methyl-tryptophan methyl ester with benzofuran-2-carboxaldehyde and sodium triacetoxy borohydride in DCM. The methyl ester is then hydrolyzed to the corresponding carboxylic acid with lithium hydroxide.

Scheme 2 describes the synthesis of intermediate III. 3-Acetyl-1-methyl pyrrole is converted to the corresponding oxime by reaction with hydroxylamine sulfate and potassium hydroxide in water/methanol. The oxime is then reduced on palladium on carbon.

Scheme 3 shows the synthesis of intermediate IV. This compound was prepared from (R)-2-phenylglycinol, which was first N-terminal protected as the carbobenzoxy (CBZ) analogue. The alcohol was then treated with triethylamine and methane sulfonylchloride, followed by dimethylamine to introduce the tertiary amine. Removal of the CBZ protection with hydrogen over Pearlman's catalyst gave the required intermediate.

Scheme 4 describes the synthesis of Examples 1 to 4. Each was prepared by activation of the acid, intermediate I, with HBTU in the presence of DIPEA and then reacting with the required amine in DMF.

The synthesis of Example 5 is outlined in scheme 5. Intermediate I was activated with HBTU in DMF and then coupled with methoxybenzylamine. The methyl ether was then reduced with boron tribromide in DCM.

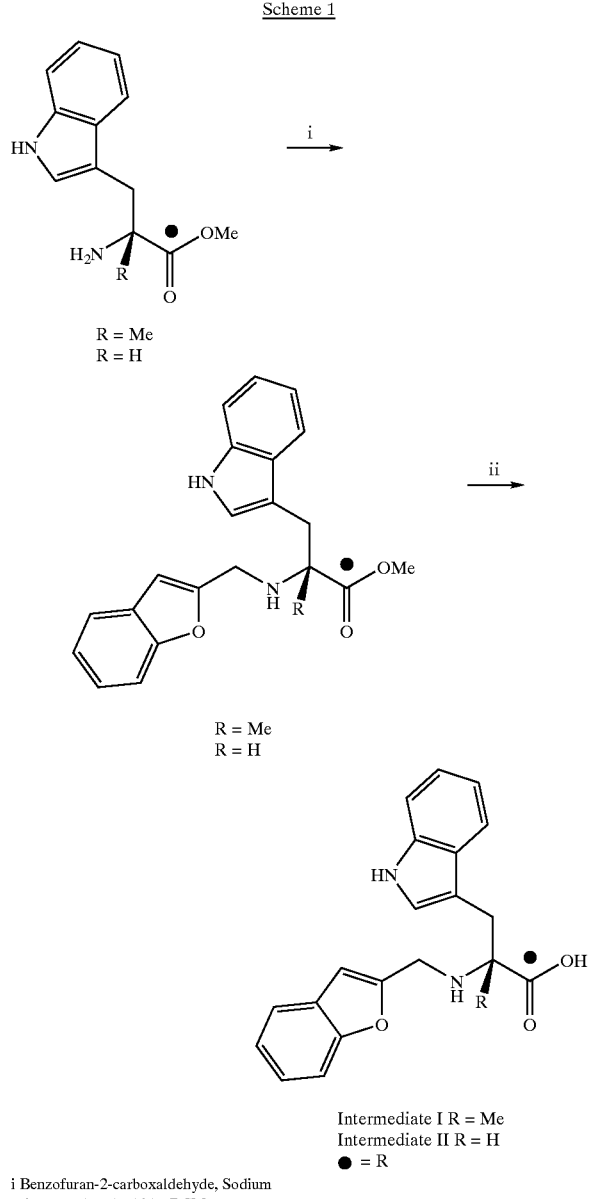

i Benzofuran-2-carboxaldehyde, Sodium triacetoxy borohydride, DCM
ii LiOH, H₂O

Scheme 2
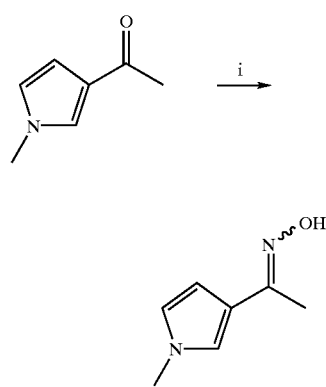
i Hydroxylamine sulphate, KOH, MeOH, H₂O
ii H₂, Pd/C, MeOH
Scheme 3
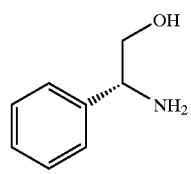
i Benzyl chloroformate, Et₃N, THF
ii CH₃SO₂Cl, Et₃N, THF
iii 2M HNMe₂, in THF
iv H₂, Pearlman's cat., MeOH
Scheme 4
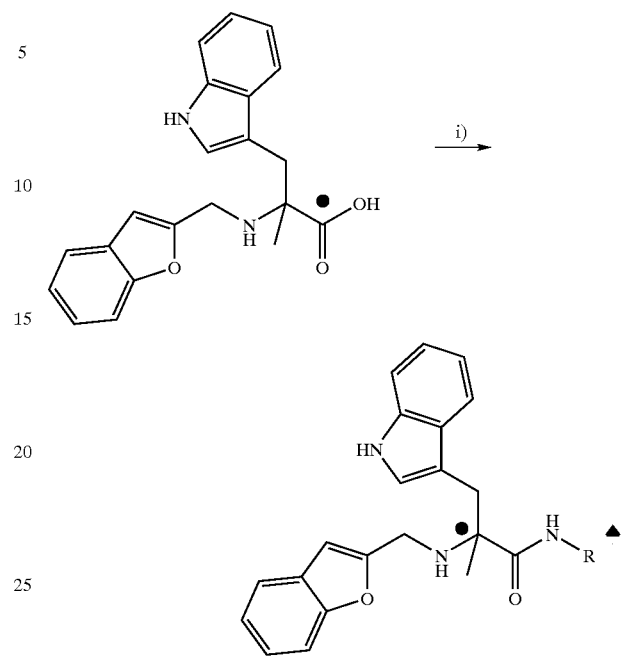
i) amine, HBTU, DIPEA, DMF
| Example number | ● | ▲ | Amine (RNH₂) |
|---|---|---|---|
| 1 | R | - | NH₂C(CH₃)₂Ph |
| 2 | R | RS | Intermediate III |
| 3 | R | S | NH₂CH(CH₃)4-pyridine |
| 4 | R | R | Intermediate IV |
Scheme 5
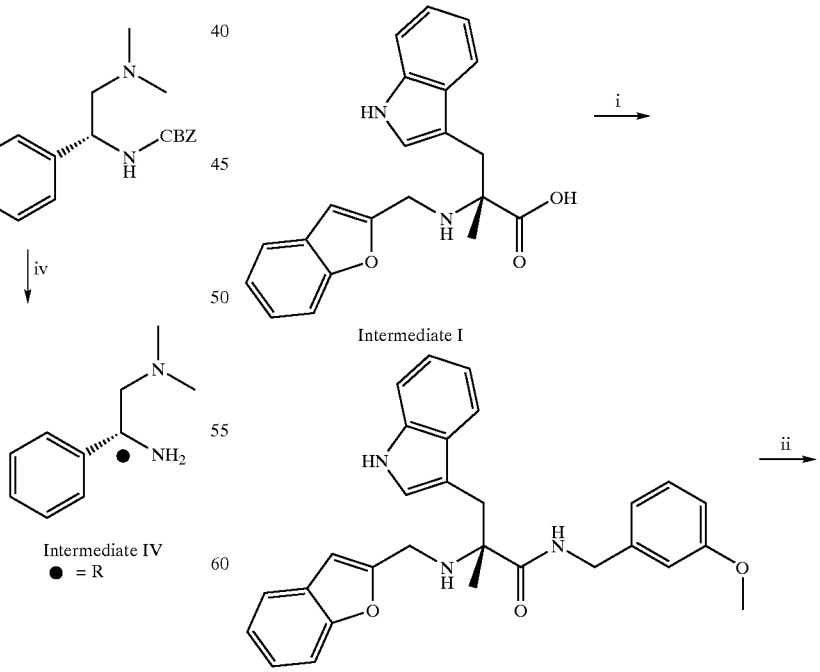

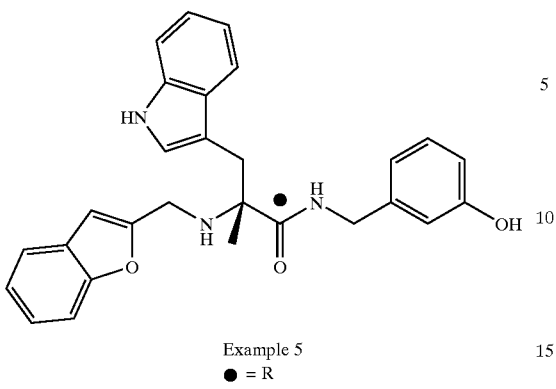

Example 5
● = R
i HBTU, DIPEA, Methoxybenzylamine, DMF
ii BBr$_3$, DCM

EXAMPLE 1

2-[(Benzofuran-2-ylmethyl)-amino]-3-(1H-indol-3-yl)-2-methyl-N-(1-methyl-1-phenyl-ethyl)-propionamide, (R)

Step 1

Alpha methyl tryptophan methyl ester (26.8 g, 0.115 mol) and benzofuran-2-carboxaldehyde (17.57 g, 0.115 mol) were dissolved in DCM (400 mL) under an atmosphere of nitrogen and sodium triacetoxyborohydride (34.12 g, 0.161 mol) was added portionwise over 20 min at 0° C. The mixture was stirred at room temperature for 2 h and then quenched by the addition of sat. NaHCO$_3$ (500 mL). The organic layer was collected and the aqueous layer was extracted three times with EtOAc. The organics were combined, dried (MgSO$_4$), filtered, and evaporated to dryness. The residue was crystallized from ether/heptane to give the product (34.13 g, 82%); IR (film): 3410, 2948, 1724, 1455, 1253, 1104, 742cm$^{-1}$; NMR (CDCl$_3$)δ1.48 (3H, s); 3.18 (1H, d, J=14 Hz); 3.21 (1H, d, J=14 Hz); 3.53 (3H, s); 3.85 (1H, d, J=14 Hz); 3.92 (1H, d, J=14 Hz); 6.55 (1H, s); 7.04–7.59 (9H, m); 8.07 (1H, s); MS; ES+ 363, ES− 361.

Step 2 Intermediate I

The methyl ester from step one (24.94 g, 68.8 mmol) was dissolved in dioxan (800 mL) and aq. LiOH (8.66 g, 206 mmol in 400 mL) was added. The reaction mixture was stirred overnight at room temperature and then heated to 60° C. for 5 h. The mixture was reduced in vacuo to a volume of approximately 200 ml. Water (1200 mL) was added and the reaction was stirred vigorously while it was neutralized with 1N HCl. Ether (1200 mL) was added and the mixture was stirred for two h, the precipitate was filtered off, washed with water, ether and dried to give a white solid; (24.5 g, 100%); NMR (Dmso-d$_6$) 1.28 (3H, s); 3.05 (1H, d, J=14 Hz); 3.07 (1H, d, J=14 Hz); 3.33 (2H, br s); 3.87 (2H, s); 6.72 (1H, s); 6.97–7.07 (3H, m); 7.14 (1H, d, J=2 Hz); 7.18–7.33 (3H, m); 7.50–7.58 (3H, m); 10.89 (1H, s); MS; ES+ 349, ES− 347.

Step 3

Intermediate I (0.348 g, 1 mmol), HBTU (0.379 g, 1 mmol), DIPEA (0.35 mL, 2 mmol) and cumylamine (0.20 g, 1.48 mmol) were stirred in DMF (25 mL) for 18 h. The reaction mixture was evaporated and the residue taken up in EtOAc and washed with 10% Na$_2$CO$_3$, and brine. Drying and purification by column chromatography using 20% EtOAc/Heptane gave a white solid (0.285 g, 61%). mp=57–62° C.; NMR (CDCl$_3$): δ1.40 (3H, s); 1.70 (6H, s); 1.92 (1H, b s); 3.17 and 3.22 (2H 2x d, J=14.4,14.6); 3.82 and 3.89 (2H, 2xd, J=14.6, 14.1); 6.46 (1H, s); 7.02–7.68 (15H, m); 8.10 (1H, s); IR (film): 3317,2987, 1661, 1506, 1455cm$^{-1}$; [α]$_D^{23}$=26.1° (c=1, MeOH); MS(ES$^+$) 466 (M+1); Analysis calculated for C$_{30}$H$_{31}$N$_3$O$_2$. 0.25H$_2$O: C, 76.65; H, 6.75; N, 8.94%. Found: C, 76.73; H, 6.54; N, 8.80%.

EXAMPLE 2

2-[(Benzofuran-2-ylmethyl)-amino]-3-(1H-indol-3-yl)-2-methyl-N-[1-(1-methyl-1H-pyrrol-3-yl)-ethyl]-propionamide, [R-(R*,R*)] and [R-(R*,S*)]

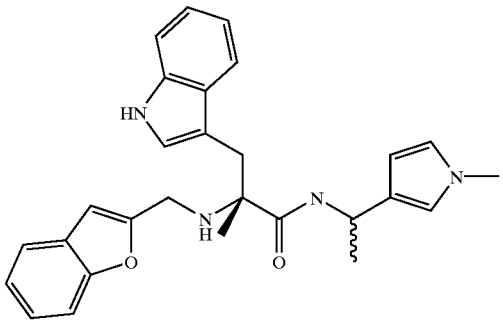

Step 1

3-Acetyl-1-methyl pyrrole (2.00 g, 16.2 mmol) was dissolved in MeOH (60 mL) and treated with potassium hydroxide (4.10 g, 73 mmol) in water (10 mL) and hydroxylamine sulfate (4.00 g, 24.3 mmol) in water (10 mL) and stirred for 18 h. The methanol was removed in vacuo and the residue was diluted with water and extracted with EtOAc. Drying (MgSO$_4$) and evaporation gave an off-white solid (1.82 g, 81%). (E:Z)=9:1); NMR (CDCl$_3$): δ2.17 (3H, s); 3.65 (3H, s); 3.69 (3H, s); 6.39 (1H, m); 6.46 (1H, m); 6.56 (1H, m); 6.58 (1H, m); 7.59 (1H, m); 8.10 (1H, bs); IR(film): 3240, 2916, 1644, 1554,1422, 1257, 892cm$^{-1}$.

Step 2 Intermediate III

The oxime from step one (0.25 g, 1.8 mmol) was dissolved in methanol and 10% Palladium on carbon (50 mg) was added. The mixture was shaken under an atmosphere of hydrogen at 3 psi and at 30° C. for 5 h. Filtering through Kieselguhr and evaporation gave a colorless oil (220 mg) which was a mixture of starting material and product ~1:1. The crude, intermediate III was used in step 3.

Step 3

Intermediate I (0.348 g, 1 mmol), HBTU (0.379 g, 1 mmol), DIPEA (0.35 mL, 2 mmol) and the amine (Intermediate II) (220 mg, 1.8 mmol) were stirred in DMF (13 mL) for 18 h. The reaction mixture was evaporated and the residue taken up in EtOAc and washed with 10%Na$_2$CO$_3$, and brine. Drying and purification by column chromatography using 20% EtOAc/Heptane followed by reverse phase chromatography using 50–100% MeOHMH$_2$O gave a white solid (0.205 g, 45%); mp=53–57° C.; NMR (CDCL$_3$): δ1.35 and 1.43 (3H, 2xd, J=6.6 and 6.6 Hz); 1.45 (obs H$_2$O) and 1.5 (3H, 2xs); 1.89 (1H, bs); 3.21 and 3.22 (2H, 2xs): 3.49 and 3.54 (3H, 2xs); 3.72–3.86 (2H, 2xAB, J=14.4,14.4); 5.05 (1H, m); 6.00 (1H, m); 6.34–7.72 (13H, m); IR (film): 3278, 2969, 1648, 1507, 1455cm$^{-1}$; MS(ES$^+$): 455(M+H) Analysis calculated for C$_{28}$H$_{30}$N$_4$O$_4$; C, 73.98; H, 6.65; N,12.32%. Found: C, 73.69; H, 6.44; N, 12.12%.

EXAMPLE 3

2-[(Benzofuran-2-ylmethyl)-amino]-3-(1H-indol-3-yl)-2-methyl-N-(1-pyridin-4-yl-ethyl)-propionamide, [R(R*,S*)]

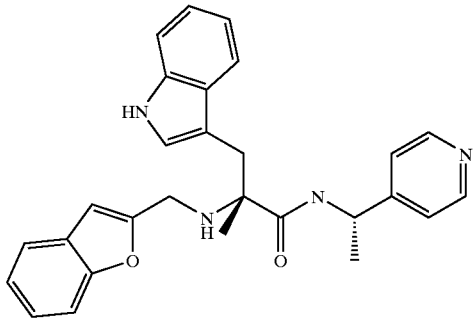

Intermediate I (0.174 g, 0.5 mmol), HBTU (0.190 g, 0.5 mmol), DIPEA (0.348 mL, 2 mmol) and the amine (prepared as described in U.S. Pat. No. 5,594,022) (252 mg, 0.6 mmol) were stirred in DMF (25 mL) for 18 h. The reaction mixture was evaporated and the residue taken up in EtOAc and washed with 10%$Na_2CO_3$, and brine. Drying and purification by column chromatography using 3%MeOH/DCM gave a white solid (0.14 g, 62%). mp=66–69° C.; NMR (CDCl$_3$): δ1.44(3H,d, J=7.2 Hz); 1.50 (3H, s); 1.96 (1H, bs) 3.12 (1H, d, J=14.4 Hz) and 3.23 (1H, s); J=14.4 Hz); 3.80 (1H, d, J=14.2 Hz) and 3.92 (1H, d, J=14.2 Hz); 5.02 (1H, m); 6.48 (1H, s); 6.89–8.00 (12H, m); 8.03 (1H, s); 8.46(2H, m); IR (film) 3326, 2978, 1660, 1602, 1505, 1455 cm$^{-1}$; MS(ES$^+$) 453 (M+1); $[\alpha]_D^{23}$=−29.0° (c=0.39, MeOH); Analysis calculated for $C_{28}H_{28}N_4O_2 \cdot 0.2H_2O$: C, 73.73; H, 6.28; N, 12.28% Found: C, 73.76; H, 6.25; N, 12.08%.

EXAMPLE 4

2-[(Benzofuran-2-ylmethyl)-amino]-N-(2-dimethylamino-1-phenyl-ethyl)-3-(1H-indol-3-yl)-2-methyl-propionamide, (R,R)

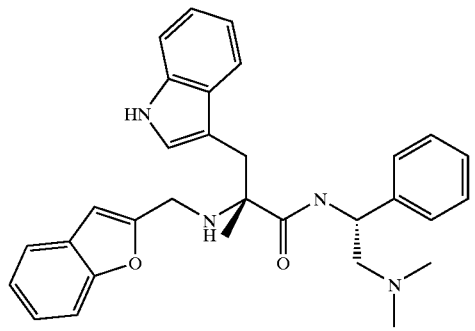

Step 1

To a solution of (R)-2-phenyl glycinol (2.11 g, 15 mmol) and benzyl chloroformate (2.35 mL, 16.5 mmol) in THF (30 mL) at 0° C. was added triethylamine (2.30 mL, 16.5 mmol) in THF (5 mL). After stirring for 18 h at room temperature, the mixture was filtered and evaporated to a white solid which was purified by column chromatography on silica using 50% EtOAc/heptane, giving a white solid (4.00 g, 98%); NMR (CDCl$_3$): δ3.88 (2H, m); 4.85 (1H, m); 5.10 (2H, m); 5.48 (1H, m); 7.23–7.40 (10H, m); IR (film): 3324, 2950, 1687, 1540, 1259cm$^{-1}$;

Step 2

To a solution of the alcohol from step one (1.00 g, 3.68 mmol) and triethylamine (1.16 mL, 8 mmol) in THF (20 mL) was added a solution of methane sulphonylchloride (0.3 mL, 4.0 mmol) in THF (3 mL). The mixture was stirred for 1 h. 2M dimethylamine in THF solution. (17 mL, 34 mmol) was added and the sealed mixture was stirred for 12 days. Evaporation of the solvent and purification by column chromatography using 2% MeOH/DCM gave a yellow oil (0.399 g, 36%); NMR (CDCl$_3$): δ2.23 (6H, s); 2.35–2.58 (2H, m); 4.64 (1H, bs); 5.06 (2H, m); 5.77 (1H, bs); 7.20–7.40 (10H, m); IR (film): 3330, 2945, 1716, 1538, 1246, 1050cm$^{-1}$.

Step 3 Intermediate IV

The protected amine from step one (0.226 g, 0.75 mmol) was dissolved in methanol (30 mL) and Pearlman's catalyst (30 mg) was added. The mixture was shaken for 2 h at 50 psi and then filtered through kieselguhr. Evaporation gave a yellow syrup (0.127 g, 100%); NMR (CDCl$_3$): δ2.22–2.51 (8H, m); 4.07 (1H, m); 7.22–7.39 (5H, m).

Step 4

Intermediate I (0.174 g, 0.5 mmol), HBTU (0.19 g, 0.5 mmol), DIPEA (0.1 74 mL, 1.0 mmol) and the amine (Intermediate IV) (0.12 mg, 0.73 mmol) were stirred in DMF (15 mL) for 18 h. The reaction mixture was evaporated and the residue taken up in EtOAc and washed with 10%$Na_2CO_3$, and brine. Drying and purification by column chromatography using 1% MeOH/DCM and reverse phase chromatography using 40–100% MeOH/$H_2O$ gave a white solid (0.10 g, 40%). mp=130–134° C.; NMR (CDCl$_3$) δ1.44 (3H, s); 2.16 (6H, s); 2.41 (1H, dd, J=5.6, 12.4 Hz) and 2.59 (1H, dd, H=10.0, 12.4); 3.17 (2H, s); 3.86 (1H, d, 14.4 Hz) and 3.92 (1H, d, J=14.6 Hz); 4.95 (1H, m); 6.55 (1H, s); 6.90 (1H, s); 7.09–7.67 (13H, m); 8.01 (1H, s); 8.18, d, J=6.6 Hz); IR (film) 3317, 2934, 1658, 1496, 1455cm$^{-1}$; MS(ES$^+$) 482 (M+1); $[\alpha]_D^{23}$=31.9 (c=0.72, MeOH); Analysis calculated for $C_{31}H_{34}N_4O_2$: C, 75.28; H, 6.93; N, 11.33% Found: C, 75.24; H, 6.92; N, 11.15%.

EXAMPLE 5

2-[(Benzofuran-2-ylmethyl)-amino]-N-(3-hydroxy-benzyl)-3-(1H-indol-3-yl)-2-methyl-propionamide, R

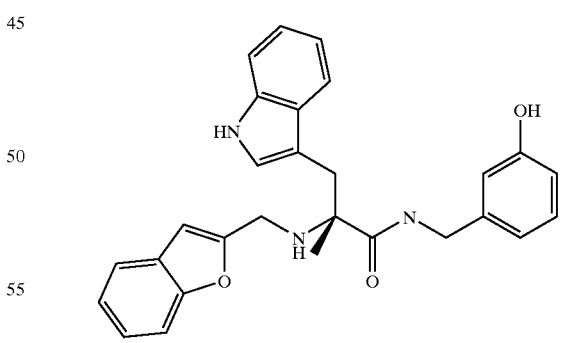

Step 1

Intermediate I (0.348 g, 1 mmol), HBTU (0.379 g, 1 mmol), DIPEA (0.35 mL, 2 mmol) and 3-methoxybenzylamine (0.206 g, 1.5 mmol) were stirred in DMF (17 mL) for 18 h. The reaction mixture was evaporated and the residue taken up in EtOAc and washed with 10%$Na_2CO_3$, and brine. Drying and purification by column chromatography using 40% EtOAc/Heptane gave a white solid (0.190 g; 41%). mp=42–47° C.; NMR (CDCl$_3$): δ1.50

(3H, s); 1.90 (1H, bs); 3.20 (1H, d, J=14.4 Hz) and 3.28 (1H, d, J=14.4 Hz); 3.72–3.82 (4H, m); 3.88 (1H, d, J=14.0 Hz): 4.37 (2H, d, J=6.0 Hz); 6.37 (1H, s); 6.75–7.70 (14H, m); 8.12 (1H, s); IR (film): 3322, 2920, 1654, 1602, 1455, 1256cm$^{-1}$; MS(ES$^+$) 468 (M+1); $[\alpha]_D^{23.5}$=−31.3° (c=1.01, MeOH); Analysis calculated for $C_{29}H_{29}N_3O_3$: C, 74.50; H, 6.25; N, 8.99%; Found: C, 74.20; H, 6.24; N, 8.78%

Step 2

1.0M Boron tribromide in dichloromethane (0.62 mL; 0.62 mmol) was added dropwise to a solution of the methoxy compound from step one (0.146 g; 0.31 mmol) in dichloromethane at −70° C. under $N_2$, warmed slowly to room temperature and stirred for 18 h. The mixture was poured onto 10 g crushed ice/2M HCl (15 mL) and stirred for 10 min. Neutralizing with $Na_2CO_3$, extraction with EtOAc and purification by column chromatography using 40% EtOAc/heptane gave a white solid (0.115 g; 82%). mp=60–69° C.; NMR (CDCl$_3$): δ1.53 (3H, s); 1.96 (1H, bs); 3.14 (1H, d, J=14.4 Hz) and 3.37 (1H, d, J=14.4 Hz); 3.81 (1H, d, J=14.0 Hz) and 3.93 (1H, d, J=14.0 Hz); 4.14–4.50 (2H, m); 5.23 (1H, bs); 6.32–7.82 (15H, m); 8.14 (1H, s); IR (film): 3333, 2907, 1645, 1599, 1520, 1455, 1254cm$^{-1}$; MS(ES$^+$): 454 (M+1); $[\alpha]_D^{23.5}$=−25.9° (c=0.73, MeOH); Analysis calculated for $C_{28}H_{27}N_3O_3$. 0.5H$_2$O: C, 72.71; H, 6.10; N, 9.08% Found: C, 72.83, 72.86; H, 6.03, 5.96; N, 8.81, 8.83%.

Scheme 6 describes the synthesis of intermediate V, which is required for Examples 6 to 17.

Boc-tryptophan was coupled to alpha-methylbenzylamine using HBTU activation. The Boc group was removed using formic acid in DCM to give Intermediate V.

Examples 6, 8 and 10 to 21 were prepared by a reductive amination of the relative aldehydes and Intermediate V with sodium triacetoxyborohydride as shown in scheme 7.

Scheme 8 outlines the synthesis of Example 7. 2-Benzofuranacetic acid was reacted with ethyl chloroformate in THF and then reduced with lithium borohydride. The alcohol was then converted to the corresponding mesylate and reacted with Intermediate V to give Example7.

Scheme 9 describes the synthesis of Example 9. 2-Hydroxymethyl benzimidazole was reacted with bis(4-nitrophenyl) carbonate in DMF to form the cyclic carbamate. This compound was then reacted with intermediate V to give Example 9.1

The synthesis of Intermediate VI is shown in scheme 10; the intermediate was used to prepare Example 10. Benzo[b]thiophene-2-carboxylic acid was activated with ethyl chloroformate and then coupled with N,O-dimethylhydroxylamine. The Weinreb amide was then reduced to the corresponding aldehyde with DIBAL.

The synthesis of Example 22 is described in scheme 11. 2-benzofurancarboxaldehyde was reacted with hydroxylamine in aqueous potassium hydroxide/EtOH. The oxime was then reduced with lithium aluminum hydride to give the amine. The corresponding isocyanate, prepared by reacting the amine with triphosgene in DCM/pyridine, was reacted with 2-amino-3-(1H-indol-3-yl)-2-methyl-N-(1-phenylethyl)-propionamide to give Example 22.

Scheme 12 shows the synthesis of the key intermediate VII that was used in the a synthesis of Examples 192 to 308. This N-carboxyanhydride was prepared by reacting intermediate I with phosgene in toluene.

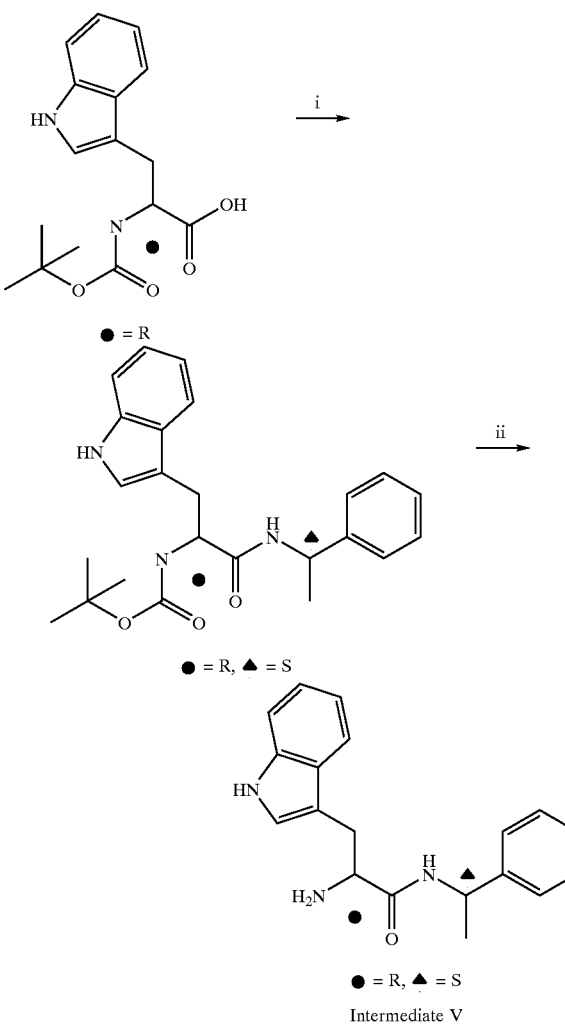

Scheme 6 i. HBTU, DMF, DIPEA, α-methylbenzylamine
ii. Formic acid, DCM

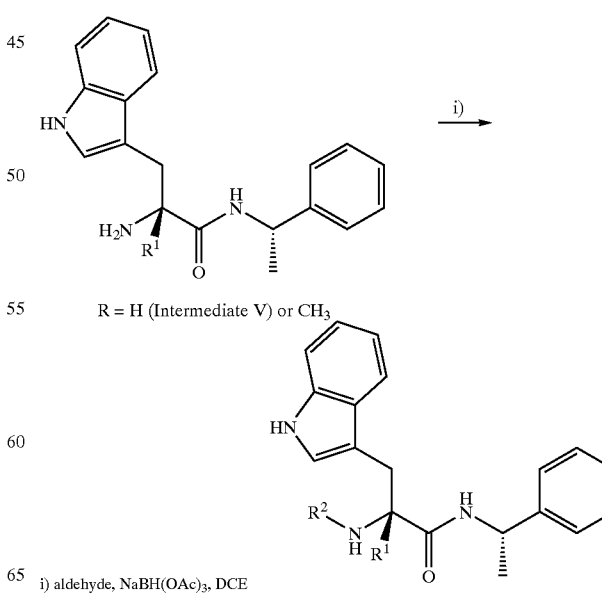

Scheme 7

R = H (Intermediate V) or CH$_3$ i) aldehyde, NaBH(OAc)$_3$, DCE

| Example | R¹ | R² |
|---|---|---|
| 6 | H | 2-Benzofuran-CH₂ |
| 8 | H | 2-(4,5-Dimethylfuran)-CH₂ |
| 10 | H | 2-Benzothiophene-CH₂ |
| 11 | H | 3-quinoline-CH₂ |
| 12 | H | 2-(5-Cl-thiophene)-CH₂ |
| 13 | H | (3-SCF₃—Ph)—CH₂ |
| 14 | H | (3-CN—Ph)—CH₂ |
| 15 | H | (3-NO₂—Ph)—CH₂ |
| 16 | H | (3-OCF₃—Ph)—CH₂ |
| 17 | H | (3-OH—Ph)—CH₂ |
| 18 | CH₃ | 2-Benzofuran-CH₂ |
| 19 | CH₃ | 3-Benzofuran-CH₂ |
| 20 | CH₃ | 2-pyrrole-CH₂ |
| 21 | CH₃ | 3-pyrazole-CH₂ |

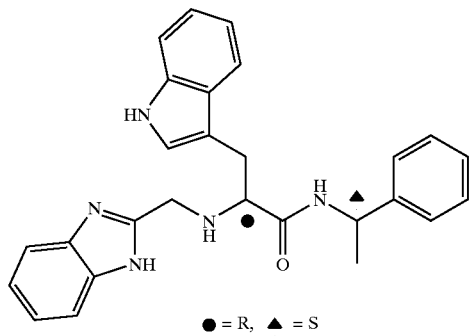

● = R, ▲ = S

Example 9 i. bis(4-nitrophenyl) carbonate, DMF
ii. Intermediate V, DMF

Scheme 8

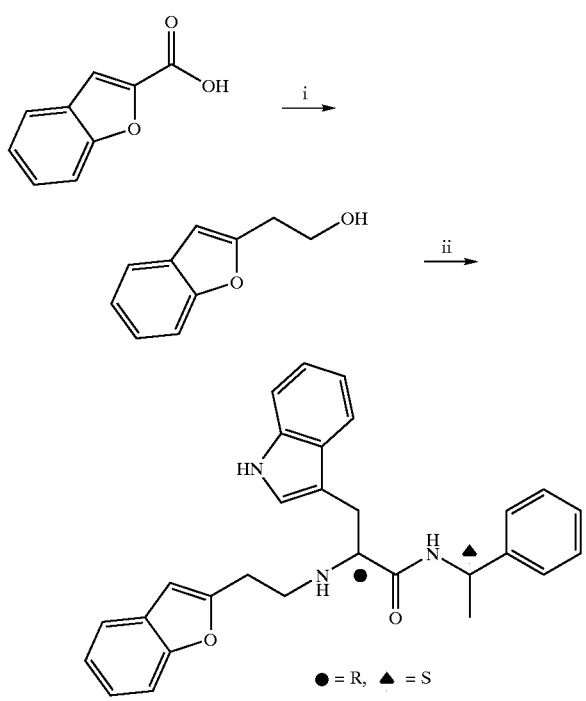

● = R, ▲ = S

Example 7 i. a) NMM, EtOCOCl, THF b) LiBH₄
ii. Ether, CH₃SO₂Cl, NEt₃, Intermediate V

Scheme 10

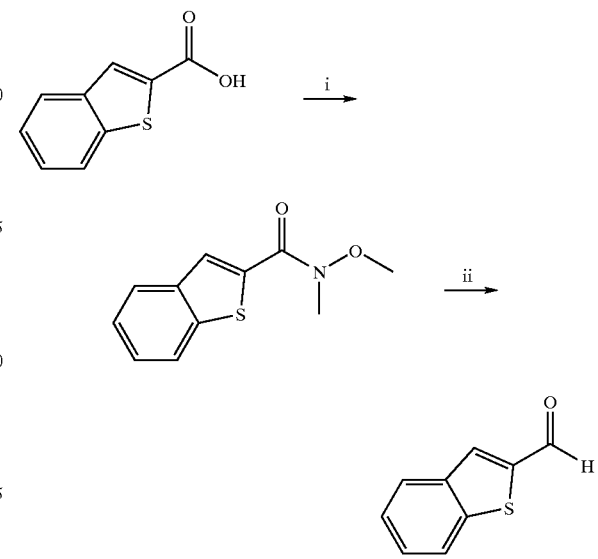

Intermediate VI i. NMM, EtOCOCl, THF, NHMeOME
ii DIBAL

Scheme 9

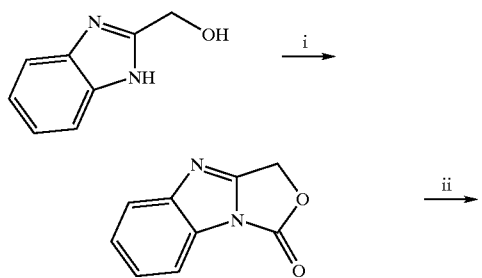

Scheme 11

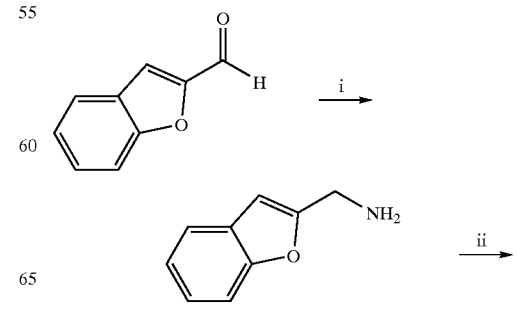

29
-continued

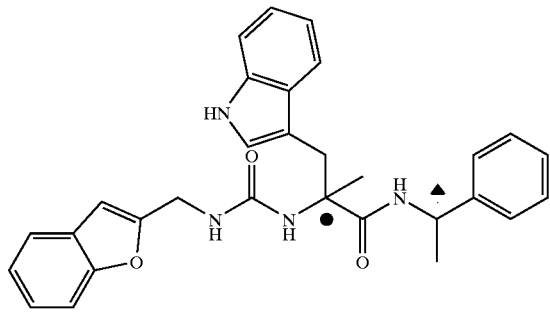

● = R, ▲ = S

Example 22 i. a) KOH, NH₂OH, EtOH, H₂O
   b) LiAlH₄
ii. triphosgene, DCM, pyridine
   2-amino-3-(1H-indol-3-yl)-2-methyl-N-(1-phenyl-ethyl)-propionamide Scheme 12

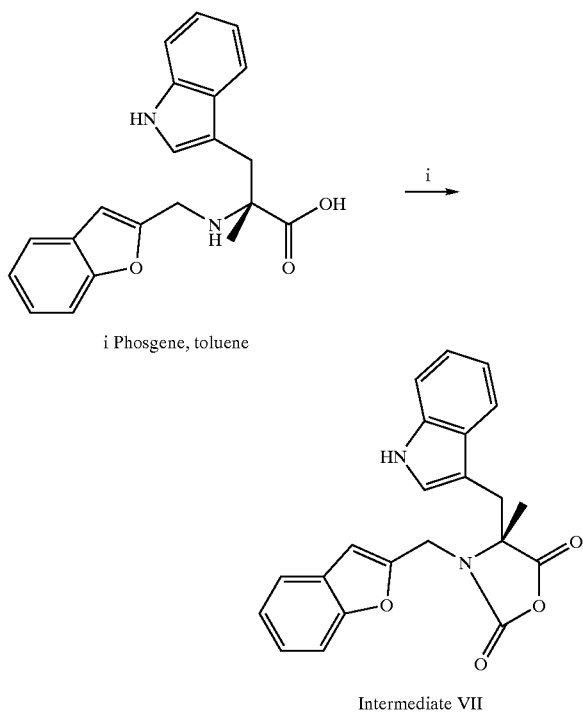

i Phosgene, toluene

Intermediate VII

EXAMPLE 6

2-[(Benzofuran-2-ylmethyl)-amino]-3-(1H-indol-3-yl)-N-(1-phenyl-ethyl)-propionamide, [R-(R*,S*)]

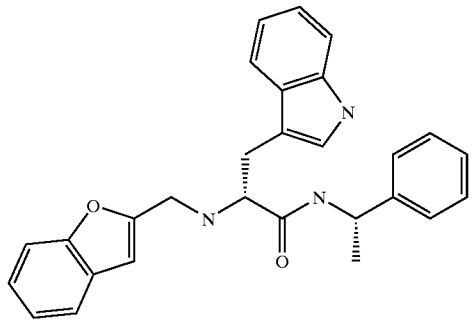

30

Step 1 Intermediate V

To a stirred solution of Boc-(R)-Trp-OH (6.08 g, 0.02 mol) in DMF (50 mL) was added HBTU (7.59, 0.02 mol) and DIPEA (3.57 mL, 0.02 mol). After 5 min DIPEA (3.57 mL, 0.02 mol) and (S)-(-)-α-methylbenzylamine in DMF (10 mL) was added. After a further 60 min, the solvent was removed under reduced pressure. The residue was taken up in EtOAc (250 mL) and washed with brine (50 mL), 1N HCl (100 mL), saturated NaHCO₃ (3×100 mL), brine (50 mL), dried (MgSO₄), filtered and the solvent was removed under reduced pressure. The residue was dissolved in CH₂Cl₂ (20 mL) and formic acid (30 mL). The reaction was stirred over night at room temperature before refluxing for 4 h. The solvent was removed under reduced pressure and the product was crystallized from ether. Stirring in EtOAc (100 mL) for 4 h and filtration gave pure product (4.17 g, 68%). The filtrate was purified by chromatography using EtOAc and then EtOAc/MeOH/NH₃(aq) (95:5:0.5) as eluent. Crystallization from ether gave white crystalline solid (0.98 g , 16%); mp 142–144° C.; $[\alpha_D^{19}]=-83.9°$ (c=1, MeOH); IR (film): 3338, 3295, 3059, 2975, 2928, 1649, 1518, 1494, 1455, 1342, 1104, 894, 740 cm⁻¹; NMR (CDCl₃): δ1.44 (3H, d, J=7.1 Hz); 1.51 (2H, s); 2.95 (1H, d,d, J=14.4 and 8.5 Hz); 3.36 (1H, d,d, J=14.4 and 4.4 Hz); 3.74 (1H, d,d, J=8.5 and 4.4 Hz); 5.05–5.15 (1H, m); 6.95 (1H, d, J=2.2 Hz); 7.10–7.38 (8H, m); 7.48–7.52 (1H, m); 7.66–7.69 (1H, m); 7.98 (1H, s); MS m/e (APCI⁺): 309.1 (20%), 308.1 (100%, M⁺+H); Analysis calculated for C₁₉H₂₁N₃O: C, 74.24; H, 6.89; N, 13.66%. Found: C, 74.07; H, 6.87; N, 13.70%.

Step 2

To a stirred solution of 2-benzofurancarboxaldehyde (0.73 g, 5 mmol) in 1,2-dichloroethane (20 mL) was added intermediate V (1.54 g, 5 mmol) followed by sodium triacetoxyborohydride (1.48 g, 7 mmol). After stirring for 3 h the reaction was cautiously quenched with saturated NaHCO₃ (20 mL) and extracted with CH₂Cl₂ (3×50 mL). The combined organic phases were dried (MgSO₄) and the solvent was removed under reduced pressure. The residue was purified by chromatography using 30% EtOAc in heptane as eluent to give pure product as a glass (2.0 g, 91%); $[\alpha_D^{20}]=+34.0$ (c=0.5, MeOH); IR (film): 3316, 3059, 2973, 2925, 1653, 1517, 1455, 1341, 1254, 1104, 1010, 909, 741 cm⁻¹; NMR (CDCl₃): δ1.38 (3H, d, J=7.1 Hz); 1.93 (1H, s); 2.92 (1H, d,d, J=14.6 and 9.3 Hz); 3.29–3.35 (1H, m); 3.58 (1H, d,d, J=9.3 and 4.2 Hz); 3.75 (1H, d, J=14.9 Hz); 3.82 (1H, d, J=14.9 Hz); 5.07–5.15 (1H, m); 6.36 (1H, s); 6.87 (1H, d, J=2.2 Hz); 7.04–7.08 (1H, m); 7.15–7.35 (10H, m); 7.43–7.45 (1H, m); 7.58–7.64 (2H, m); 7.92 (1H, s); MS m/e (APCI⁺): 439.9 (5%), 438.9 (34%), 437.9 (100%, M⁺+H), 307.0 (9%); Analysis calculated for C₂₈H₂₇N₃O₂: C, 76.86; H, 6.22; N, 9.60%. Found: C, 77.11; H, 6.31; N, 9.67%.

EXAMPLE 7

2-(2-Benzofuran-2-yl-ethylamino)-3-(1H-indol-3-yl)-N-(1-phenyl-ethyl)-propionamide, [R-(R*,S*)]

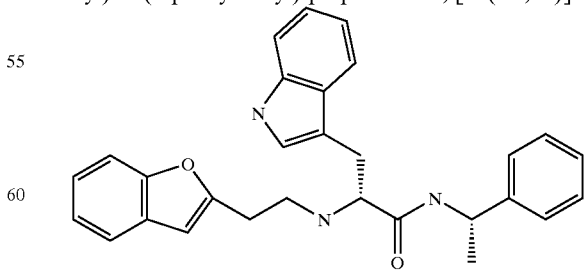

Step 1

A solution of N-methylmorpholine (NMM, 5.31 g, 52.5mmol) in THF (30 mL) was added dropwise over 15 min to a stirred solution of 2-benzofuranacetic acid (8.80 g, 50 mmol) and ethyl chloroformate (5.70 g, 52.5 mmol) in THF (150 mL, anhydrous) at 0° C. The reaction mixture was stirred for 1 h at room temperature before filtering off the precipitate of NMM.HCl. The filtrate was cooled to 0° C. and a solution of lithium borohydride (30 mL, 60 mmol, 2M in THF) was added dropwise over 30 min. The reaction was allowed to reach room temperature and stirred over night before being cautiously quenched with 1N HCl (100 mL)—vigorous effervescence. The THF was removed under reduced pressure and the aqueous phase was extracted with EtOAc (200 mL). The organic phase was washed with 1N HCl, $H_2O$, saturated $NaHCO_3$ (×2), brine, and dried ($MgSO_4$). Removal of solvent under reduced pressure gave intermediate VI (7.74 g, 93%). Used in the next step without further purification. IR (film): 3347, 2957, 2887, 1603, 1587, 1455, 1422, 1317, 1252, 1167, 1105, 1049, 945, 926, 881, 854, 807, 751 cm$^{-1}$; NMR (CDCl$_3$): δ1.64 (1H, t, J=6.0 Hz); 3.05 (2H, t, J=6.2 Hz); 4.00 (2H, q, J=6.1 Hz); 6.51 (1H, d, J=1.0 Hz); 7.17–7.25 (2H, m); 7.41–7.44 (1H, m); 7.49–7.52 (1H, m).

Step 2

To an ice-cold solution of alcohol VI (1.62 g, 10 mmol) and NEt$_3$ (1.01 g, 10 mmol) in ether (50 mL, anhydrous) was added a solution of methanesulphonyl chloride (1.20 g, 10.5 mmol) dropwise over 5 min. The ice bath was removed and the reaction was stirred at room temperature for 30 min before filtering off the NEt$_3$.HCl. The ether was removed under reduced pressure. To a portion of the mesylate (240 mg, 1 mmol) dissolved in toluene (50 mL, anhydrous) was added amine V. The reaction was refluxed for 48 h, a further equivalent of NEt$_3$ was added, and reflux was continued for a further 48 h. The reaction mixture was cooled and washed with 1N NaOH, the organic layer was dried (MgSO$_4$), and solvent removed under reduced pressure. The residue was purified by chromatography on normal phase silica using 20% EtOAc in heptane as eluent and then on reverse phase silica using 70% MeOH in H$_2$O as elan. Product crystallized on drying in vacuum oven to give pure product (82 mg, 18%); mp 105–107° C.; [α]D$^{22}$=−1.2° (c=0.25, MeOH); IR (film): 3305, 3058, 2924, 2851, 1651, 1515 1455, 1356, 1342, 1252, 1166, 1105, 742 cm$^{-1}$; NMR (CDCl$_3$): δ1.37 (3H, d, J=7.1 Hz); 1.57 (1H, s); 2.72–2.97 (5H, m); 3.28–3.34 (1H, m); 3.44–3.48 (1H, m); 5.07–5.15 (1H, m); 6.06 (1H, s); 6.75 (1H, d, J=2.2 Hz); 7.06–7.33 (11H, m); 7.40–7.44 (1H, m); 7.51 (1H, d, J=8.5 Hz); 7.62–7.65 (2H, m); MS m/e (ES$^+$): 453.1 (33%), 452.2 (100%, M$^+$+H); Analysis calculated for C$_{29}$H$_{29}$N$_3$O$_2$: C, 77.14; H, 6.47; N, 9.31%. Found: C, 77.06; H, 6.48; N, 9.30%.

EXAMPLE 8

2-[(4,5-Dimethyl-furan-2-ylmethyl)-amino]-3-(1H-indol-3-yl)-N-(1-phenyl-ethyl)-propionamide, [R-(R*,S*)]

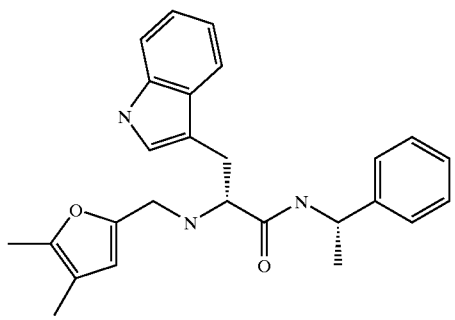

To a stirred solution of the 4,5-dimethyl-2-furaldehyde (124 mg, 1 mmol) in 1,2-dichloroethane (20 mL) was added intermediate V (307 mg, 1 mmol) followed by sodium triacetoxyborohydride (424 mg, 2 mmol). After stirring over night the reaction was cautiously quenched with saturated NaHCO$_3$ (20 mL) and extracted with CH$_2$Cl$_2$ (2×20 mL). The combined organic phases were dried (MgSO$_4$) and the solvent was removed under reduced pressure. The residue was purified by chromatography on normal phase silica using 25% EtOAc in heptane as eluent to give pure product as a glass (196 mg, 47%); [α]$_D$$^{21}$=+18.6° (c=0.5, MeOH); IR (film): 3312, 3059, 2971, 2922, 1651, 1516, 1455, 1342, 1220, 1106, 741 cm$^{-1}$; NMR (CDCl$_3$): δ1.44 (3H, d, J=6.8 Hz); 1.60–1.90 (1H, br.s); 1.83 and 2.06 (each 3H, s); 2.89 (1H, d.d, J=14.6 and 9.3 Hz); 3.26–3.32 (1H, m); 3.49 (1H, d, J=14.4 Hz); 3.50–3.54 (1H, m); 3.58(1H, d, J=14.4 Hz); 5.08–5.16 (1H, m); 5.76 (1H, s); 6.89 (1H, d, J=2.2 Hz); 7.01–7.11 (1H, m); 7.17–7.36 (7H, m); 7.62–7.65 (2H, m); 7.95 (1H, s); MS m/e (ES$^+$): 417.3 (31%), 416.3 (100%, M$^+$+H), 308.3 (34%); Analysis calculated for C$_{26}$H$_{29}$N$_3$O$_2$.H$_2$O: C, 74.51; H, 7.07; N, 10.03%. Found: C, 74.43; H, 6.82; N, 10.03%.

EXAMPLE 9

2-[(1H-Benzoimidazol-2-ylmethyl)-amino]-3-(1H-indol-3-yl)-N-(1-phenyl-ethyl)-propionamide, [R-(R*,S*)]

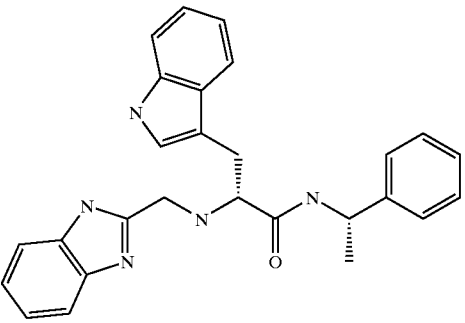

Step 1

A solution of 2-hydroxymethyl benzimidazole (1.19 g, 8 mmol) and bis(4-nitrophenyl) carbonate (2.43 g, 8 mmol) in DMF (20 mL, anhydrous) was stirred for 12 h at room temperature. The DMF was removed under reduced pressure and the residue stirred in ether (50 mL) for 2 h. Filtration and washing with ether (50 mL) gave crystalline intermediate VII (1.04 g, 74%); IR (film): 1819, 1623, 1592, 1568, 1486, 1445, 1411, 1369, 1359, 1147, 1106, 1076, 1009, 997, 941, 862, 847, 765, 750, 741 cm$^{-1}$; NMR (CDCl$_3$): δ5.49 (2H, s); 7.42–7.50 (2H, m); 7.79–7.84 (1H, m); 7.88–7.93 (1H, m).

Step 2

The product from step 1 (174 mg, 1 mmol) and intermediate V (307 mg, 1 mmol) were dissolved in DMF (10 mL, anhydrous) and stirred at 60° C. for 10 h. The solvent was removed under reduced pressure and the residue was purified by chromatography on reverse phase silica using 60% MeOH in H$_2$O as eluent. The solvent was removed under reduced pressure and the residue was crystallized from EtOAc to give pure product (396 mg, 91%); mp 148–152.5° C.; [α]$_D$$^{21}$=+24.2° (c=0.5, MeOH); IR (film): 3300, 3058, 2923, 1651, 1520, 1455, 1340, 1271, 1235, 1218, 1109, 1013, 909, 739 cm$^{-1}$; NMR (CDCl$_3$): δ1.31 (3H, d, J=7.1 Hz); 2.00–2.50 (1H, br.s); 3.04 (1H, d.d, J=14.4 and 8.8 Hz); 3.29 (1H, d.d, J=14.4 and 5.2 Hz); 3.50 (1H, d.d, J=8.8 and 5.2 Hz); 3.94 (1H, d, J=15.9 Hz); 4.04 (1H, d, J=15.9 Hz); 5.03–5.10 (1H, m); 6.85 (1H, d, J=7.8 Hz); 6.99 (1H, d, J=2.2 Hz); 7.10–7.30 (10H, m); 7.20–7.70 (1H, br.s); 7.42 (1H, d, J=8.1 Hz); 7.66 (1H, d, J=7.8 Hz); 8.06 (1H, s); 8.80–9.20 (1H, br.s); MS m/e (ES$^+$): 439.3 (28%), 438.3

(100%, M⁺+H); Analysis calculated for C₂₇H₂₇N₅O: C, 74.12; H, 6.22; N, 16.01%. Found: C, 74.04; H, 6.19; N, 15.95%.

EXAMPLE 10

2-[(Benzo[b]thiophen-2-ylmethyl)-amino]-3-(1H-indol-3-yl)-N-(1-phenyl-ethyl)-propionamide

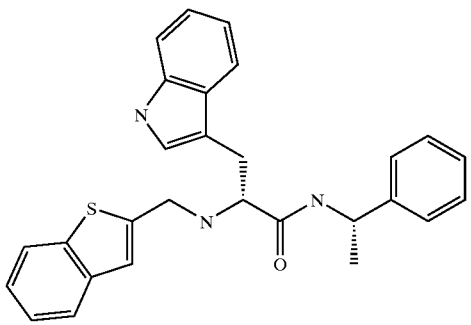

Step 1

A solution of NMM (2.309 mL, 21 mmol) in THF (10 mL) was added dropwise to a stirred ice cooled solution of benzo[b]thiophene-2-carboxylic acid (3.56 g, 20 mmol) and ethyl chloroformate (2.008 mL, 21 mmol) in THF (150 mL) over 15 mins. The reaction mixture was stirred at room temperature for 1 h before adding N,O-dimethylhydroxylamine hydrochloride (2.146 g, 22 mmol) and NMM (2.419 mL, 22 mmol). The reaction was stirred at room temperature over night. The solvent was removed under reduced pressure. The residue was taken up in EtOAc (100 mL) and washed with 2N HCl (3×100 mL), 2N NaOH (100 mL), H₂O, brine, dried (MgSO₄), and the solvent was removed under reduced pressure. The residue was purified by chromatography on normal phase silica using 30% EtOAc in heptane as eluent. Crystallization from ether/heptane gave pure product (3.24 g, 73%).

To a stirred solution of the Weinreb amide (2.06 g, 9.3 mmol) in THF (100 mL, anhydrous) under nitrogen at 0° C. was added diisobutylaluminum hydride (11 mL, 11 mmol, 1M in CH₂Cl₂) dropwise. After 20 min the reaction mixture was poured onto ice cold 2N HCl and extracted with ether. The organic phase was washed with brine, dried (MgSO₄), and the solvent was removed under reduced pressure. The residue was purified by chromatography on normal phase silica using 5% EtOAc in heptane as eluent to give solid benzo[b]thiophene-2-carboxaldehyde (Intermediate VI) (665 mg, 44%). IR (film): 1669, 1592, 1516, 1431, 1255, 1224, 1135, 840, 747, 725 cm⁻¹; NMR (CDCl₃): δ7.42–7.54 (2H, m); 7.91 (1H, d, J=8.1 Hz); 7.95(1H, d, J=7.8 Hz); 8.04 (1H, s); 10.12 (1H, s).

Step 2

To a stirred solution of the benzo[b]thiophene-2-carboxaldehyde (Intermediate VI) (162 mg, 1 mmol) in 1,2-dichloroethane (20 mL) was added intermediate V (307 mg, 1 mmol) followed by sodium triacetoxyborohydride (424 mg, 2 mmol). After stirring over night the reaction was cautiously quenched with saturated NaHCO₃ (20 mL) and extracted with CH₂Cl₂ (2×20 mL). The combined organic phases were dried (MgSO₄) and the solvent was removed under reduced pressure. The residue was purified by chromatography on normal phase silica using 20% EtOAc in heptane as eluent. Crystallization from ether/heptane gave pure product (305 mg, 67%); mp 102–108° C.; [α]_D²¹=+ 51.40° (c=0.5, MeOH); IR (film): 3311, 3059, 292 1651, 1515, 1456, 743 cm⁻¹; NMR (CDCl₃): δ1.40 (3H, d, J=7.1 Hz); 1.97 (1H, s); 2.99 (1H, d.d, J=14.7 and 8.8 Hz); 3.35 (1H, d.d, J=14.4 and 4.2 Hz); 3.59 (1H, d.d, J=8.5 and 4.4 Hz); 3.94 (2H, m); 5.07–5.16 (1H, m); 6.91–6.93 (2H, m); 7.06–7.11 (1H, m); 7.17–7.37 (9H, m); 7.50 (1H, d, J=8.5 Hz); 7.60 (1H, d.d, J=7.0 and 1.6 Hz); 7.65 (1H, d, J=8.1 Hz); 7.72–7.76 (1H, m); 7.95 (1H, s); MS m/e (ES⁺): 476.1 (60%, M⁺+Na), 454.1 (100%, M⁺+H), 402.2 (25%); (ES⁻): 453.2 (25%), 452.1 (100%, M⁻−H); Analysis calculated for C₂₈H₂₇N₃OS: C, 74.14; H, 6.00; N, 9.26; S, 7.07%. Found: C, 74.27; H, 6.16; N, 9.31; S, 7.11%.

EXAMPLE 11

3-(1H-Indol-3-yl)-N-(1-phenyl-ethyl)-2-[(quinolin-3-ylmethyl)-amino]-propionamide, [R-(R*,S*)]

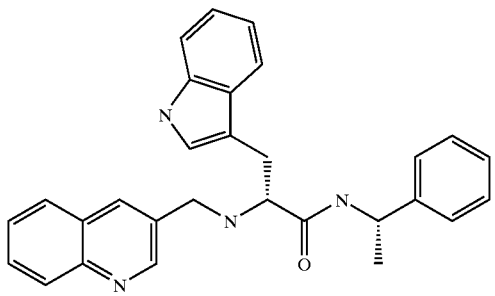

Method as for Example 10, step 2. The residue was purified by chromatography on normal phase silica using 2% MeOH in CH₂Cl₂ as eluent. Crystallization from EtOAc/heptane gave pure product (340 mg, 76%); mp 161–163° C.; [α]_D²²=+40° (c=0.5, MeOH); IR (film): 3280, 3055, 2972, 2926, 1655, 1515, 1497, 1456, 1342, 1127, 742 cm⁻¹; NMR (CDCl₃): δ1.40 (3H, d, J=7.1 Hz); 1.90 (1H, s); 2.96 (1H, d.d, J=14.7 and 9.0 Hz); 3); 36 (1H, d.d, J=14.5 and 4.5 Hz); 3.53–3.56 (1H, m); 3.78 (1H, d, J=13.7 Hz); 3.92 (1H, d, J=13.7 Hz); 5.08–5.16 (1H, m); 6.90 (1H, d, J=2.2 Hz); 7.03–7.08 (1H, m); 7.15–7.20 (1H, m); 7.23–7.37 (6H, m); 7.43 (1H, d J=8.3 Hz); 7.49–7.51 (1H, m); 7.59–7.72 (4H, m); 8.02 (1H, s); 8.04 (1H, d, J=8.3 Hz); 8.66 (1H, d, J=2.2 Hz); MS m/e (ES⁺): 471.1 (31%, M⁺+Na), 449.1(100%, M⁺+H); Analysis calculated for C₂₉H₂₈N₄O: C, 77.65; H, 6.29; N, 12.49%. Found: C, 78.02; H, 6.30; N, 12.48%.

EXAMPLE 12

2-[(5-Chloro-thiophen-2-ylmethyl)-amino]-3-(1H-indol-3-yl)-N-(1-phenyl-ethyl)-propionamide, [R (R*,S*)]

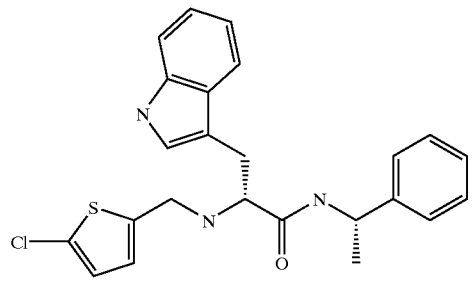

Method as for Example 10, step 2. The residue was dissolved in aqueous acetonitrile and acidified using formic acid before being purified by chromatography on reverse phase silica using 40% CH₃CN in H₂O (0.1% formic acid in mobile phases) as eluent. The solvent was removed under reduced pressure and the residue was suspended between EtOAc and saturated NaHCO₃. The EtOAc was dried (MgSO₄) and the solvent was removed under reduced pressure to give pure product as a glass (245 mg, 56%); $[\alpha]_D^{22}$=+26.2° (c=0.5, MeO); IR (film): 3307, 3059, 2973, 2925, 1652, 1515, 1455, 1342, 1230, 1105, 1061, 1000, 796, 742 cm⁻¹; NMR (CDCl₃): δ1.43 (3H, d, J=6.8 Hz); 1.85 (1H, s); 2.96 (1H, d.d, J=14.7 and 8.5 Hz); 3.31 (1H, d.d, J=14.5 and 4.5 Hz); 3.49–3.53 (1H, m); 3.71–3.79 (2H, m); 5.07–5.15 (1H, m); 6.50 (1H, d, J=3.7 Hz); 6.65 (1H, d, J=3.9 Hz); 6.91 (1H, d, J=2.4 Hz); 7.09–7.14 (1H, m); 7.18–7.39 (8H, m); 7.63 (1H, d, J=7.6 Hz); 7.98 (1H, s); MS m/e (ES⁺): 437.9 (100%, M⁺+H); Analysis calculated for C₂₄H₂₄N₃OSCl: C, 65.81; H, 5.52; N, 9.59; Cl, 8.09; S, 7.32%. Found: C, 65.54; H, 5.45; N, 9.40; Cl, 7.85; S, 7.42%.

EXAMPLE 13

3-(1H-Indol-3-yl)-N-(1-phenyl-ethyl)-2-(3-trifluoromethylsulfanyl-benzylamino)-propionamide, [R-(R*,S*)]

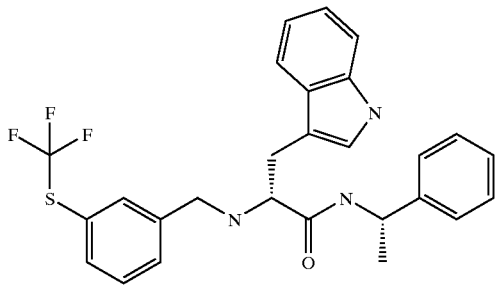

To a stirred solution of 3-(trifluoromethylthio) benzaldehyde (72 mg, 0.55 mmol) in 1,2-dichloroethane (20 mL) was added intermediate V (154 mg, 0.5 mmol) followed by sodium triacetoxyborohydride (148 mg, 0.7 mmol). After stirring over night the reaction was cautiously quenched with saturated NaHCO₃ (20 mL) and extracted with CH₂Cl₂ (3×50 mL). The combined organic phases were dried (MgSO₄) and the solvent was removed under reduced pressure. The residue was purified by chromatography on normal phase silica using 30% EtOAc in heptane as eluent. The solvent was removed under reduced pressure to give pure product as a glass (193 mg, 77%); IR (film): 3306, 3058, 2972, 2923, 1651, 1516, 1456, 1342, 1114, 743 cm⁻¹; NMR (CDCl₃): δ1.41 (3H, d, J=6.8 Hz); 1.60–1.90 (1H, br.s); 2.96 (1H, d.d, J=14.5 and 8.9 Hz); 3.32 (1H, d.d, J=14.4 and 4.4 Hz); 3.48 (1H, d.d, J=8.9 and 4.5 Hz); 3.62 (1H, d, J=13.9 Hz); 3.76 (1H, d, J=13.7 Hz); 5.08–5.16 (1H, m); 6.91 (1H, d, J=2.2 Hz); 7.07–7.48 (13H, m); 7.60 (1H, d, J=7.8 Hz); 7.97 (1H, s); MS m/e (ES⁺): 499.4 (32%), 498.4 (100%, M⁺+H); Analysis calculated for C₂₇H₂₆N₃OSF₃. 0.25H₂O: C, 64.59; H, 5.32; N, 8.37; S, 6.39%. Found: C, 64.69; H, 5.34; N, 8.30; S, 6.27%.

EXAMPLE 14

2-(3-Cyano-benzylamino)-3-(1H-indol-3-yl)-N-(1-phenyl-ethyl)-propionamide, [R-(R*,S*)]

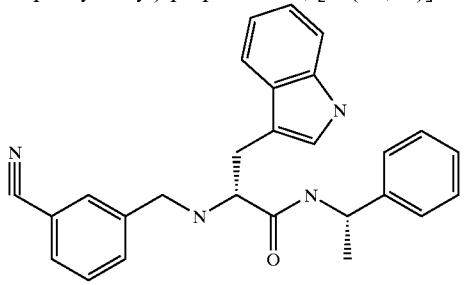

Method as for Example 13. Chromatography on normal phase silica using 45% EtOAc in heptane as the eluent and subsequent removal of the solvent under reduced pressure gave pure product as a glass (130 mg, 62%); IR (film): 3312, 3059, 2973, 2924, 2229, 1652, 1516, 1456, 1342, 1231, 1101, 743 cm⁻¹; NMR (CDCl₃): δ1.42 (3H, d, J=6.8 Hz); 1.87 (1H, s); 2.91 (1H, d.d, J=14.5 and 9.2 Hz); 3.32 (1H, d.d, J=14.5 and 4.0 Hz); 3.41 (1H, d.d, J=9.0 and 4.4 Hz); 3.58 (1H, d, J=14.2 Hz); 3.76 (1H, d, J=14.2 Hz); 5.08–5.17 (1H, m); 6.94 (1H, d, J=2.2 Hz); 7.07–7.12 (1H, m); 7.19–7.45 (12H, m); 7.58 (1H, d, J=8.1 Hz); 8.05 (1H, s); MS m/e (ES⁺) 424.4 (30%), 423.4 (100%, M⁺+H); (ES⁻): 422.3 (30%, M⁻), 421.3 (100%, M⁻–H); Analysis calculated for C₂₇H₂₆N₄O: C, 76.75; H, 6.20; N, 13.26%. Found: C, 76.58; H, 6.14; N, 13.24%.

EXAMPLE 15

3-(1H-Indol-3-yl)-2-(3-nitro-benzylamino)-N-(1-phenyl-ethyl)-propionamide, [R-(R*,S*)]

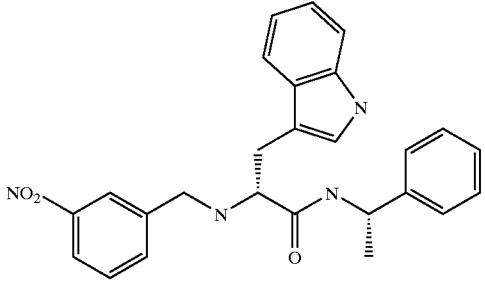

To a stirred solution of 3-nitrobenzaldehyde (332 g, 2.2 mmol) in 1,2-dichloroethane (60 mL) was added intermediate V (614 mg, 2 mmol) followed by sodium triacetoxyborohydride (594 mg, 2.8 mmol). After stirring over night the reaction was cautiously quenched with saturated NaHCO₃ (20 mL) and extracted with CH₂Cl₂ (3×50 mL). The combined organic phases were dried (MgSO₄) and the solvent was removed under reduced pressure. The residue was purified by chromatography on normal phase silica using 45% EtOAc in heptane as eluent. The solvent was removed under reduced pressure to give pure product as a glass (648 mg, 73%); IR (film): 3317, 2925, 1652, 1526, 1456, 1349, 733 cm⁻¹;NMR (CDCl₃): δ1.43 (3H, d, J=6.8 Hz); 1.85–1.95 (1H, br.s); 2.90 (1H, d.d, J=14.5 and 9.1 Hz); 3.33 (1H, d.d, J=14.4 and 4.4 Hz); 3.43 (1H, d.d, J=9.0 and 4.5 Hz); 3.65 (1H, d, J=14.2 Hz); 3.83 (1H, d, J=14.2 Hz); 5.09–5.17 (1H, m); 6.94 (1H, d, J=2.4 Hz); 7.06 (1H, t, J=7.5 Hz); 7.18 (1H, t, J=7.5 Hz); 7.22–7.40 (10H, m); 7.87 (1H, m); 7.97–8.10 (2H, m); MS m/e (ES⁺): 444.4 (30%), 443.4 (100%, M⁺+H); Analysis calculated for C₂₆H₂₆N₄O₃: C, 70.57; H, 5.92; N, 12.66%. Found: C, 70.55; H, 5.88; N, 12.67%.

EXAMPLE 16

3-(1H-Indol-3-yl)-N-(1-phenyl-ethyl)-2-(3-trifluoromethoxy-benzylamino)-propionamide, [R-(R*,S*)]

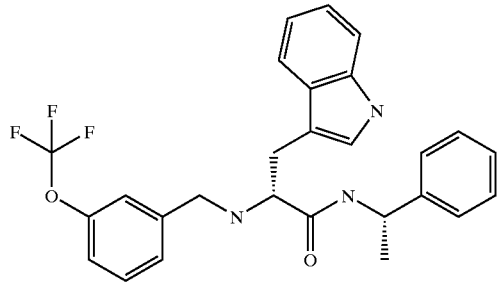

Method as for Example 13. Chromatography on normal phase silica using 35% EtOAc in heptane as the eluent and subsequent removal of the solvent under reduced pressure gave pure product as a glass (130 mg, 54%); IR (film): 3307, 3060, 2974, 2925, 1652, 1589, 1516, 1495, 1456, 1260, 1217, 1164, 1012, 743 cm$^{-1}$; NMR (CDCl$_3$): δ1.40 (3H, d, J=6.8 Hz); 1.60–2.00 (1H, br.s); 2.97 (1H, d.d, J=14.7 and 8.8 Hz); 3.29–3.35 (1H, m); 3.48 (1H, d.d, J=8.8 and 4.6 Hz); 3.62 (1H, d, J=13.9 Hz); 3.74 (1H, d, J=13.9 Hz); 5.07–5.15 (1H, m); 6.91 (1H, d, J=2.2 Hz); 6.96–7.39 (13H, m); 7.63 (1H, d, J=7.8 Hz); 7.97 (1H, m); MS m/e (ES$^+$): 483.4 (30%), 482.4 (100%, M$^+$+H); Analysis calculated for C$_{27}$H$_{26}$N$_3$O$_2$F$_3$: C, 67.35; H, 5.44; N, 8.73%. Found: C, 67.31; H, 5.43; N, 8.67%.

EXAMPLE 17

2-(3-Hydroxy-benzylamino)-3-(1H-indol-3-yl)-N-(1-phenyl-ethyl)-propionamide, [R-(R*,S*)]

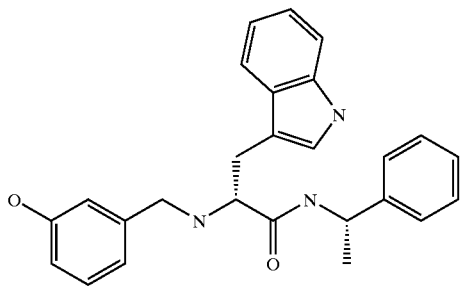

Method as for Example 13. Chromatography on normal phase silica using 40% EtOAc in heptane as the eluent and subsequent removal of the solvent under reduced pressure gave pure product as a glass (94 mg, 45%); IR (film): 3317, 3059, 2975, 2926, 1645, 1589, 1520, 1456, 1266, 1159, 743 cm$^{-1}$; NMR (CDCl$_3$): δ1.40 (3H, d, J=7.1 Hz); 1.70–1.90 (1H, br.s); 2.89 (1H, d.d, J=14.5 and 9.4 Hz); 3.33 (1H, d.d, J=14.7 and 4.2 Hz); 3.49–3.54 (1H, m); 3.53 (1H, d, J=13.9 Hz); 3.69 (1H, d, J=13.9 Hz); 5.00–5.20 (2H, m); 6.28 (1H, d, J=1.7 Hz); 6.60 (1H, d, J=7.6 Hz); 6.65 (1H, d.d, J=7.9 and 2.0 Hz); 6.89 (1H, d, J=2.2 Hz); 7.06 (1H, t, J=7.8 Hz); 7.09–7.13 (1H, m); 7.19–7.52 (7H, m); 7.54 (1H, d, J=8.5 Hz); 7.64 (1H, d, J=8.5 Hz); 8.05 (1H, m); MS m/e (ES$^+$): 415.4 (30%), 414.4 (100%, M$^+$+H); Analysis calculated for C$_{26}$H$_{27}$N$_3$O$_2$: C, 75.52; H, 6.58; N, 10.16%. Found: C, 75.28; H, 6.61; N, 10.03%.

EXAMPLE 18

2-[(Benzofuran-2-ylmethyl)-amino]-3-(1H-indol-3-yl)-2-methyl-N-(1-phenyl-ethyl)-propionamide, [R-(R*,S*)]

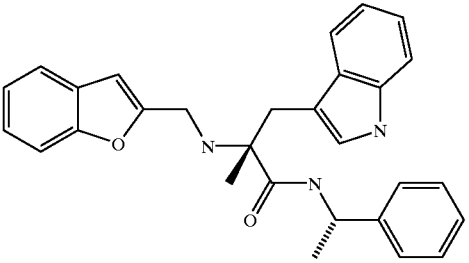

To a stirred solution of 2-benzofurancarboxaldehyde (3.19 g, 21.8 mmol) in 1,2-dichloroethane (150 mL) was added 2-amino-3-(1H-indol-3-yl)-2-methyl-N-(1-phenyl-ethyl)-propionamide (prepared as described by Boyle S. et al., Bioorg. Med. Chem. 2:357, 1994) (5 g, 15.6 mmol), followed by sodium triacetoxyborohydride (6.6 mg, 31.2 mmol). After stirring over night the reaction was cautiously quenched with 2N NaOH (150 mL) and extracted with CH$_2$Cl$_2$ (3×200 mL). The combined organic phases were dried (MgSO$_4$) and the solvent was removed under reduced pressure. The residue was purified by chromatography on normal phase silica using 30% EtOAc in heptane as eluent and then on reverse phase silica using 70% MeOH in H$_2$O as eluent. Crystallization from ether gave pure product (5.55 g, 79%); mp 118–121° C.; [α$_D^{20}$=+12.5° (c=1, MeOH); IR (film): 3329, 3059, 2975, 2926, 1652, 1506, 1455, 1371, 1354, 1342, 1255, 1170, 1105, 1010, 938, 743 cm$^{-1}$; NMR (CDCl$_3$): δ1.47 (3H, s); 1.47 (3H, d, J=6.8 Hz); 1.89 (1H, s); 3.16 (2H, s); 3.78 (1H, br.d, J=12.9 Hz); 3.86 (1H, d, J=14.4 Hz); 5.05–5.13 (1H, m); 6.43 (1H, s); 6.87 (1H, d, J=2.2 Hz); 7.09–7.40 (11H, m); 7.47–7.50 (1H, m); 7.65 (1H, d, J=7.8 Hz); 7.92 (1H, d, J=7.8 Hz); 7.96 (1H, s); MS m/e (ES$^+$): 453.1 (30%), 452.1 (100%, M$^+$+H), 393.2 (15%); Analysis calculated for C$_{29}$H$_{29}$N$_3$O: C, 77.14; H, 6.47; N, 9.30%. Found: C, 77.14; H, 6.42; N, 9.36%.

EXAMPLE 19

2-[(Benzofuran-3-ylmethyl)-amino]-3-(1H-indol-3-yl)-2-methyl-N-(1-phenyl-ethyl)-propionamide, [R-(R*,S*)]

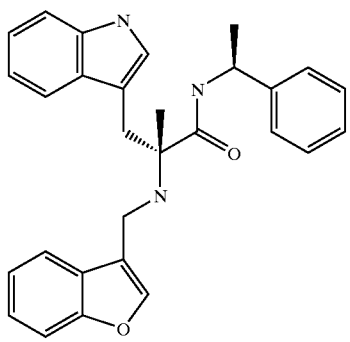

To a stirred solution of 3-benzofurancarboxaldehyde (146 mg, 1 mmol) (Ind. J. Chem., Vol. 31B, 1992, 526) in 1,2-dichloroethane (10 mL) was added 2-amino-3-(1H-indol-3-yl)-2-methyl-N-(1-phenyl-ethyl)-propionamide (321 mg, 1 mmol) followed by sodium triacetoxyborohydride (424 mg, 2 mmol). After stirring over night at room temperature another portion of sodium triacetoxyborohydride (424 mg, 2 mmol) was added. The reaction was heated to reflux for 4 h. Cooled to room temperature and cautiously quenched with saturated NaHCO$_3$ (100 mL) and extracted with CH$_2$Cl$_2$ (3×20 mL). The combined organic phases were dried (MgSO$_4$) and the solvent was removed under reduced pressure. The residue was purified by chromatography on normal phase silica using 25% EtOAc in heptane as eluent. Crystallization from ether/heptane gave pure product (232 mg, 51%); mp 104–106° C.: [α]$_D^{23}$=13.4° (c=1, MeOH); IR (film): 3418, 3314, 3058, 2976, 2927, 1652, 1505, 1452, 1371, 1354, 1341, 1279, 1266, 1186, 1095, 1010, 858, 743 cm$^{-1}$; NMR (CDCl$_3$): δ1.40 (3H, d, J=6.8 Hz); 1.52 (3H, s); 1.71 (1H, s); 3.15 (1H, d, J=14.4 Hz); 3.27 (1H, d, J=14.4 Hz); 3.80 (1H, d, J=3.2 Hz); 3.88 (1H, d, J=13.2 Hz); 5.01–5.09 (1H, m); 6.79 (1H, d, J=2.2 Hz); 7.07–7.40 (12H, m); 7.44 (1H d.d, J=8.3 and 0.7 Hz); 7.65 (1H, d, J=7.8 Hz); 7.68 (1H, d, J=8.1 Hz); 7.93 (1H, s); MS m/e (ES$^+$): 452.1 (100%, M$^+$+H); Analysis calculated for C$_{29}$H$_{29}$N$_3$O$_2$: C, 77.14; H, 6.47; N, 9.30%. Found: C, 76.91; H, 6.39; N, 9.26%.

EXAMPLE 20

3-(1H-Indol-3-yl)-2-methyl-N-(1-phenyl-ethyl)-2-[(1H-pyrrol-2-ylmethyl)-amino]-propionamide, (R-(R*,S*)]

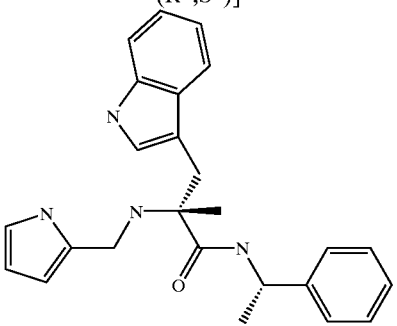

To a stirred solution of 2-pyrrolecarboxaldehyde (71 mg, 0.75 mmol) in 1,2-dichloroethane (10 mL) was added 2-amino-3-(1H-indol-3-yl)-2-methyl-N-(1-phenyl-ethyl)-propionamide (161 mg, 0.5 mmol) followed by sodium triacetoxyborohydride (424 mg, 2 mmol). After stirring over night at room temperature the reaction was cautiously quenched with saturated NaHCO$_3$ (50 mL) and extracted with CH$_2$Cl$_2$ (2×50 mL). The combined organic phases were dried (MgSO$_4$) and the solvent was removed under reduced pressure. The residue was purified by chromatography on normal phase silica using 40% EtOAc in heptane as eluent. Crystallization from ether/heptane gave pure product (50 mg, 25%); mp 123–133° C.; [α]$_D^{23}$=(c=1, MeOH); IR (film): 3314, 2976, 2926, 2852, 1651, 1511, 1455, 909, 736 cm$^{-1}$; NMR (CDCl$_3$): δ1.41 (3H, d, J=6.8 Hz); 1.45 (3H, s); 3.14 (1H, d, J=14.4 Hz); 3.29 (1H, d, J=14.4 Hz); 3.70 (1H, d, J=13.1 Hz); 3.76 (1H, d, J=12.9 Hz); 5.02–5.10 (1H, m); 5.97 (1H, s); 6.07–6.09 (1H, m); 6.58–6.60 (1H, m); 6.74 (1H, d, J=2.2 Hz); 7.10–7.35 (8H, m); 7.41 (1H d, J=7.6 Hz); 7.65 (1H, d, J=7.8 Hz); 7.89 (2H, s); MS m/e (ES$^+$): 423.2 (20%, M$^+$+Na); 402.2 (30%); 401.2 (100%, M$^+$+H); 322.2 (40%); Analysis calculated for C$_{25}$H$_{28}$N$_4$O: C, 74.97; H, 7.05; N, 13.99%. Found: C, 74.83; H, 7.05; N, 13.95%.

EXAMPLE 21

3-(1H-Indol-3-yl)-2-methyl-N-(1-phenyl-ethyl)-2-[(2H-pyrazol-3-ylmethyl)-amino]-propionamide, [R-(R*,S*)]

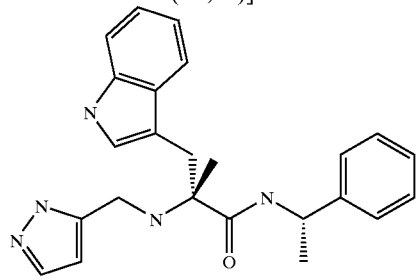

To a stirred solution of pyrazole-3-carboxaldehyde (96 mg, 1 mmol, supplied as dimer) in pyridine (10 mL) was added 2-amino-3-(1H-indol-3-yl)-2-methyl-N-(1-phenyl-ethyl)-propionamide (161 mg, 0.5 mmol) followed by sodium triacetoxyborohydride (848 mg, 4 mmol). After stirring over night at room temperature another portion of sodium triacetoxyborohydride (424 mg, 2 mmol) was added. After stirring over night at room temperature the pyridine was removed under reduced pressure. The residue was taken up in CH$_2$Cl$_2$ (100 mL) and saturated NaHCO$_3$. The aqueous phase was extracted with CH$_2$Cl$_2$ (100 mL). The combined organic phases were washed with brine (50 mL), dried (MgSO$_4$), and the solvent was removed under reduced pressure. The residue was initially purified by chromatography on normal phase silica using 95% EtOAc in heptane as eluent. The solvent was removed under reduced pressure and the residue was dissolved in aqueous acetonitrile and acidified using formic acid. Purification by chromatography on reverse phase silica using 25% CH$_3$CN in H$_2$O (0.1% formic acid in mobile phases) as eluent gave pure product. The solvent was removed under reduced pressure and the residue was suspended between EtOAc and saturated NaHCO$_3$. The EtOAc was dried (MgSO$_4$) and the solvent was removed under reduced pressure to give pure product as a glass (20 mg, 10%); IR (film): 3260, 3059, 2979, 2927, 1651, 1515, 1456, 1374, 1266, 1105, 1048, 1011, 932, 741 cm$^{-1}$; NMR (DMSO-d$_6$): δ1.22 (3H, s); 1.35 (3H, d, J=6.8 Hz); 2.26 (1H, s); 2.96–3.05 (2H, m); 3.50–3.75 (2H, m); 4.93 (1H, s); 6.10 (1H, s); 6.89–6.93 (2H, m); 7.00–7.04 (1H, m); 7.18–7.32 (6H, m); 7.35 (0.5H, s); 7.52 (1H, d, J=7.8 Hz); 7.60 (0.5H, s); 8.05–8.20 (1H, m); 10.82 (1H, s); 12.52 (0.5H, s); 12.73 (0.5H, s); MS m/e (ES$^+$): 424.1 (27%); 402.1 (100%, M$^+$+H).

EXAMPLE 22

2-(3-Benzofuran-2-ylmethyl-ureido)-3-(1H-indol-3-yl)-2-methyl-N-(1-phenyl-ethyl)-propionamide, [R-(R*,S*)]

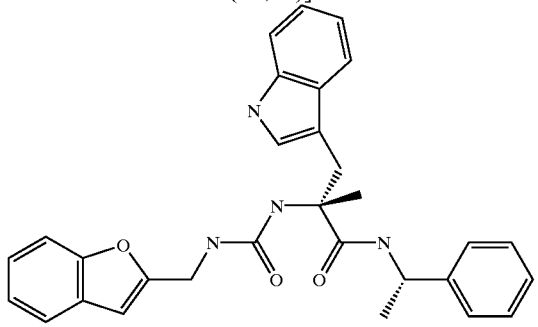

Step 1

To a stirred solution of potassium hydroxide (6.6 g, 100 mmol, 85%) and hydroxylamine (3.66, 52.5 mmol) in EtOH (100 mL, 95%) and water (100 mL) was added 2-benzofurancarboxaldehyde (7.34 g, 50 mmol). Stirred for 48 h before removing the EtOH under reduced pressure. The aqueous phase was saturated with NaCl and then extracted with EtOAc (2×300 mL). The combined organic phases were dried (MgSO$_4$) and the solvent removed under reduced pressure. Crystallization from ether gave pure oxime (7.2 g, 89%). To an ice-cold solution of the oxime (3.22 g, 20 mmol) in THF (150 mL, anhydrous) was added dropwise a solution of lithium aluminum hydride (20 mL, 20 mmol, 1M in THF) under an atmosphere of nitrogen. Reaction mixture allowed to reach room temperature and stirred over night. Reaction mixture cautiously quenched using water. Added 5N NaOH, and aqueous phase extracted with EtOAc (2×100 mL). The combined organic layers were washed with brine, dried (MgSO$_4$), and the solvent was removed under reduced pressure. The residue was purified by chromatography on normal phase silica using EtOAc as eluent to give intermediate IX (1.75 g, 59%).

Step 2

A solution of the armine prepared in step 1 (1.358 g, 9.23 mmol) and pyridine (1.46, 18.5 mmol) in CH$_2$Cl$_2$ (20 mL, anhydrous) was added dropwise over 20 min to an ice cooled solution of triphosgene (0.96, 3.23 mmol). Reaction mixture allowed to reach room temperature. After 30 min, solvent removed under reduced pressure. The residue was taken up in EtOAc, filtered, and solvent removed under reduced pressure to give isocyanate (1.60 g, 100%). IR (film): 2256 cm$^-$. A solution of the isocyanate (1.038 g, 6 mmol) and 2-amino-3-(1H-indol-3-yl)-2-methyl-N-(1-phenyl-ethyl)-propionamide (1.926 g, 6 mmol) in THF (50 mL, anhydrous) was stirred at room temperature for 5 min. The solvent was removed under reduced pressure. The residue was taken up in EtOAc and washed with 1N HCl (3×20 mL), saturated Na$_2$CO$_3$ (30 mL), brine (30 mL), dried MgSO$_4$, and the solvent removed under reduced pressure. The residue was purified by chromatography on reverse phase silica using 65% MeOH in H$_2$O as eluent. Crystallization from MeOH/H$_2$O gave pure product (1.35 g, 45%). mp 176–178 °C.; $[\alpha]_D^{22}$=+30.4° (c=1, MeOH); IR (film): 3321, 3058, 2978, 2932, 1645, 1558, 1506, 1495, 1445, 1253, 741 cm$^{-1}$; NMR (CDCl$_3$): δ1.35 (3H, d, J=6.8 Hz); 1.61 (3H, s); 3.20 (1H, d, J=14.6 Hz); 3.54 (1H, d, J=14.6 Hz); 4.38 (1H, d.d, J=16.0 and 6.0 Hz); 4.45 (1H, d.d, J=15.9 and 6.1 Hz); 4.78 (1H, t, J=6.0 Hz); 4.97 (1H, s); 4.95–5.05 (1H, m); 6.49 (1H, s); 6.76 (1H, d, J=2.4 Hz); 7.00 (1H, d, J=7.6 Hz); 7.05–7.10 (1H, m); 7.13–7.28 (9H, m); 7.38 (1H, d, J=8.1 Hz); 7.48–7.50 (1H, m); 7.57 (1H, d, J=7.8 Hz); 7.74 (1H, s); MS m/e (APCI$^+$): 496.3 (30%); 495.2 (100%, M$^+$+H); 477.2 (7%); 374.2 (7%); 322.3 (17%); Analysis calculated for C$_{30}$H$_{30}$N$_4$O$_3$: C, 72.85; H, 6.11; N, 11.32%. Found: C, 73.09; H, 6.08; N, 11.35%.

EXAMPLES 23 TO 191

(See Table 2 Below)

Intermediate VII, N-[b]benzofuranylmethyl-R-α-methyl-tryptophan-N-carboxyanhydride Intermediate I (5.23 g, 15 mmol) was stirred in toluene (50 mL) under nitrogen and heated to 55° C. Phosgene in toluene (37 mL, 75 mmol) was added in one portion and as soon as the temperature had returned to 55° C. dry THF (150 mL) was added rapidly dropwise. Stirring was continued for 30 min and the reaction was then cooled, the solvent removed in vacuo. The residue taken up in ether (50 mL) and filtered and evaporated to dryness several times until a solid was obtained; (6.15 g, 100%); IR (film): 3418, 1844, 1771, 1455, 1397, 1251, 986, 746 cm$^{-1}$; NMR (CDCl$_3$) 1.64 (3H, s); 3.31 (1H, d, J=15 Hz); 3.44 (1H, d, J=15 Hz); 4.45 (1H, d J=16Hz); 4.81 (1H, d, J=16 Hz); 6.77 (1 H, s); 6.94 (1H, d J=2.8 Hz); 7.14–7.58 (8H, m); 8.16(1H, s).

General procedure for array synthesis of Examples 23 to 191

A 40-well DTI synthesizer rack (U.S. Pat. No. 5,324,483) was loaded with 40 DTI vials (12 mL). To each vial 0.15–0.21 mmol of an amine or amine HCl salt was added. The rack was placed in a Cyberlab Liquid Handling Robot and to each vial 0.10 mmol N-[b]benzofuranylmethyl-R-α-methyl-tryptophan-N-carboxyanhydride (0.227 M in THF) was added. To those vials that contained amine HCl salts, 0.15 mmol triethylamine (0.254 M in THF) was added, in order to liberate the free amines. THF was then added to each vial to make up the total volume to 3 mL. The vials were placed in a 40-well DTI synthesizer equipped with a heating block, 40 condensers and a nitrogen manifold. The synthesizer was kept under a continuous flow of nitrogen and was shaken at 65° C. on an orbital shaker for 2 days. The reactions were monitored by TLC (10% CH$_3$CN in CH$_2$Cl$_2$). The vials in which the reaction had gone to completion were taken out. To the remaining vials CH$_3$CN (2 mL) was added each and these were shaken at 85° C. for 19 h. The vials in which the reaction had gone to completion were taken out. To the remaining vials pyridine (1 mL) was added each and these were shaken at 105° C. for 6 h followed by 15 h at 65° C. The vials were then concentrated at reduced pressure in a Speedvac and were purified by chromatography over a 12 mL LC-Si SPE cartridge containing 2 g silica (elution with 10% CH$_3$CN in CH$_2$Cl$_2$ followed by 20% CH$_3$CN in CH$_2$Cl$_2$, 5% methanol in CH$_2$Cl$_2$, 10% methanol in CH$_2$Cl$_2$, 20% methanol in CH$_2$Cl$_2$ and 50% methanol in CH$_2$Cl$_2$, depending on the polarity of the products). The products were subjected to LC-MS. Those products which did contain the desired molecular ion, but were not sufficiently pure (typically <85%) were further purified by prep HPLC on a C18 reversed phase preparative column. The HPLC-purified products were re-analyzed by LC-MS to determine the purity. The 40 final products were analyzed by $^1$H NMR.

EXAMPLES 192 TO 308

(See Table 3 Below)

Intermediate II

Step 1

The compound was prepared as described for Intermediate I, step 1; (20.5 g, 59%); NMR (CDCl$_3$) 2.10 (1H, s); 3.18 (2H, m); 3.60 (3H, s); 3.80–4.00 (2H, m); 6.43 (1H, s); 7.03–7.60 (9H, m); 8.00 (1H, s).

Step 2

The compound was prepared as described for Intermediate I; (7.02 g, 85%); NMR (DMSO-D$_6$) 3.01–3.12 (2H, m); 3.52 (1H, m); 3.80 (1H, d, J=15 Hz); 3.80 (1H, d, J=14.8 Hz); 6.61 (1H, s); 6.93–7.54 (9H, m); 10.82 (1H, s).

General procedure for array synthesis of Examples 192 to 308 (see Table 4 below)

A 40-well DTI synthesizer rack was loaded with 40 Kimble vials (10 mL). To each vial approximately 0.34 g (0.10 mmol) N-[b]benzofuranylmethyl-R-tryptophan was added followed by 1.5 equivalent of an amine or amine HCl salt. The rack was placed in a Cyberlab Liquid Handling Robot and to each vial 1.0 equivalent of HBTU (0.4 M in DMF) was added followed by 1.5 equivalent of diisopropylethylamine (0.5 M in DMF). To those vials, which contained amine HCl salts, an additional equivalent of diisopropylethylamine was added. DMF was added to make the total volume up to 1.5 mL. The vials were capped and the rack was shaken on an orbital shaker at room temperature for 3 h. To each vial, water (1 mL) was added and the mixtures were purified on 3 mL LC-18 reversed phase SPE cartridges containing 500 mg of sorbent, using an ASPEC XL4 robot. The cartridges were conditioned with methanol (4 mL) followed by methanol/water 1:1 (4 mL). Water (1 mL) was loaded onto the cartridges and the crude reaction mixtures were loaded into the water layer. The cartridges were washed with water (4 mL) and methanol/water 1:1 (4 mL) and were eluted with methanol (4 mL). The methanol fractions were concentrated and the products were subjected to LC-MS. Those products which did contain the desired molecular ion, but were not sufficiently pure (typically <90%) were further purified by prep HPLC on a C18 reversed phase preparative column. The HPLC-purified products were re-analyzed by LC-MS to determine the purity. The 40 final products were analyzed by $^1$H NMR.

EXAMPLES 309 TO 405

See Table 5 Below

General procedure for array synthesis of Examples 309 to 405

The N-terminal derivatives where prepared from 2-amino-3-(1H-indol-3-yl)-2-methyl-N-(1-phenyl-ethyl)-propionamide, prepared as described by Boyle S., et al., Bioorg. Med. Chem. 2:357 (1994), or from 2-amino-3-(1H-indol-3-yl)-N-(1-phenyl-ethyl)-propionamide (Intermediate V), using the procedure of Siegel M. G., et al., Tet. Lett. 38: 3357, (1997).

Because the compounds are potent ligands to the NK$_1$ receptor, they are effective at displacing substance P at that position, and therefore are useful for treating biological conditions otherwise mediated by substance P. Accordingly, compounds capable of antagonising the effects of substance P at NK$_1$ receptors will be useful in treating or preventing a variety of brain disorders including pain (inflammatory, surgical and neuropathic), anxiety, panic, depression, schizophrenia, neuralgia, stress, sexual dysfunction, bipolar disorders, movement disorders, cognitive disorders, and addiction disorders; inflammatory diseases such as arthritis, asthma, and psoriasis; gastrointestinal disorders including colitis, Crohn's disease, irritable bowel syndrome and satiety; allergic responses such as eczema and rhinitis; vascular disorders such as angina and migraine; neuropathological disorders including scleroderma and emesis. The compounds of the invention, NK$_1$ receptor antagonists, are also useful as anti-angiogenic agents, for the treatment of conditions associated with aberrant neovascularization such as rheumatoid arthritis, atherosclerosis and tumour cell growth. They will also be useful as agents for imaging NK$_1$ receptors in vivo in conditions such as ulcerative colitis and Crohn's disease.

The compounds of the present invention are highly selective and competitive antagonists of the NK$_1$ receptor. They have been evaluated in an NK$_1$-receptor binding assay which is described below.

Human lymphoma IM9 cells were grown in RPMI 1640 culture medium supplemented with 10% fetal calf serum and 2 mM glutamine and maintained under an atmosphere of 5% $CO_2$. Cells were passaged every 3–4 days by reseeding to a concentration of $4-8\times10^6/40$ ml per 175 $cm^2$ flask. Cells were harvested for experiments by centrifugation at 1000 g for 3 min. Pelleted cells were washed once by resuspension into assay buffer (50 mM Tris HCl pH 7.4, 3 mM $MnCl_2$, 0.02% BSA, 40 mg/mL bacitracin, 2 mg/mL chymostatin, 2 mM phosphoramidon, 4 mg/mL leupeptin) and repeating the centrifugation step before resuspending at a concentration of $2.5\times10^6$ cells/mL assay buffer. Cells (200 ml) were incubated with [$^{125}$I]Bolton-Hunter substance P (0.05–0.1 nM) in the presence and absence of varying concentrations of test compounds for 50 min at 21° C. Non-specific binding (10% of the total binding observed under these conditions) was defined by 1 mM [Sar$^9$, Met($0_2$)$^{11}$] substance P. Reactions were terminated by rapid filtration under vacuum onto GF\C filters presoaked in 0.2% PEI for 1–2 h, using a Brandel cell harvester. Filters were washed with 6×1 ml ice-cold Tris HCl (50 mM, pH 7.4) and radioactivity bound determined using a gamma couter. Results were analyzed using iterative curve fitting procedures in RS1 or Graphpad Inplot.

TABLE 1

In Vitro Human NK$_1$ Receptor Binding Assay

| Example No | NK$_1$ binding IC$_{50}$ (nM) |
| --- | --- |
| 1 | 591 |
| 2 | 23 |
| 3 | 6 |
| 4 | 1213 |
| 5 | 295 |
| 6 | 0.7 |
| 7 | 3.3 |
| 8 | 27 |
| 9 | 112 |
| 10 | 51 |
| 11 | 46 |
| 12 | 14 |
| 13 | 35 |
| 14 | 4.7 |
| 15 | >10,000 |
| 16 | 9.1 |
| 17 | 344 |
| 18 | 4.4 |
| 19 | 58 |
| 20 | 815 |
| 21 | 1808 |
| 22 | 2.9 |

Similar binding data are presented in Tables 2–5 for specific invention compounds.

TABLE 2

Examples 23–191

| Ex. | Name | Yield (mg) | Mol. ion | Lcms % purity | Lcms Rt (min) | IC$_{50}$ (nM) hNK$_1$ |
| --- | --- | --- | --- | --- | --- | --- |
| 23 | 2-[(Benzofuran-2-ylmethyl)-amino]-3-(1H-indol-3-yl)-2-methyl-N-pyridin-2ylmethyl-propionamide | 19,7 | 439 | 100 | 3,07 | 1284 |

TABLE 2-continued

Examples 23–191

| Ex. | Name | Yield (mg) | Mol. ion | Icms % purity | Icms Rt (min) | IC$_{50}$ (nM) hNK$_1$ |
|---|---|---|---|---|---|---|
| 24 | 2-[(Benzofuran-2-ylmethyl)-amino]-3-(1H-indol-3-yl)-2-methyl-N-pyridin-3-ylmethyl-propionamide | 23,5 | 439 | 100 | 2,6 | 547 |
| 25 | 2-[(Benzofuran-2-ylmethyl)-amino]-3-(1H-indol-3-yl)-2-methyl-N-pyridin-4-ylmethyl-propionamide | 41,9 | 439 | 100 | 2,6 | 131 |
| 26 | 2-[(Benzofuran-2-ylmethyl)-amino]-N-cyclohexyl-3-(1H-indol-3-yl)-2-methyl-propionamide | 18,4 | 430 | 100 | 5,2 | 1011 |
| 27 | 2-[(Benzofuran-2-ylmethyl)-amino]-N-cyclohexylmethyl-3-(1H-indol-3-yl)-2-methyl-propionamide | 24,6 | 444 | 100 | 5,81 | 311 |
| 28 | 2-[(Benzofuran-2-ylmethyl)-amino]-N-benzyl-3-(1H-indol-3-yl)-2-methyl-propionamide | 26,5 | 438 | 97 | 4,6 | 44 |
| 29 | 2-[(Benzofuran-2-ylmethyl)-amino]-N-(2-hydroxy-1-phenyl-ethyl)-3-(1H-indol-3-yl)-2-methyl-propionamide | 43,1 | 468 | 82 | 3,22 | 7 |
| 30 | 2-[(Benzofuran-2-ylmethyl)-amino]-N-[1-(4-chloro-phenyl)-ethyl]-3-(1H-indol-3-yl)-2-methyl-propionamide | 43,3 | 486 | 74 | 5,81 | 17 |
| 31 | 2-[(Benzofuran-2-ylmethyl)amino]-3-(1H-indol-3-yl)-2-methyl-N-(1-naphthalen-1-yl-ethyl)-propionamide | 29,4 | 502 | 100 | 6,05 | >10,000 |
| 32 | 2-[(Benzofuran-2-ylmethyl)-amino]-3-(1H-indol-3-yl)-2-methyl-N-(1-naphthalen-1-yl-ethyl)-propionamide | 40,1 | 502 | 100 | 5,96 | >10,000 |
| 33 | 2-[(Benzofuran-2-ylmethyl)-amino]-N-[1-(4-fluoro-phenyl)-ethyl]-3-(1H-indol-3-yl)-2-methyl-propionamide | 44,4 | 470 | 100 | 5,11 | 9 |
| 34 | 2-[(Benzofuran-2-ylmethyl)-amino]-3-(1H-indol-3-yl)-2-methyl-N-[1-(4-nitro-phenyl)-ethyl]-propionamide | 23,8 | 497 | 100 | 5,07 | 14 |
| 35 | 2-[(Benzofuran-2-ylmethyl)-amino]-3-(1H-indol-3-yl)-N-[1-(4-methoxy-phenyl)-ethyl]-2-methyl-propionamide | 27,8 | 482 | 100 | 4,86 | 31 |
| 36 | N-[1-(2-Amino-phenyl)-ethyl]-2-[(benzofuran-2-ylmethyl)-amino]-3-(1H-indol-3-yl)-2-methyl-propionamide | 25,8 | 467 | 100 | 4,45 | 1620 |
| 37 | N-[1-(3-Amino-phenyl)-ethyl]-2-[(benzofuran-2-ylmethyl)-amino]-3-(1H-indol-3-yl)-2-methyl-propionamide | 25,5 | 467 | 100 | 3,7 | 364 |
| 38 | N-[1-(4-Amino-phenyl)-ethyl]-2-[(benzofuran-2-ylmethyl)-amino]-3-(1H-indol-3-yl)-2-methyl-propionamide | 22,5 | 467 | 100 | 3,2 | 141 |
| 39 | 2-[(Benzofuran-2-ylmethyl)-amino]-N-[1-(4-dimethylamino-phenyl)-ethyl]-3-(1H-indol-3-yl)-2-methyl-propionamide | 48,3 | 495 | 100 | 5,26 | 863 |
| 40 | 2-[(Benzofuran-2-ylmethyl)-amino)-N-[1-(3-dimethylamino-phenyl)-ethyl]-3-(1H-indol-3-yl)-2-methyl-propionamide | 25,3 | 495 | 100 | 5,18 | 1065 |
| 41 | 2-[(Benzofuran-2-ylmethyl)-amino]-3-(1H-indol-3-yl)-2-methyl-N-(1-thiophen-3-yl-ethyl)-propionamide | 17 | 458 | 100 | 4,89 | 19 |
| 42 | 2-[(Benzofuran-2-ylmethyl)-amino]-3-(1H-indol-3-yl)-2-methyl-N-(1-phenyl-ethyl)-propionamide | 34,5 | 452 | 100 | 5,06 | 261 |
| 43 | 2-{[2-[(Benzofuran-2-ylmethyl)-amino]-3-(1H-indol-3-yl)-2-methyl-propionylamino]-methyl}-4-hydroxy-pyrimidine-5-carboxylic acid | 28,5 | 500 | 10 | 9,4 | 3613 |
| 44 | 2-[(Benzofuran-2-ylmethyl)-amino]-3-(1H-indol-3-yl)-2-methyl-N-(1-pyridin-3-yl-ethyl)-propionamide | 43,9 | 453 | 90 | 6,85 | 151 |

TABLE 2-continued

Examples 23–191

| Ex. | Name | Yield (mg) | Mol. ion | lcms % purity | lcms Rt (min) | IC$_{50}$ (nM) hNK$_1$ |
|---|---|---|---|---|---|---|
| 45 | 2-[(Benzofuran-2-ylmethyl)-amino]-3-(1H-indol-3-yl)-2-methyl-N-(2-pyridin-2-yl-ethyl)-propionamide | 43 | 453 | 95 | 7,15 | 913 |
| 46 | 2-[(Benzofuran-2-ylmethyl)-amino]-N-(2,4-dichloro-benzyl)-3-(1H-indol-3-yl)-2-methyl-propionamide | 49,5 | 506 | 95 | 10,2 | 1560 |
| 47 | 2-[(Benzofuran-2-ylmethyl)-amino]-3-(1H-indol-3-yl)-2-methyl-N-[2-(4-sulfamoyl-phenyl)-ethyl]-propionamide | 52,6 | 531 | 95 | 6,66 | 7616 |
| 48 | N-(2-Amino-6-fluoro-benzyl)-2-[(benzofuran-2-ylmethyl)-amino]-3-(1H-indol-3-yl)-2-methyl-propionamide | 49,3 | 471 | 95 | 8,68 | 6423 |
| 49 | 2-[(Benzofuran-2-ylmethyl)-amino]-N (2-hydroxy-cyclohexylmethyl)-3-(1H-indol-3-yl)-2-methyl-propionamide | 4,9 | 460 | 95 | 8,22 | 1550 |
| 50 | 2-[(Benzofuran-2-ylmethyl)-amino]-N-(2-hydroxy-2-phenyl-ethyl)-3-(1H-indol-3-yl)-2-methyl-propionamide | 44,4 | 468 | 95 | 7,6 | 1333 |
| 51 | 2-[(Benzofuran-2-ylmethyl)-amino]-N-(3,5-bis-trifluoromethyl-benzyl)-3-(1H-indol-3-yl)-2-methyl-propionamide | 31,1 | 574 | 95 | 10,32 | 179 |
| 52 | 2-[(Benzofuran-2-ylmethyl)-amino]-3-(1H-indol-3-yl)-2-methyl-N-[2-(1-methyl-pyrrolidin-2-yl)-ethyl]-propionamide | 39,3 | 459 | 95 | 9,16 | >10,000 |
| 53 | 2-[(Benzofuran-2-ylmethyl)-amino]-3-(1H-indol-3-yl)-2-methyl-N-phenethyl-propionamide | 42 | 452 | 90 | 8,9 | 262 |
| 54 | 2-[(Benzofuran-2-ylmethyl)-amino]-N-(2,3-dimethyl-benzyl)-3-(1H-indol-3-yl)-2-methyl-propionamide | 23,2 | 466 | 90 | 9,95 | 834 |
| 55 | 2-[(Benzofuran-2-ylmethyl)-amino]-3-(1H-indol-3-yl)-N-(3-methoxy-benzyl)-2-methyl-propionamide | 49 | 468 | 95 | 8,95 | 643 |
| 56 | N-[2-(4-Amino-phenyl)-ethyl]-2-[(benzofuran-2-ylmethyl)-amino]-3-(1H-indol-3-yl)-2-methyl-propionamide | 49 | 467 | 90 | 7,31 | 3228 |
| 57 | 2-[(Benzofuran-2-ylmethyl)-amino]-N-(1-cyclohexyl-ethyl)-3-(1H-indol-3-yl)-2-methyl-propionamide | 7 | 458 | 95 | 10,73 | 290 |
| 58 | 2-[(Benzofuran-2-ylmethyl)-amino]-3-(1H-indol-3-yl)-2-methyl-N-(1-p-tolyl-ethyl)-propionamide | 27 | 466 | 90 | 9,95 | 624 |
| 59 | 2-[(Benzofuran-2-ylmethyl)-amino]-3-(1H-indol-3-yl)-2-methyl-N-(3-trifluoromethoxy-benzyl)-propionamide | 46 | 522 | 90 | 9,61 | >10,000 |
| 60 | 2-[(Benzofuran-2-ylmethyl)-amino]-N-(4-dimethylamino-benzyl)-3-(1H-indol-3-yl)-2-methyl-propionamide | 10 | 481 | 90 | 9,16 | 964 |
| 61 | 2-[(Benzofuran-2-ylmethyl)-amino]-N-(4-fluoro-benzyl)-3-(1H-indol-3-yl)-2-methyl-propionamide | 48,4 | 456 | 90 | 8,74 | 61 |
| 62 | N-(4-Amino-benzyl)-2-[(benzofuran-2-ylmethyl)-amino]-3-(1H-indol-3-yl)-2-methyl-propionamide | 32,3 | 453 | 90 | 7,29 | 837 |
| 63 | 2-[(Benzofuran-2-ylmethyl)-amino]-3-(1H-indol-3-yl)-2-methyl-N-(1-phenyl-propyl)-propionamide | 21,6 | 466 | 75 | 9,95 | 58 |
| 64 | 2-[(Benzofuran-2-ylmethyl)-amino]-N-(4-chloro-benzyl)-3-(1H-indol-3-yl)-2-methyl-propionamide | 50,2 | 472 | 90 | 9,3 | 76 |
| 65 | 2-[(Benzofuran-2-ylmethyl)-amino]-N-(2-bromo-benzyl)-3-(1H-indol-3-yl)-2-methyl-propionamide | 43,9 | 516 | 90 | 9,43 | 700 |

TABLE 2-continued

Examples 23–191

| Ex. | Name | Yield (mg) | Mol. ion | Icms % purity | Icms Rt (min) | IC$_{50}$ (nM) hNK$_1$ |
|---|---|---|---|---|---|---|
| 66 | 2-[(Benzofuran-2-ylmethyl)-amino]-3-(1H-indol-3-yl)-2-methyl-N-(4-trifluoromethoxy-benzyl)-propionamide | 40,9 | 522 | 90 | 9,69 | 3444 |
| 67 | 2-[(Benzofuran-2-ylmethyl)-amino]-3-(1H-indol-3-yl)-2-methyl-N-(1-p-tolyl-ethyl)-propionamide | 18,8 | 466 | 92 | 9,94 | 3 |
| 68 | 2-[(Benzofuran-2-ylmethyl)-amino]-3-(1H-indol-3-yl)-N-(4-methoxy-benzyl)-2-methyl-propionamide | 48,9 | 468 | 90 | 8,41 | 312 |
| 69 | 2-[(Benzofuran-2-ylmethyl)-amino]-3-(1H-indol-3-yl)-2-methyl-N-(1-pyridin-2-yl-ethyl)-propionamide | 44,7 | 453 | 95 | 7,68 | 12 |
| 70 | 2-[(Benzofuran-2-ylmethyl)-amino]-N-(2-cyclohexyl-ethyl)-3-(1H-indol-3-yl)-2-methyl-propionamide | 38,1 | 458 | 90 | 10,45 | 216 |
| 71 | 2-[(Benzofuran-2-ylmethyl)-amino]-3-(1H-indol-3-yl)-2-methyl-N-(4-methyl-benzyl)-propionamide | 40 | 452 | 90 | 9,13 | 144 |
| 72 | 2-[(Benzofuran-2-ylmethyl)-amino]-N-(3-bromo-benzyl)-3-(1H-indol-3-yl)-2-methyl-propionamide | 43,2 | 516 | 90 | 9,43 | 18 |
| 73 | 2-[(Benzofuran-2-ylmethyl)-amino]-N-(2-hydroxy-2-phenyl-ethyl)-3-(1H-indol-3-yl)-2-methyl-propionamide | 35,2 | 468 | 90 | 7,56 | 1229 |
| 74 | 2-[(Benzofuran-2-ylmethyl)-amino]-3-(1H-indol-3-yl)-2-methyl-N-(3-trifluoromethyl-benzyl)-propionamide | 16 | 506 | 90 | 9,51 | 12 |
| 75 | 2-[(Benzofuran-2-ylmethyl)-amino]-N-(1,2-diphenyl-ethyl)-3-(1H-indol-3-yl)-2-methyl-propionamide | 48,1 | 528 | 100 | 7,06 | >10,000 |
| 76 | 2-[(Benzofuran-2-ylmethyl)-amino]-3-(1H-indol-3-yl)-2-methyl-N-(2-methylamino-ethyl)-propionamide | 28 | 405 | 50 | 2,01 | 3696 |
| 77 | 2-[(Benzofuran-2-ylmethyl)-amino]-N-(3-chloro-benzyl)-3-(1H-indol-3-yl)-2-methyl-propionamide | 20 | 472 | 100 | 6,19 | 17 |
| 78 | 2-[(Benzofuran-2-ylmethyl)-amino]-3-(1H-indol-3-yl)-2-methyl-N-(1,3,5-triaza-tricyclo[3.3.1.1>3,7]-dec-7-yl)-propionamide | 9,2 | 485 | 50 | 1,93 | >10,000 |
| 79 | 2-[(Benzofuran-2-ylmethyl)-amino]-3-(1H-indol-3-yl)-2-methyl-N-[1-methyl-2-(3-trifluoromethyl-phenyl)-ethyl]-propionamide | 30,1 | 534 | 100 | 6,84 | >10,000 |
| 80 | 2-[(Benzofuran-2-ylmethyl)-amino]-3-(1H-indol-3-yl)-2-methyl-N-(2-phenyl-2-pyridin-2-yl-ethyl)-propionamide | 22,4 | 529 | 100 | 5,9 | >10,000 |
| 81 | 4-{[2-[(Benzofuran-2-ylmethyl)-amino]-3-(1H-indol-3-yl)-2-methyl-propionylamino]-methyl}-3-methoxy-benzoic acid methyl ester | 37,4 | 526 | 100 | 5,59 | >10,000 |
| 82 | 2-[(Benzofuran-2-ylmethyl)-amino]-3(1H-indol-3-yl)-2-methyl-N-(1,2,2-trimethyl-propyl)-propionamide | 8,5 | 432 | 100 | 6,51 | 1144 |
| 83 | 2-[(Benzofuran-2-ylmethyl)-amino]-N-(2-dimethylamino-ethyl)-3-(1H-indol-3-yl)-2-methyl-propionamide | 27,5 | 419 | 100 | 3,61 | 3519 |
| 84 | 4-[2-[(Benzofuran-2-ylmethyl)-amino]-3-(1H-indol-3-yl)-2-methyl-propionylamino]-3-(4-chloro-phenyl)-butyric acid | 5 | 544 | 100 | 1,62 | >10,000 |
| 85 | 2-[(Benzofuran-2-ylmethyl)-amino]-3-(1H-indol-3-y])-2-methyl-N-(3-oxo-2,3-dihydro-1H-isoindol-1-yl)-propionamide | 11,3 | 479 | 100 | 3,73 | 2443 |
| 86 | 2-[(Benzofuran-2-ylmethyl)-amino]-3-(1H-indol-3-yl)-2-methyl-N-[2-(2-oxo-imidazolidin-1-yl)-ethyl]-propionamide | 24,7 | 460 | 100 | 2,58 | >10,000 |

TABLE 2-continued

Examples 23–191

| Ex. | Name | Yield (mg) | Mol. ion | Icms % purity | Icms Rt (min) | IC$_{50}$ (nM) hNK$_1$ |
|---|---|---|---|---|---|---|
| 87 | 2-[(Benzofuran-2-ylmethyl)-amino]-3-(1H-indol-3-yl)-2-methyl-N-[3-(4-pyridin-2-yl-piperazin-1-yl)-propyl]-propionamide | 38,9 | 551 | 100 | 4,63 | >10,000 |
| 88 | 2-[(Benzofuran-2-ylmethyl)-amino]-N-[4-(2,6-dimethyl-piperidin-1-yl)-butyl]-3-(1H-indol-3-yl)-2-methyl-propionamide | 33,4 | 515 | 100 | 4,58 | >10,000 |
| 89 | 2-[(Benzofuran-2-ylmethyl)-amino]-3-(1H-indol-3-yl)-2-methyl-N-(1-piperidin-1-ylmethyl-cyclohexyl)-propionamide | 21,2 | 527 | 100 | 8,88 | 6735 |
| 90 | 2-[(Benzofuran-2-ylmethyl)-amino]-N-[2-(1H-imidazol-4-yl)-1-methyl-ethyl]-3-(1H-indol-3-yl)-2-methyl-propionamide | 8,2 | 456 | 100 | 3,07 | >10,000 |
| 91 | 2-[(Benzofuran-2-ylmethyl)-amino]-3-(lH-indol-3-yl)-2-methyl-N-[3-(2-oxo-pyrrolidin-]-yl)-propyl]-propionamide | 28,1 | 473 | 100 | 3,07 | >10,000 |
| 92 | 2-[(Benzofuran-2-ylmethyl)-amino]-3-(1H-indol-3-yl)-N-isopropyl-2-methyl-propionamide | 17,6 | 390 | 100 | 4,96 | 2285 |
| 93 | 2-[(Benzofuran-2-ylmethyl)-amino]-3-(1H-indol-3-yl)-2-methyl-N-[1-methyl-2-(2-oxo-pyrrolidin-1-yl)-ethyl]-propionamide | 17,6 | 473 | 100 | 3,29 | >10,000 |
| 94 | 2-[(Benzofuran-2-ylmethyl)-amino]-N-[4-(2,5-dimethyl-pyrrolidin-1-yl)-butyl]-3-(1H-indol-3-yl)-2-methyl-propionamide | 30,6 | 501 | 100 | 3,27 | >10,000 |
| 95 | N-[2-(5-Amino-1H-imidazol-4-yl)-2-oxo-ethyl]-2-[(benzofuran-2-ylmethyl)-amino]-3-(1H-indol-3-yl)-2-methyl-propionamide | 19,2 | 471 | 100 | 3,5 | >10,000 |
| 96 | 2-[(Benzofuran-2-ylmethyl)-amino]-3-(1H-indol-3-yl)-2-methyl-N-[2-(2-oxo-oxazolidin-3-yl)-ethyl]-propionamide | 4,6 | 461 | 100 | 2,26 | >10,000 |
| 97 | 2-[(Benzofuran-2-ylmethyl)-amino]-N-[2-(1H-imidazol-4-yl)-ethyl]-3-(1H-indol-3-yl)-2-methyl-propionamide | 30 | 442 | 100 | 2,26 | >10,000 |
| 98 | 2-[(Benzofuran-2-ylmethyl)-amino]-N-(2,2-diphenyl-ethyl)-3-(1H-indol-3-yl)-2-methyl-propionamide | 34,5 | 528 | 100 | 2,26 | >10,000 |
| 99 | 2-[(Benzofuran-2-ylmethyl)-amino]-3-(1H-indol-3-yl)-2-methyl-N-[2-(2-oxo-pyrrolidin-1-yl)-ethyl]-propionamide | 17,9 | 459 | 100 | 2,26 | >10,000 |
| 100 | 2-[(Benzofuran-2-ylmethyl)-amino]-3-(1H-indol-3-yl)-2-methyl-N-(5-nitro-furan-2-ylmethyl)-propionamide | 7,2 | 473 | 100 | 2,26 | 390 |
| 101 | 2-[(Benzofuran-2-ylmethyl)-amino]-3-(1H-indol-3-yl)-2-methyl-N-[2-(5-methyl-1H-imidazol-4-yl)-ethyl]-propionamide | 19,4 | 456 | 100 | 2,27 | >10,000 |
| 102 | 2-[(Benzofuran-2-ylmethyl)-amino]-N-[1-(3-dimethylamino-phenyl)-cyclopentylmethyl]-3-(1H-indol-3-yl)-2-methyl-propionamide | 18,9 | 549 | 90 | 8,66 | >10,000 |
| 103 | 2-[(Benzofuran-2-ylmethyl)-amino]-N-(1H-benzoimidazol-2-ylmethyl)-3-(1H-indol-3-yl)-2-methyl-propionamide | 0,4 | 478 | 77 | 0 05 | 74 |
| 104 | 2-[(Benzofuran-2-ylmethyl)-amino]-N-(1-cyclohexyl-ethyl)-3-(1H-indol-3-yl)-2-methyl-propionamide | 8,3 | 458 | 100 | 0 06 | 8 |
| 105 | 2-[(Benzofuran-2-ylmethyl)-amino]-3-(1H-indol-3-yl)-2-methyl-N-(2-phenyl-[1,3-dioxolan-2-ylmethyl)-propionamide | 13,2 | 510 | 69 | 0 05 | >10,000 |

TABLE 2-continued

Examples 23–191

| Ex. | Name | Yield (mg) | Mol. ion | Icms % purity | Icms Rt (min) | IC$_{50}$ (nM) hNK$_1$ |
|---|---|---|---|---|---|---|
| 106 | 2-[(Benzofuran-2-ylmethyl)-amino]-3-(1H-indol-3-yl)-2-methyl-N-(2-methyl-1,2,3,4-tetrahydro-isoquinolin-3-ylmethyl)-propionamide | 5,7 | 507 | 100 | 0 06 | 4630 |
| 107 | 2-[(Benzofuran-2-ylmethyl)-amino]-3-(1H-indol-3-yl)-2-methyl-N-(2-phenyl-cyclopropyl)-propionamide | 14 | 464 | 100 | 0 05 | 4145 |
| 108 | 2-[(Benzofuran-2-ylmethyl)-amino]-3-(1H-indol-3-yl)-2-methyl-N-(1,2,3,4-tetrahydro-isoquinolin-3-ylmethyl)-propionamide | 0,6 | 493 | 100 | 0 05 | 4566 |
| 109 | 2-[(Benzofuran-2-ylmethyl)-amino]-N-(2,5-dichloro-thiophen-3-ymethyl)-3-(1H-indol-3-yl)-2-methyl-propionamide | 30,3 | 512 | 100 | 0 06 | 279 |
| 110 | 2-[(Benzofuran-2-ylmethyl)-amino]-3-(1H-indol-3-yl)-2-methyl-N-(1-phenyl-cyclopropylmethyl)-propionamide | 19,7 | 478 | 100 | 0 05 | 1141 |
| 111 | 2-[(Benzofuran-2-ylmethyl)-amino]-3-(1H-indol-3-yl)-2-methyl-N-(1,2,3,4-tetrahydro-naphthalen-2-yl)-propionamide | 1 | 478 | 100 | 0 08 | >10,000 |
| 112 | 2-[(Benzofuran-2-ylmethyl)-amino]-3-(1H-indol-3-yl)-2-methyl-N-(3-nitro-benzyl)-propionamide | 3 | 483 | 100 | 0 06 | 12 |
| 113 | 2-[(Benzofuran-2-ylmethyl)-amino]-N-indan-2-yl-3-(1H-indol-3-yl)-2-methyl-propionamide | 10,1 | 464 | 100 | 0 05 | 463 |
| 114 | 2-[(Benzofuran-2-ylmethyl)-amino]-3-(1H-indol-3-yl)-2-methyl-N-(1-thiophen-2-yl-propyl)-propionamide | 2,5 | 472 | 90 | 0 05 | 128 |
| 115 | 2-[(Benzofuran-2-ylmethyl)-amino]-N-(2-furan-2-yl-ethyl)-3-(1H-indol-3-yl)-2-methyl-propionamide | 11,5 | 442 | 95 | 0 05 | 154 |
| 116 | 2-[(Benzofuran-2-ylmethyl)-amino]-N-(1-hydroxy-cyclohexylmethyl)-3-(1H-indol-3-yl)-2-methyl-propionamide | 5,6 | 460 | 100 | 0 05 | >10,000 |
| 117 | 2-[(Benzofuran-2-ylmethyl)-amino]-N-(1-furan-2-yl-cyclobutylmethyl)-3-(1H-indol-3-yl)-2-methyl-propionamide | 14,2 | 482 | 100 | 0 06 | >10,000 |
| 118 | 2-[(Benzofuran-2-ylmethyl)-amino]-N-[1-(5-chloro-thiophen-2-yl)-ethyl]-3-(1H-indol-3-yl)-2-methyl-propionamide | 15 | 492 | 100 | 0 06 | 45 |
| 119 | 2-[(Benzofuran-2-ylmethyl)-amino]-3-(1H-indol-3-yl)-2-methyl-N-(4-nitro-benzyl)-propionamide | 4,1 | 483 | 100 | 0 07 | 89 |
| 120 | 2-[(Benzofuran-2-ylmethyl)-amino]-N-[2-(1H-indazol-3-yl)-1-methyl-ethyl]-3-(1H-indol-3-yl)-2-methyl-propionamide | 0,7 | 506 | 94 | 0 06 | 2652 |
| 121 | 2-[(Benzofuran-2-ylmethyl)-amino]-3-(1H-indol-3-yl)-2-methyl-N-(2-pyrrol-1-yl-ethyl)-propionamide | 15 | 441 | 100 | 0 05 | 654 |
| 122 | 2-[(Benzofuran-2-ylmethyl)-amino]-N-[1-(2,5-dichloro-thiophen-3-yl)-ethyl]-3-(1H-indol-3-yl)-2-methyl-propionamide | 8,7 | 526 | 100 | 0 08 | 442 |
| 123 | 2-[(Benzofuran-2-ylmethyl)-amino]-3-(1H-indol-3-yl)-2-methyl-N-[2-(octahydro-indol-1-yl)-ethyl]-propionamide | 7,3 | 499 | 63 | 0 04 | >10,000 |
| 124 | 2-[(Benzofuran-2-ylmethyl)-amino]-3-(1H-indol-3-yl)-2-methyl-N-[1-(4-nitro-phenyl)-ethyl]-propionamide | 2,6 | 497 | 100 | 0 07 | 92 |
| 125 | 2-[(Benzofuran-2-ylmethyl)-amino]-3-(1H-indol-3-yl)-2-methyl-N-(2-piperidin-1-yl-ethyl)-propionamide | 29,5 | 459 | 97 | 0 04 | >10,000 |

TABLE 2-continued

Examples 23–191

| Ex. | Name | Yield (mg) | Mol. ion | Lcms % purity | Lcms Rt (min) | IC$_{50}$ (nM) hNK$_1$ |
|---|---|---|---|---|---|---|
| 126 | 2-[(Benzofuran-2-ylmethyl)-amino]-3-(1H-indol-3-yl)-2-methyl-N-(2-methyl-[1,3]dioxolan-2-ylmethyl)-propionamide | 28 | 448 | 95 | 0 07 | 6794 |
| 127 | 2-[(Benzofuran-2-ylmethyl)-amino]-N-furan-2-ylmethyl-3-(1H-indol-3-yl)-2-methyl-propionamide | 23,9 | 427 | 100 | 0 05 | 191 |
| 128 | 2-[(Benzofuran-2-ylmethyl)-amino]-3-(1H-indol-3-yl)-2-methyl-N-(2-morpholin-4-yl-ethyl)-propionamide | 31,7 | 461 | 95 | 0 03 | >10,000 |
| 129 | 2-[(Benzofuran-2-ylmethyl)-amino]-3-(1H-indol-3-yl)-2-methyl-N-(3-methyl-benzyl)-propionamide | 37,7 | 452 | 100 | 0 06 | 43 |
| 130 | 2-[(Benzofuran-2-ylmethyl)-amino]-N-indan-1-yl-3-(1H-indol-3-yl)-2-methyl-propionamide | 37,8 | 464 | 100 | 0 05 | 163 |
| 131 | 2-[(Benzofuran-2-ylmethyl)-amino]-3-(1H-indol-3-yl)-2-methyl-N-(2-methyl-2-piperidin-1-yl-propyl)-propionamide | 31,6 | 487 | 100 | 0 08 | >10,000 |
| 132 | 2-[(Benzofuran-2-ylmethyl)-amino]-3-(1H-indol-3-yl)-2-methyl-N-[2-(2-thioxo-imidazolidin-1-yl)-ethyl]-propionamide | 24,6 | 476 | 97 | 0 02 | 6035 |
| 133 | 2-[(Benzofuran-2-ylmethyl)-amino]-3-(1H-indol-3-yl)-2-methyl-N-(2-methyl-2-phenyl-propyl)-propionamide | 5 | 480 | 87 | 0 06 | 4479 |
| 134 | 2-[(Benzofuran-2-ylmethyl)-amino]-N-(3-imidazol-1-yl-propyl)-3-(1H-indol-3-yl)-2-methyl-propionamide | 27,3 | 456 | 100 | 0 02 | 5368 |
| 135 | 2-[(Benzofuran-2-ylmethyl)-amino]-3-(1H-indol-3-yl)-2-methyl-N-(tetrahydro-furan-2-ylmethyl)-propionamide | 13,5 | 432 | 100 | 0 03 | 1205 |
| 136 | 2-[(Benzofuran-2-ylmethyl)-amino]-3-(1H-indol-3-yl)-2-methyl-N-(2-methyl-tetrahydro-furan-2-ylmethyl)-propionamide | 26,6 | 446 | 95 | 0 02 | >10,000 |
| 137 | 2-[(Benzofuran-2-ylmethyl)-amino]-3-(1H-indol-3-yl)-2-methyl-N-thiophen-2-ylmethyl-propionamide | 33,6 | 444 | 96 | 0 03 | 100 |
| 138 | 2-[(Benzofuran-2-ylmethyl)-amino]-3-(1H-indol-3-yl)-2-methyl-N-(tetrahydro-furan-2-ylmethyl)-propionamide | 25,4 | 432 | 96 | 0 02 | 4867 |
| 139 | 2-[(Benzofuran-2-ylmethyl)-amino]-N-(2,5-difluoro-benzyl)-3-(1H-indol-3-yl)-2-methyl-propionamide | 41,7 | 474 | 93 | 0 05 | 99 |
| 140 | 2-[(Benzofuran-2-ylmethyl)-amino]-3-(1H-indol-3-yl)-2-methyl-N-(2-phenyl-propyl)-propionamide | 31,8 | 466 | 100 | 0 05 | >10,000 |
| 141 | N-(4-Amino-naphthalen-1-ylmethyl)-2-[(benzofuran-2-ylmethyl)-amino]-3-(1H-indol-3-yl)-2-methyl-propionamide | 11,6 | 503 | 95 | 0 03 | 2337 |
| 142 | 2-[(Benzofuran-2-ylmethyl)-amino]-N-(2,3-dimethoxy-benzyl)-3-(1H-indol-3-yl)-2-methyl-propionamide | 19,3 | 498 | 96 | 0 03 | 1961 |
| 143 | 2-[(Benzofuran-2-ylmethyl)-amino]-N-[2-(4-hydroxy-phenyl)-ethyl]-3-(1H-indol-3-yl)-2-methyl-propionamide | 32,9 | 468 | 96 | 0 02 | >10,000 |
| 144 | 2-[(Benzofuran-2-ylmethyl)-amino]-N-(1-hydroxymethyl-cyclopentyl)-3-(1H-indol-3-yl)-2-methyl-propionamide | 16,4 | 446 | 94 | 0 02 | >10,000 |
| 145 | 2-[(Benzofuran-2-ylmethyl)-amino]-3-(1H-indol-3-yl)-2-methyl-N-(2-pyridin-3-yl-ethyl)-propionamide | 35,9 | 453 | 97 | 0 01 | 1301 |
| 146 | 2-[(Benzofuran-2-ylmethyl)-amino]-N-[1-(4,5-dihydro-furan-2-yl)-ethyl]-3-(1H-indol-3-yl)-2-methyl-propionamide | 0,8 | 444 | 90 | 0 02 | 3587 |

TABLE 2-continued

Examples 23–191

| Ex. | Name | Yield (mg) | Mol. ion | Icms % purity | Icms Rt (min) | IC$_{50}$ (nM) hNK$_1$ |
|---|---|---|---|---|---|---|
| 147 | 2-[(Benzofuran-2-ylmethyl)-amino]-3-(1H-indol-3-yl)-2-methyl-N-(2-piperazin-1-yl-ethyl)-propionamide | 18,5 | 460 | 98 | 0 02 | >10,000 |
| 148 | 2-[(Benzofuran-2-ylmethyl)-amino]-3-(1H-indol-3-yl)-2-methyl-N-(1,2,3,4-tetrahydro-naphthalen-1-yl)-propionamide | 34,7 | 478 | 93 | 0 03 | >10,000 |
| 149 | 2-[(Benzofuran-2-ylmethyl)-amino]-N-(2,5-dimethoxy-2,5-dihydro-furan-2-ylmethyl)-3-(1H-indol-3-yl)-2-methyl-propionamide | 31,8 | 490 | 75 | 0 02 | >10,000 |
| 150 | 2-[(Benzofuran-2-ylmethyl)-amino]-3-(1H-indol-3-yl)-2-methyl-N-(2-phenyl-propyl)-propionamide | 32,4 | 466 | 95 | 0 04 | 262 |
| 151 | 2-[(Benzofuran-2-ylmethyl)-amino]-3-(1H-indol-3-yl)-2-methyl-N-quinolin-3-ylmethyl-propionamide | 2,4 | 489 | 100 | 0 02 | 1213 |
| 152 | 4-[2-[(Benzofuran-2-ylmethyl)-amino]-3-(1H-indol-3-yl)-2-methyl-propionylamino]-3-phenyl-butyric acid | 9 | 510 | 94 | 0 01 | >10,000 |
| 153 | 2-[(Benzofuran-2-ylmethyl)-amino]-N-[2-hydroxy-2-(4-hydroxy-3-methoxy-phenyl)-ethyl]-3-(1H-indol-3-yl)-2-methyl-propionamide | 6,9 | 514 | 100 | 0 01 | 3555 |
| 154 | 2-[(Benzofuran-2-ylmethyl)-amino]-3-(1H-indol-3-yl)-2-methyl-N-pyrrolidin-3-ylmethyl-propionamide | 6,1 | 431 | 5 | 0 04 | >10,000 |
| 155 | 2-[(Benzofuran-2-ylmethyl)-amino]-3-(1H-indol-3-yl)-2-methyl-N-(2-pyrrolidin-1-yl-ethyl)-propionamide | 25,2 | 445 | 93 | 0 02 | >10,000 |
| 156 | 2-[(Benzofuran-2-ylmethyl)-amino]-3-(1H-indol-3-yl)-2-methyl-N-piperidin-4-ylmethyl-propionamide | 1,4 | 445 | 3 | 0 05 | >10,000 |
| 157 | 2-[(Benzofuran-2-ylmethyl)-amino]-3-(1H-indol-3-yl)-2-methyl-N-(2-methyl-benzyl)-propionamide | 38,2 | 452 | 95 | 0 02 | 455 |
| 158 | 2-[(Benzofuran-2-ylmethyl)-amino]-N-indan-1-yl-3-(1H-indol-3-yl)-2-methyl-propionamide | 21,4 | 464 | 96 | 0 02 | 2567 |
| 159 | 2-[(Benzofuran-2-ylmethyl)-amino]-3-(1H-indol-3-yl)-2-methyl-N-(1-pyridin-3-yl-cyclobutylmethyl)-propionamide | 7 | 492 | 92 | 0 01 | 3757 |
| 160 | 2-[(Benzofuran-2-ylmethyl)-amino]-3-(1H-indol-3-yl)-2-methyl-N-(1-thiophen-2-yl-cyclohexyl)-propionamide | 6,1 | 511 | 100 | 0 03 | >10,000 |
| 161 | 2-[(Benzofuran-2-ylmethyl)-amino]-N-[2-(3,4-dihydroxy-phenyl)-ethyl]-3-(1H-indol-3-yl)-2-methyl-propionamide | 12,3 | 484 | 100 | 0 01 | >10,000 |
| 162 | 2-[(Benzofuran-2-ylmethyl)-amino]-3-(1H-indol-3-yl)-2-methyl-N-(1-phenyl-propyl)-propionamide | 8,7 | 466 | 95 | 0 02 | 42 |
| 163 | 2-[(Benzofuran-2-ylmethyl)-amino]-3-(1H-indol-3-yl)-2-methyl-N-(2-oxo-2-phenyl-ethyl)-propionamide | 16,9 | 466 | 80 | 0 07 | 166 |
| 164 | 2-[(Benzofuran-2-ylmethyl)-amino]-N-(5-hydroxy-4-oxo-4H-pyran-2-ylmethyl)-3-(1H-indol-3-yl)-2-methyl-propionamide | 5,5 | 542 | 10 | 0 06 | >10,000 |
| 165 | 2-[(Benzofuran-2-ylmethyl)-amino]-N-bicyclo[2.2.1]hept-2-ylmethyl-3-(1H-indol-3-yl)-2-methyl-propionamide | 38,1 | 456 | 100 | 0 08 | >10,000 |
| 166 | 2-[(Benzofuran-2-ylmethyl)-amino]-N-(3-fluoro-benzyl)-3-(1H-indol-3-yl)-2-methyl-propionamide | 41,9 | 456 | 95 | 0 07 | 37 |
| 167 | 2-[(Benzofuran-2-ylmethyl)-amino]-N-(3,4-difluoro-benzyl)-3-(1H-indol-3-yl)-2-methyl-propionamide | 23,2 | 474 | 100 | 0 07 | 29 |

TABLE 2-continued

Examples 23–191

| Ex. | Name | Yield (mg) | Mol. ion | Icms % purity | Icms Rt (min) | IC$_{50}$ (nM) hNK$_1$ |
|---|---|---|---|---|---|---|
| 168 | 2-[(Benzofuran-2-ylmethyl-amino]-N-(2-chloro-4-fluoro-benzyl)-3-(1H-indol-3-yl)-2-methyl-propionamide | 42,8 | 490 | 95 | 0 08 | 230 |
| 169 | 2-[(Benzofuran-2-ylmethyl)-amino]-N-(4,6-dimethyl-pyridin-3-ylmethyl)-3-(1H-indol-3-yl)-2-methyl-propionamide | 11,2 | 467 | 100 | 0 06 | 6016 |
| 170 | 2-[(Benzofuran-2-ylmethyl)-amino]-N-(5-bromo-2-hydroxy-benzyl)-3-(1H-indol-3-yl)-2-methyl-propionamide | 49,6 | 533 | 100 | 0 08 | 2384 |
| 171 | 4-{[2-[(Benzofuran-2-ylmethyl)-amino]-3-(1H-indol-3-yl)-2-methyl-propionylamino]-methyl}-benzoic acid | 28,7 | 482 | 95 | 0 06 | >10,000 |
| 172 | 2-[(Benzofuran-2-ylmethyl)-amino]-3-(1H-indol-3-yl)-2-methyl-N-(2-thiophen-2-yl-ethyl)-propionamide | 36,8 | 458 | 100 | 0 07 | 153 |
| 173 | 2-[(Benzofuran-2-ylmethyl)-amino]-3-(1H-indol-3-yl)-2-methyl-N-(2-morpholin-4-yl-2-oxo-ethyl)-propionamide | 36,3 | 475 | 90 | 0 06 | >10,000 |
| 174 | N-Benzo[1,3]dioxol-5-ylmethyl-2-[(benzofuran-2-ylmethyl)-amino]-3-(1H-indol-3-yl)-2-methyl-propionamide | 45,7 | 482 | 100 | 0 07 | 94 |
| 175 | 2-[(Benzofuran-2-ylmethyl)-amino]-N-(3,4-dichloro-benzyl)-3-(1H-indol-3-yl)-2-methyl-propionamide | 21,4 | 507 | 90 | 0 08 | 96 |
| 176 | 2-[2-[(Benzofuran-2-ylmethyl)-amino]-3-(1H-indol-3-yl)-2-methyl-propionylamino]-3-(1H-imidazol-4-yl)-propionic acid methyl ester | 44,3 | 453 | 100 | 0 07 | 1763 |
| 177 | 2-[(Benzofuran-2-ylmethyl)-amino]-N-(4-chloro-2-fluoro-benzyl)-3-(1H-indol-3-yl)-2-methyl-propionamide | 24,6 | 490 | 100 | 0 08 | 444 |
| 178 | N-(3-Amino-benzyl)-2-[(benzofuran-2-ylmethyl)-amino]-3-(1H-indol-3-yl)-2-methyl-propionamide | 36,2 | 453 | 100 | 0 06 | 1373 |
| 179 | 2-[(Benzofuran-2-ylmethyl)-amino]-N-(2,4-diamino-pyrimidin-5-ylmethyl)-3-(1H-indol-3-yl)-2-methyl-propionamide | 3,1 | 470 | 56 | 0 06 | 5917 |
| 180 | 2-[(Benzofuran-2-ylmethyl)-amino]-N-(2-fluoro-benzyl)-3-(1H-indol-3-yl)-2-methyl-propionamide | 42 | 456 | 95 | 0 07 | 266 |
| 181 | 2-[(Benzofuran-2-ylmethyl)-amino]-N-(2,4-difluoro-benzyl)-3-(1H-indol-3-yl)-2-methyl-propionamide | 23,4 | 474 | 100 | 0 07 | 269 |
| 182 | 2-[(Benzofuran-2-ylmethyl)-amino]-N-(3,4-dihydroxy-benzyl)-3-(1H-indol-3-yl)-2-methyl-propionamide | 4,1 | 470 | 90 | 0 06 | >10,000 |
| 183 | 2-[(Benzofuran-2-ylmethyl)-amino]-N-[1-hydroxymethyl-2-(1H-imidazol-4-yl)-ethyl]-3-(1H-indol-3-yl)-2-methyl-propionamide | 1,7 | 472 | 33 | 0 05 | >10,000 |
| 184 | 2-[(Benzofuran-2-ylmethyl)-amino]-N-(2-hydroxy-cyclohexylmethyl)-3-(1H-indol-3-yl)-2-methyl-propionamide | 36,4 | 460 | 100 | 0 07 | >10,000 |
| 185 | 2-[(Benzofuran-2-ylmethyl)-amino]-3-(1H-indol-3-yl)-2-methyl-N-(3-morpholin-4-yl-propyl)-propionamide | 28,5 | 475 | 100 | 0 06 | >10,000 |
| 186 | 2-[(Benzofuran-2-ylmethyl)-amino]-N-(2-hydroxy-benzyl)-3-(1H-indol-3-yl)-2-methyl-propionamide | 8,5 | 454 | 81 | 0 07 | 84 |
| 187 | 2-[(Benzofuran-2-ylmethyl)-amino]-N-(3-fluoro-4-methoxy-benzyl)-3-(1H-indol-3-yl)-2-methyl-propionamide | 42,2 | 486 | 100 | 0 07 | 131 |

TABLE 2-continued

Examples 23–191

| Ex. | Name | Yield (mg) | Mol. ion | Icms % purity | Icms Rt (min) | IC$_{50}$ (nM) hNK$_1$ |
|---|---|---|---|---|---|---|
| 188 | N-(2-Amino-4-methoxy-benzyl)-2-[(benzofuran-2-ylmethyl)-amino]-3-(1H-indol-3-yl)-2-methyl-propionamide | 10 | 483 | 96 | 0 06 | 2282 |
| 189 | 2-((Benzofuran-2-ylmethyl)-amino]-N-(2-chloro-benzyl)-3-(1H-indol-3-yl)-2-methyl-propionamide | 47 | 472 | 94 | 0 07 | 1129 |
| 190 | 2-[(Benzofuran-2-ylmethyl)-amino]-N-(2,6-difluoro-benzyl)-3-(1H-indol-3-yl)-2-methyl-propionamide | 41,6 | 474 | 97 | 0 07 | 3537 |
| 191 | 2-[(Benzofuran-2-ylmethyl)-amino]-N-(3-chloro-4-fluoro-benzyl)-3-(1H-indol-3-yl)-2-methyl-propionamide | 24,4 | 490 | 99 | 0 07 | 55 |

TABLE 3

Examples 192–308

| Ex. | Name | Yield (mg) | Mol. ion | Icms % purity | Icms Rt (min) | IC$_{50}$ (nM) hNK$_1$ |
|---|---|---|---|---|---|---|
| 192 | 2-[(Benzofuran-2-ylmethyl)-amino]-3-(1H-indol-3-yl)-N-pyridin-2-ylmethyl-propionamide | 26 | 425 | 100 | 3, 94 | 1981 |
| 193 | 2-[(Benzofuran-2-ylmethyl)-amino]-3-(1H-indol-3-yl)-N-(2-piperazin-1-yl-ethyl)-propionamide | 27 | 446 | 94 | 1, 04 | >10,000 |
| 194 | 2-[(Benzofuran-2-ylmethyl)-amino]-3-(1H-indol-3-yl)-N-(1,2,3,4-tetrahydro-naphthalen-1-yl)-propionamide | 41 | 464 | 100 | 5.63, 5.80 | 703 |
| 195 | 2-[(Benzofuran-2-ylmethyl)-amino]-N-indan-1-yl-3-(1H-indol-3-yl)-propionamide | 23 | 450 | 100 | 5, 39 | 1750 |
| 196 | 2-[(Benzofuran-2-ylmethyl)-amino]-3-(1H-indol-3-yl)-N-(1-thiophen-2-yl-propyl)-propionamide | 36 | 458 | 100 | 5, 67 | 92 |
| 197 | 2-[(Benzofuran-2-ylmethyl)-amino]-3-(1H-indol-3-yl)-N-(1-naphthalen-1-yl-ethyl)-propionamide | 44 | 488 | 99 | 6, 77 | 933 |
| 198 | 2-[(Benzofuran-2-ylmethyl)-amino]-3-(1H-indol-3-yl)-N-[2-(1-methyl-pyrrolidin-2-yl)-ethyl]-propionamide | 31 | 445 | 99 | 2, 27 | >10,000 |
| 199 | 2-[(Benzofuran-2-ylmethyl)-amino]-3-(1H-indol-3-yl)-N-(4-methoxy-benzyl)-propionamide | 39 | 454 | 100 | 5, 11 | 130 |
| 200 | 2-[(Benzofuran-2-ylmethyl)-amino]-3-(1H-indol-3-yl)-N-(3-trifluoromethoxy-benzyl)-propionamide | 34 | 508 | 96 | 6, 19 | 355 |
| 201 | 2-[(Benzofuran-2-ylmethyl)-amino]-N-(3-imidazol-1-yl-propyl)-3-(1H-indol-3-yl)-propionamide | 21 | 442 | 100 | 1, 22 | >10,000 |
| 202 | 2-[(Benzofuran-2-ylmethyl)-amino]-3-(1H-indol-3-yl)-N-pyrrolidin-3-yl-methyl-propionamide | 6 | 417 | 98 | 4, 3 | 2184 |
| 203 | 2-[(Benzofuran-2-ylmethyl)-amino]-3-(1H-indol-3-yl)-N-piperidin-4-yl-methyl-propionamide | 22 | 431 | 96 | 1, 26 | >10,000 |
| 204 | 2-[(Benzofuran-2-ylmethyl)-amino]-N-(2,5-difluoro-benzyl)-3-(1H-indol-3-yl)-propionamide | 18 | 460 | 100 | 5, 53 | 68 |
| 205 | 2-[(Benzofuran-2-ylmethyl)-amino]-3-(1H-indol-3-yl)-N-quinolin-3-ylmethyl-propionamide | 10 | 475 | 97 | 4, 27 | 2315 |
| 206 | 2-[(Benzofuran-2-ylmethyl)-amino]-N-[2-(1H-imidazol-4-yl)-ethyl]-3-(1H-indol-3-yl)-propionamide | 16 | 428 | 98 | 2, 31 | 6681 |
| 207 | 2-[(Benzofuran-2-ylmethyl)-amino]-3-(1H-indol-3-yl)-N-(1-naphthalen-1-yl-ethyl)-propionamide | 43 | 489 | 98 | 6, 76 | 591 |
| 208 | 2-[(Benzofuran-2-ylmethyl)-amino]-3-(1H-indol-3-yl)-N-[1-(5-methyl-thiophen-2-yl)-ethyl]-propionamide | 31 | 458 | 100 | 5, 94 | 15 |

TABLE 3-continued

Examples 192–308

| Ex. | Name | Yield (mg) | Mol. ion | Icms % purity | Icms Rt (min) | IC$_{50}$ (nM) hNK$_1$ |
|---|---|---|---|---|---|---|
| 209 | 2-[(Benzofuran-2-ylmethyl)-amino]-3-(1H-indol-3-yl)-N-(4-methyl-benzyl)-propionamide | 35 | 438 | 100 | 5, 74 | 82 |
| 210 | 2-[(Benzofuran-2-ylmethyl)-amino]-3-(1H-indol-3-yl)-N-(1-p-tolyl-ethyl)-propionamide | 36 | 452 | 100 | 5, 98 | 337 |
| 211 | 2-[(Benzofuran-2-ylmethyl)-amino]-N-(1-hydroxy-methylcyclopentyl)-3-(1H-indol-3-yl)-propionamide | 21 | 432 | 100 | 5 | >10,000 |
| 212 | 2-[(Benzofuran-2-ylmethyl)-amino]-3-(1H-indol-3-yl)-N-(2-pyrrol-1-yl-ethyl)-propionamide | 18 | 427 | 96 | 5, 21 | 658 |
| 213 | 2-[(Benzofuran-2-ylmethyl)-amino]-3-(1H-indol-3-yl)-N-(2-morpholin-4-yl-ethyl)-propionamide | 28 | 447 | 100 | 1, 39 | 1256 |
| 214 | 2-[(Benzofuran-2-ylmethyl)-amino]-N-(4-dimethyl-amino-benzyl)-3-(1H-indol-3-yl)-propionamide | 39 | 467 | 99 | 4, 3 | 4015 |
| 215 | 2-[(Benzofuran-2-ylmethyl)-amino]-N-(2,5-dichloro-thiophen-3-yl-methyl)-3-(1H-indol-3-yl)-propionamide | 9 | 498 | 97 | 6, 61 | 70 |
| 216 | 2-[(Benzofuran-2-ylmethyl)-amino]-3-(1H-indol-3-yl)-N-(5-nitro-furan-2-yl-methyl)-propionamide | 2 | 459 | 11 | 5, 07 | >10,000 |
| 217 | 2-[(Benzofuran-2-ylmethyl)-amino]-N-[1-(4-dimethyl-amino-phenyl)-ethyl]-3-(1H-indol-3-yl)-propionamide | 44 | 481 | 99 | 4.46, 4.78 | 819 |
| 218 | 2-[(Benzofuran-2-ylmethyl)-amino]-N-(3,5-bis-trifluoro-methyl-benzyl)-3-(1H-indol-3-yl)-propionamide | 20 | 560 | 85 | 7, 14 | 294 |
| 219 | 2-[(Benzofuran-2-ylmethyl)-amino]-N-(3-bromo-benzyl)-3-1H-indol-3-yl)-propionamide | 17 | 502 | 96 | 6, 96 | 31 |
| 220 | 2-[(Benzofuran-2-ylmethyl)-amino]-3-(1H-indol-3-yl)-N-(1-p-tolyl-ethyl)-propionamide | 38 | 452 | 100 | 6, 16 | 2 |
| 221 | 2-[(Benzofuran-2-ylmethyl)-amino]-3-(1H-indol-3-yl)-N-(4-nitro-benzyl)-propionamide | 37 | 469 | 100 | 5, 67 | 23 |
| 222 | 2-[(Benzofuran-2-ylmethyl)-amino]-3-(1H-indol-3-yl)-N-(2-pyrrolidin-1-yl-ethyl)-propionamide | 30 | 431 | 100 | 1, 64 | >10,000 |
| 223 | 2-[(Benzofuran-2-ylmethyl)-amino]-3-(1H-indol-3-yl)-N-(tetrahydro-furan-2-ylmethyl)-propionamide | 36 | 418 | 100 | 4, 65 | >10,000 |
| 224 | 2-[(Benzofuran-2-ylmethyl)-amino]-3-(1H-indol-3-yl)-N-(2-phenyl-cyclopropyl)-propionamide | 9 | 450 | 100 | 6, 05 | 2902 |
| 225 | 2-[(Benzofuran-2-ylmethyl)-amino]-N-(1-cyclohexyl-1-methyl-ethyl)-3-(1H-indol-3-yl)-propionamide | 32 | 458 | 97 | 7, 07 | 1341 |
| 226 | 2-[(Benzofuran-2-ylmethyl)-amino]-N-cyclohexyl-methyl-3-(1H-indol-3-yl)-propionamide | 33 | 430 | 100 | 6, 23 | 54 |
| 227 | 2-[(Benzofuran-2-ylmethyl)-amino]-N-[1-(3-dimethyl-amino-phenyl)-ethyl]-3-(1H-indol-3-yl)-propionamide | 41 | 481 | 96 | 5.05, 5.36 | 182 |
| 228 | 2-[(Benzofuran-2-ylmethyl)-amino]-3-(1H-indol-3-yl)-N-(3-trifluoromethyl-benzyl)-propionamide | 31 | 492 | 100 | 6, 63 | 82 |
| 229 | 2-[(Benzofuran-2-ylmethyl)-amino]-N-(3-chloro-4-fluoro-benzyl)-3-(1H-indol-3-yl)-propionamide | 39 | 476 | 98 | 6, 4 | 33 |
| 230 | 2-[(Benzofuran-2-ylmethyl)-amino]-3-(1H-indol-3-yl)-N-[1-(1-methyl-1H-pyrrol-3-yl)-ethyl]-propionamide | 38 | 441 | 100 | 5, 54 | 21 |
| 231 | 2-[(Benzofuran-2-ylmethyl)-amino]-3-(1H-indol-3-yl)-N-pyridin-3-ylmethyl-propionamide | 35 | 425 | 100 | 0 04 | 790 |
| 232 | 2-[(Benzofuran-2-ylmethyl)-amino]-3-(1H-indol-3-yl)-N-thiophen-2-yl-methyl-propionamide | 30 | 430 | 100 | 0 06 | 63 |
| 233 | 2-[(Benzofuran-2-ylmethyl)-amino]-3-(1H-indol-3-yl)-N-(2-phenyl-propyl)-propionamide | 37 | 452 | 100 | 0 07 | 1998 |
| 234 | 2-[(Benzofuran-2-ylmethyl)-amino]-3-(1H-indol-3-yl)-N-(1-phenyl-ethyl)-propionamide | 37 | 438 | 100 | 0 07 | 75 |

TABLE 3-continued

Examples 192–308

| Ex. | Name | Yield (mg) | Mol. ion | Lcms % purity | Lcms Rt (min) | IC$_{50}$ (nM) hNK$_1$ |
|---|---|---|---|---|---|---|
| 235 | 2-[(Benzofuran-2-ylmethyl)-amino]-N-[1-(4-fluoro-phenyl)-ethyl]-3-(1H-indol-3-yl)-propionamide | 40 | 456 | 100 | 0 07 | 3 |
| 236 | 2-[(Benzofuran-2-ylmethyl)-amino]-3-(1H-indol-3-yl)-N-(1-thiophen-3-yl-ethyl)-propionamide | 41 | 444 | 100 | 0 07 | 7 |
| 237 | 2-[(Benzofuran-2-ylmethyl)-amino]-3-(1H-indol-3-yl)-N-(2-oxo-2-phenyl-ethyl)-propionamide | 38 | 435 | 0 | 0 10 | 5341 |
| 238 | 2-[(Benzofuran-2-ylmethyl)-amino]-N-(2-fluoro-benzyl)-3-(1H-indol-3-yl)-propionamide | 34 | 442 | 100 | 0 07 | 89 |
| 239 | 2-[(Benzofuran-2-ylmethyl)-amino]-N-indan-2-yl-3-(1H-indol-3-yl)-propionamide | 36 | 450 | 100 | 0 07 | 243 |
| 240 | 2-[(Benzofuran-2-ylmethyl)-amino]-N-indol-3-yl)-N-pyridin-4-ylmethyl-propionamide | 33 | 425 | 100 | 0 04 | 196 |
| 241 | 2-[(Benzofuran-2-ylmethyl)-amino]-N-(1-cyclohexyl-ethyl)-3-(1H-indol-3-yl)-propionamide | 29 | 444 | 100 | 0 07 | 2 |
| 242 | 2-[(Benzofuran-2-ylmethyl)-amino]-3-(1H-indol-3-yl)-N-(2-methyl-benzyl)-propionamide | 39 | 438 | 100 | 0 07 | 170 |
| 243 | 2-[(Benzofuran-2-ylmethyl)-amino]-N-[1-(5-chloro-thiophen-2-yl)-ethyl]-3-(1H-indol-3-yl)-propionamide | 44 | 478 | 100 | 0 07 | 15 |
| 244 | 2-[(Benzofuran-2-ylmethyl)-amino]-N-(4-fluoro-benzyl)-3-(1H-indol-3-yl)-propionamide | 38 | 442 | 100 | 0 07 | 12 |
| 245 | 2-[(Benzofuran-2-ylmethyl)-amino]-3-(1H-indol-3-yl)-N-[1-(4-nitro-phenyl)-ethyl]-propionamide | 32 | 483 | 100 | 0 07 | 3 |
| 246 | 2-[(Benzofuran-2-ylmethyl)-amino]-3-(1H-indol-3-yl)-N-phenethyl-propionamide | 39 | 438 | 100 | 0 07 | 77 |
| 247 | 2-[(Benzofuran-2-ylmethyl)-amino]-3-(1H-indol-3-yl)-N-(2-thiophen-2-yl-ethyl)-propionamide | 33 | 444 | 100 | 0 07 | 56 |
| 248 | 2-[(Benzofuran-2-ylmethyl)-amino]-N-(3-fluoro-benzyl)-3-(1H-indol-3-yl)-propionamide | 37 | 442 | 100 | 0 07 | 6 |
| 249 | 2-[(Benzofuran-2-ylmethyl)-amino]-N-(2-hydroxy-1-phenyl-ethyl)-3-(1H-indol-3-yl)-propionamide | 43 | 454 | 100 | 0 06 | 607 |
| 250 | 2-[(Benzofuran-2-ylmethyl)-amino]-N-(1H-benzo-imidazol-2-yl-methyl)-3-(1H-indol-3-yl)-propionamide | 36 | 464 | 100 | 0 05 | 3413 |
| 251 | 2-[(Benzofuran-2-ylmethyl)-amino]-N-(2-furan-2-yl-ethyl)-3-(1H-indol-3-yl)-propionamide | 4 | 428 | 95 | 0 06 | 129 |
| 252 | 2-[(Benzofuran-2-ylmethyl)-amino]-3-(1H-indol-3-yl)-N-(3-methyl-benzyl)-propionamide | 37 | 438 | 100 | 0 07 | 33 |
| 253 | 2-[(Benzofuran-2-ylmethyl)-amino]-3-(1H-indol-3-yl)-N-(1,2,3,4-tetrahydro-naphthalen-2-yl)-propionamide | 25 | 464 | 81 | 0 07 | 3327 |
| 254 | 2-[(Benzofuran-2-ylmethyl)-amino]-N-benzyl-3-(1H-indol-3-yl)-propionamide | 37 | 424 | 100 | 0 06 | 22 |
| 255 | 2-[(Benzofuran-2-ylmethyl)-amino]-3-(1H-indol-3-yl)-N-[1-(4-methoxy-phenyl)-ethyl]-propionamide | 41 | 468 | 100 | 0 07 | 9 |
| 256 | 2-[(Benzofuran-2-ylmethyl)-amino]-N-(2-hydroxy-benzyl)-3-(1H-indol-3-yl)-propionamide | 5 | 440 | 68 | 0 05 | >10,000 |
| 257 | 2-[(Benzofuran-2-ylmethyl)-amino]-3-(1H-indol-3-yl)-N-(2-methyl-2-phenyl-propyl)-propionamide | 35 | 466 | 100 | 0 07 | >10,000 |
| 258 | 2-[(Benzofuran-2-ylmethyl)-amino]-N-(4-chloro-benzyl)-3-(1H-indol-3-yl)-propionamide | 38 | 458 | 100 | 0 07 | 46 |
| 259 | 2-[(Benzofuran-2-ylmethyl)-amino]-3-(1H-indol-3-yl)-N-(1-phenyl-propyl)-propionamide | 39 | 452 | 100 | 0 07 | 21 |
| 260 | 2-[(Benzofuran-2-ylmethyl)-amino]-3-(1H-indol-3-yl)-N-(3-nitro-benzyl)-propionamide | 32 | 469 | 100 | 0 06 | 14 |
| 261 | 2-[(Benzofuran-2-ylmethyl)-amino]-N-furan-2-ylmethyl-3-(1H-indol-3-yl)-propionamide | 31 | 414 | 100 | 0 06 | 406 |

TABLE 3-continued

Examples 192–308

| Ex. | Name | Yield (mg) | Mol. ion | Icms % purity | Icms Rt (min) | IC$_{50}$ (nM) hNK$_1$ |
|---|---|---|---|---|---|---|
| 262 | 2-[(Benzofuran-2-ylmethyl)-amino]-N-indan-1-yl-3-(1H-indol-3-yl)-propionamide | 41 | 450 | 100 | 0 07 | 86 |
| 263 | 2-[(Benzofuran-2-ylmethyl)-amino]-N-(3-chloro-benzyl)-3-(1H-indol-3-yl)-propion-amide | 36 | 458 | 100 | 0 07 | 9 |
| 264 | 2-[(Benzofuran-2-ylmethyl)-amino]-N-[1(4-chloro-phenyl)-ethyl]-3-(1H-indol-3-yl)-propionamide | 44 | 472 | 100 | 0 07 | 7 |
| 265 | 2-[(Benzofuran-2-ylmethyl)-amino]-3-(1H-indol-3-yl)-N-(1-methyl-1-phenyl-ethyl)-propionamide | 41 | 452 | 96 | 0 07 | 328 |
| 266 | 2-[(Benzofuran-2-ylmethyl)-amino]-N-bicyclo[2.2.1]-hept-2-ylmethyl-3-(1H-indol-3-yl)-propionamide | 39 | 442 | 100 | 0 07 | 633 |
| 267 | N-Benzo[1,3]-dioxol-5-ylmethyl-2-[(benzofuran-2-ylmethyl)-amino]-3-(1H-indol-3-yl)-propionamide | 40 | 468 | 100 | 0 06 | 55 |
| 268 | 2-[(Benzofuran-2-ylmethyl)-amino]-N-(3,4-difluoro-benzyl)-3-(1H-indol-3-yl)-propion-amide | 39 | 460 | 91 | 0 07 | 10 |
| 269 | 2-[(Benzofuran-2-ylmethyl)-amino]-3-(1H-indol-3-yl)-N-(1-pyridin-4-yl-ethyl)-propionamide | 9 | 439 | 92 | 0 04 | 9 |
| 270 | 2-[(Benzofuran-2-ylmethyl)-amino]-N-(2-hydroxy-cyclo-hexyl)-3-(1H-indol-3-yl)-propionamide | 19 | 432 | 100 | 0 04 | >10,000 |
| 271 | 2-[(Benzofuran-2-ylmethyl)-amino]-3-(1H-indol-3-yl)-N-[2-(4-methoxy-phenyl)-ethyl]-propionamide | 33 | 468 | 98 | 0 05 | 196 |
| 272 | 2-[(Benzofuran-2-ylmethyl)-amino]-N-(1-hydroxy-methyl-2-phenyl-ethyl)-3-(1H-indol-3-yl)-propionamide | 42 | 468 | 99 | 0 05 | 336 |
| 273 | 2-[(Benzofuran-2-ylmethyl)-amino]-N-(4-hydroxy-cyclo-hexyl)-3-(1H-indol-3-yl)-propionamide | 15 | 432 | 99 | 0 04 | >10,000 |
| 274 | 2-[(Benzofuran-2-ylmethyl)-amino]-N-[2-(2-fluoro-phenyl)-ethyl]-3-(1H-indol-3-yl)-propionamide | 21 | 456 | 97 | 0 05 | 264 |
| 275 | 2-[(Benzofuran-2-ylmethyl)-amino]-N-(2-benzyl-sulfanyl-1-hydroxy-methyl-ethyl)-3-(1H-indol-3-yl)-propionamide | 38 | 514 | 100 | 0 05 | 2157 |
| 276 | 2-[(Benzofuran-2-ylmethyl)-amino]-N-cyclohexyl-3-(1H-indol-3-yl)-propionamide | 10 | 416 | 84 | 0 05 | 655 |
| 277 | 2-[(Benzofuran-2-ylmethyl)-amino]-N-(2-cyclohexyl-1-hydroxymethyl-ethyl)-3-(1H-indol-3-yl)-propionamide | 17 | 474 | 96 | 0 05 | 2198 |
| 278 | 2-[(Benzofuran-2-ylmethyl)-amino]-3-(1H-indol-3-yl)-N-(3-phenyl-propyl)-propionamide | 33 | 452 | 88 | 0 05 | 2379 |
| 279 | 2-[(Benzofuran-2-ylmethyl)-amino]-N-(3,4-dichloro-benzyl)-3-(1H-indol-3-yl)-propion-amide | 8 | 493 | 86 | 0 06 | 30 |
| 280 | 2-[(Benzofuran-2-ylmethyl)-amino]-3-(1H-indol-3-yl)-N-[2-(1H-indol-3-yl)-ethyl]-propionamide | 25 | 477 | 97 | 0 05 | 2540 |
| 281 | 2-[(Benzofuran-2-ylmethyl)-amino]-3-(1H-indol-3-yl)-N-[2-(4-nitro-phenyl)-ethyl]-propionamide | 28 | 483 | 93 | 0 05 | 51 |
| 282 | 2-[(Benzofuran-2-ylmethyl)-amino]-N-[2-(4-chloro-phenyl)-1-methyl-ethyl]-3-(1H-indol-3-yl)-propionamide | 30 | 487 | 98 | 0 06 | 833 |
| 283 | 2-[(Benzofuran-2-ylmethyl)-amino]-3-(1H-indol-3-yl)-N-(4-trifluoromethyl-benzyl)-propion-amide | 9 | 492 | 91 | 0 06 | 420 |
| 284 | 2-[(Benzofuran-2-ylmethyl)-amino]-N-[2-(4-fluoro-phenyl)-ethyl]-3-(1H-indol-3-yl)-propionamide | 33 | 456 | 98 | 0 05 | 62 |
| 285 | 2-[(Benzofuran-2-ylmethyl)-amino]-3-(1H-indol-3-yl)-N-[1-(4-nitro-phenyl)-ethyl]-propionamide | 32 | 483 | 99 | 0 05 | 246 |
| 286 | 4-{[2-[(Benzofuran-2-ylmethyl)-amino]-3-(1H-indol-3-yl)-propionylamino]-methyl}-cyclo-hexanecarboxylic acid | 6 | 474 | 62 | 0 05 | >10,000 |

TABLE 3-continued

Examples 192–308

| Ex. | Name | Yield (mg) | Mol. ion | Icms % purity | Icms Rt (min) | IC$_{50}$ (nM) hNK$_1$ |
|---|---|---|---|---|---|---|
| 287 | 2-[(Benzofuran-2-ylmethyl)-amino]-N-(cyano-phenyl-methyl)-3-(1H-indol-3-yl)-propion-amide | 36 | 449 | 99 | 0 06 | 35 |
| 288 | 2-[(Benzofuran-2-ylmethyl)-amino]-N-[2-(4-chloro-phenyl)-ethyl]-3-(1H-indol-3-yl)-propionamide | 32 | 472 | 99 | 0 06 | 136 |
| 289 | 2-[(Benzofuran-2-ylmethyl)-amino]-N-(1-hydroxy-methyl-2-phenyl-ethyl)-3-(1H-indol-3-yl)-propionamide | 35 | 468 | 99 | 0 05 | 209 |
| 290 | 2-[(Benzofuran-2-ylmethyl)-amino]-N-[1-(4-bromo-phenyl)-ethyl]-3-(1H-indol-3-yl)-propionamide | 37 | 517 | 100 | 0 06 | 8 |
| 291 | 2-[(Benzofuran-2-ylmethyl)-amino]-3-(1H-indol-3-yl)-N-[2-(3-methoxy-phenyl)-ethyl]-propionamide | 29 | 468 | 96 | 0 05 | 1337 |
| 292 | 2-[(Benzofuran-2-ylmethyl)-amino]-3-(1H-indol-3-yl)-N-(2-trifluoromethyl-benzyl)-propion-amide | 3 | 492 | 90 | 0 06 | 1126 |
| 293 | 2-[(Benzofuran-2-ylmethyl)-amino]-N-[2-(3-fluoro-phenyl)-ethyl]-3-(1H-indol-3-yl)-propionamide | 33 | 456 | 96 | 0 05 | 55 |
| 294 | 2-[(Benzofuran-2-ylmethyl)-amino]-N-(1-cyclohexyl-ethyl)-3-(1H-indol-3-yl)-propionamide | 15 | 444 | 86 | 0 06 | 58 |
| 295 | 2-[(Benzofuran-2-ylmethyl)-amino]-3-(1H-indol-3-yl)-N-(1-methoxymethyl-2-phenyl-ethyl)-propionamide | 34 | 482 | 99 | 0 06 | 3531 |
| 296 | 2-[(Benzofuran-2-ylmethyl)-amino]-N-(2-benzyl-sulfanyl-ethyl)-3-(1H-indol-3-yl)-propionamide | 16 | 484 | 98 | 0 06 | 1338 |
| 297 | 2-[(Benzofuran-2-ylmethyl)-amino]-3-(1H-indol-3-yl)-N-[2-(1H-indol-3-yl)-1-methyl-ethyl]-propionamide | 36 | 491 | 100 | 0 05 | 3612 |
| 298 | 2-[(Benzofuran-2-ylmethyl)-amino]-N-(2-chloro-benzyl)-3-(1H-indol-3-yl)-propionamide | 22 | 458 | 99 | 0 06 | 221 |
| 299 | 2-[(Benzofuran-2-ylmethyl)-amino]-N-(2-hydroxy-1-phenyl-ethyl)-3-(1H-indol-3-yl)-propionamide | 28 | 454 | 93 | 0 05 | 4 |
| 300 | 2-[(Benzofuran-2-ylmethyl)-amino]-3-(1H-indol-3-yl)-N-(2-p-tolyl-ethyl)-propionamide | 10 | 452 | 98 | 0 06 | 256 |
| 301 | 2-[(Benzofuran-2-ylmethyl)-amino]-N-(2,4-difluoro-benzyl)-3-(1H-indol-3-yl)-propion-amide | 12 | 460 | 98 | 0 06 | 53 |
| 302 | 2-[(Benzofuran-2-ylmethyl)-amino]-N-(2-bromo-benzyl)-3-(1H-indol-3-yl)-propionamide | 25 | 503 | 98 | 0 06 | 174 |
| 303 | 2-[(Benzofuran-2-ylmethyl)-amino]-N-(3-fluoro-5-tri-fluoromethyl-benzyl)-3-(1H-indol-3-yl)-propionamide | 7 | 510 | 88 | 0 06 | 17 |
| 304 | [2-[(Benzofuran-2-ylmethyl)-amino]-3-(1H-indol-3-yl)-propionylamino]-phenyl-acetic acid methyl ester | 36 | 482 | 100 | 0 06 | 43 |
| 305 | 2-[(Benzofuran-2-ylmethyl)-amino]-3-(1H-indol-3-yl)-N-(2-phenoxy-ethyl)-propionamide | 30 | 454 | 99 | 0 06 | 400 |
| 306 | N-(4-Amino-benzyl)-2-[(benzo-furan-2-ylmethyl)-amino]-3-(1H-indol-3-yl)-propion-amide | 32 | 439 | 99 | 0 04 | 639 |
| 307 | 2-[(Benzofuran-2-ylmethyl)-amino]-3-(1H-indol-3-yl)-N-(1-methyl-3-phenyl-propyl)-propion-amide | 36 | 466 | 99 | 0 06 | 392 |
| 308 | 2-[(Benzofuran-2-ylmethyl)-amino]-N-(3-hydroxy-benzyl)-3-(1H-indol-3-yl)-propionamide | 6 | 440 | 94 | 0 05 | 731 |

TABLE 4

Examples 309–359

| Ex. | Name | Yield (mg) | Mol. ion | Icms % purity | Icms Rt (min) | IC$_{50}$ (nM) hNK$_1$ |
|---|---|---|---|---|---|---|
| 309 | 3-(1H-Indol-3-yl)-2-methyl-2-[(naphthalen-2-ylmethyl)-amino]-N-(1-phenyl-ethyl)-propionamide | 30, 51 | 462 | 50 | 6, 44 | 169 |
| 310 | 3-(1H-Indol-3-yl)2-methyl-N-(1-phenyl-ethyl)-2-[(pyridin-2-ylmethyl)-amino]-propionamide | 37, 02 | 413 | 83 | 4, 74 | 3325 |
| 311 | 3-(1H-Indol-3-yl)-2-methyl-N-(1-phenyl-ethyl)-2-[(quinolin-2-ylmethyl)-amino]-propionamide | 31, 53 | 463 | 84 | 5, 96 | 88 |
| 312 | 2-[(Furan-3-ylmethyl)-amino]-3-(1H-indol-3-yl)-2-methyl-N-(1-phenyl-ethyl)-propionamide | 28 | 402 | 78 | 4, 9 | 1820 |
| 313 | 3-(1H-Indol-3-yl)-2-methyl-N-(1-phenyl-ethyl)-2-[(pyridin-4-ylmethyl)-amino]-propionamide | 41, 02 | 452 | 8 | 6, 02 | 50 |
| 314 | 2-[(Furan-2-ylmethyl)-amino]-3-(1H-indol-3-yl)-2-methyl-N-(1-phenyl-ethyl)-propionamide | 27, 6 | 402 | 74 | 4, 82 | 141 |
| 315 | 3-(1H-Indol-3-yl)-2-methylN-(1-phenyl-ethyl)-2-[(quinolin-3-ylmethyl)-amino]-propionamide | 3, 13 | 463 | 12 | 3, 78 | 1068 |
| 316 | 2-[(1H-Benzoimidazol-2-ylmethyl)-amino]-3-(1H-indol-3-yl)-2-methyl-N-(1-phenyl-ethyl)-propionamide | 58, 59 | 452 | 16 | 4, 63 | >10,000 |
| 317 | 3-(1H-Indol-3-yl)-2-[(5-methoxy-benzofuran-2-ylmethyl)-amino]-2-methyl-N-(1-phenyl-ethyl)-propionamide | 33, 16 | 482 | 75 | 7, 29 | >10,000 |
| 318 | 3-(1H-Indol-3-yl)-2-[(isoquinolin-4-ylmethyl)-amino]-2-methyl-N-(1-phenyl-ethyl)-propionamide | 8, 84 | 463 | 55 | 3, 28 | 1596 |
| 319 | 3-(1H-Indol-3-yl)-2-[(6-methoxy-benzofuran-2-ylmethyl)-amino]-2-methyl-N-(1-phenyl-ethyl)-propionamide | 5, 15 | 482 | 65 | 7, 22 | 2098 |
| 320 | 3-(1H-Indol-3-yl)-2-methyl-N-(1-phenyl-ethyl)-2-[(pyridin-3-ylmethyl)-amino]-propionamide | 20, 2 | 413 | 72 | 2, 51 | 5972 |
| 321 | 2-{2-[2-(1,3-Dioxo-1,3-dihydro-isoindol-2-yl)-acetylamino]-ethylamino}-3-(1H-indol-3-yl)-2-methyl-N-(1-phenyl-ethyl)-propionamide | 20, 67 | 552 | 96 | 0 05 | 3040 |
| 322 | 2-(3-Furan-2-yl-allylamino)-3-(1H-indol-3-yl)-2-methyl-N-(1-phenyl-ethyl)-propionamide | 2, 88 | 428 | 47 | 0 05 | 91 |
| 323 | 3-(1H-Indol-3-yl)-2-methyl-N-(1-phenyl-ethyl)-2-[2-(pyridin-2-ylmethoxy)-benzylamino]-propionamide | 28, 74 | 519 | 69 | 0 05 | 3183 |
| 324 | 3-(1H-Indol-3-yl)-2-methyl-N-(1-phenyl-ethyl)-2-[2-(pyridin-3-ylmethoxy)-benzylamino]-propionamide | 32, 96 | 519 | 88 | 0 04 | 2971 |
| 325 | 3-(1H-Indol-3-yl)-2-methyl-N-(1-phenyl-ethyl)-2-[(5-styryl-furan-2-ylmethyl)-amino]-propionamide | 42, 66 | 504 | 77 | 0 06 | 72 |
| 326 | 2-(4-Chloro-3-methylsulfamoyl-benzylamino)-3-(1H-indol-3-yl)-2-methyl-N-(1-phenyl-ethyl)-propionamide | 8, 05 | 539 | 83 | 0 05 | 4827 |
| 327 | 5-(4-{[2-(1H-Indol-3-yl)-1-methyl-1-(1-phenyl-ethylcarbamoyl)-ethylamino]-methyl}-phenoxy)-2,2-dimethyl-pentanoic acid | 7, 02 | 556 | 92 | 0 05 | >10,000 |
| 328 | 3-(1H-Indol-3-yl)-2-methyl-2-{[4-(4-methyl-pent-2-enyl)-cyclohex-3-enylmethyl]-amino}-N-(1-phenyl-ethyl)-propionamide | 17, 49 | 498 | 86 | 0 07 | >10,000 |
| 329 | (2-{[2-(1H-Indol-3-yl)-1-methyl-1-(1-phenyl-ethylcarbamoyl)-ethylamino]-methyl}-phenyl)-carbamic acid ethyl ester | 16, 92 | 499 | 95 | 0 05 | 4188 |

TABLE 4-continued

Examples 309–359

| Ex. | Name | Yield (mg) | Mol. ion | Icms % purity | Icms Rt (min) | IC$_{50}$ (nM) hNK$_1$ |
|---|---|---|---|---|---|---|
| 330 | 2-(4-Chloro-2-methylsulfamoyl-benzylamino)-3-(1H-indol-3-yl)-2-methyl-N-(1-phenyl-ethyl)-propionamide | 7, 56 | 539 | 89 | 0 05 | 1100 |
| 331 | 2-[4-(2-Dimethylamino-ethoxy)-benzylamino]-3-(1H-indol-3-yl)-2-methyl-N-(1-phenyl-ethyl)-propionamide | 24, 9 | 499 | 65 | 0 03 | >10,000 |
| 332 | 2-(2,3-Diphenyl-propylamino)-3-(1H-indol-3-yl)-2-methyl-N-(1-phenyl-ethyl)-propionamide | 10, 84 | 516 | 98 | 0 06 | 4944 |
| 333 | 3-(1H-Indol-3-yl)-2methyl-N-(1-phenyl-ethyl)-2-[(1-phenyl-1H-indol-2-ylmethyl)-amino]-propionamide | 16, 98 | 516 | 98 | 0 06 | 3606 |
| 334 | 3-(1H-Indol-3-yl)-2-methyl-N-(1-phenyl-ethyl)-2-[4-(4-phenyl-piperidin-1-yl)-benzylamino]-propionamide | 19, 88 | 527 | 74 | 0 06 | >10,000 |
| 335 | 3-(1H-Indol-3-yl)-2-methyl-N-(1-phenyl-ethyl)-2-[4-(2-pyrrolidin-1-yl-ethoxy)-benzylamino]-propionamide | 38, 16 | 571 | 65 | 0 06 | >10,000 |
| 336 | 2-(4-Chloro-3-sulfamoyl-benzylamino)-3-(1H-indol-3-yl)-2-methyl-N-(1-phenyl-ethyl)-propionamide | 5, 2 | 525 | 79 | 0 03 | 4229 |
| 337 | 4-{[2-(1H-Indol-3-yl)-1-methyl-1-(1-phenyl-ethylcarbamoyl)-ethylamino]-methyl}-benzoic acid methyl ester | 20, 24 | 525 | 81 | 0 04 | 1920 |
| 338 | 2-(2,3-Diphenyl-allylamino)-3-(1H-indol-3-yl)-2-methyl-N-(1-phenyl-ethyl)-propionamide | 20, 13 | 470 | 99 | 0 05 | >10,000 |
| 339 | 2-(3-Benzo[1,3]dioxol-5-yl-allylamino)-3-(1H-indol-3-yl)-2-methyl-N-(1-phenyl-ethyl)-propionamide | 24, 74 | 514 | 54 | 0 06 | 343 |
| 340 | 2-[3-(4-Benzyloxy-phenyl)-allylamino]-3-(1H-indol-3-yl)-2-methyl-N-(1-phenyl-ethyl)-propionamide | 24, 64 | 482 | 72 | 0 05 | 4912 |
| 341 | 2-(4-Benzyloxy-benzylamino)-3-(1H-indol-3-yl)-2-methyl-N-(1-phenyl-ethyl)-propionamide | 32, 02 | 544 | 62 | 0 06 | >10,000 |
| 342 | Toluene-4-sulfonic acid 3-{[2-(1H-indol-3-yl)-1-methyl-1-(1-phenyl-ethylcarbamoyl)-ethylamino]-methyl}-phenyl ester | 20, 65 | 518 | 96 | 0 06 | 5091 |
| 343 | 2-[(Benzofuran-2-ylmethyl)-amino]-3-(1H-indol-3-yl)-2-methyl-N-(1-phenyl-ethyl)-propionamide | 23, 9 | 582 | 93 | 0 06 | 13 |
| 344 | 2-(3-Benzyloxy-benzylamino)-3-(1H-indol-3-yl)-2-methyl-N-(1-phenyl-ethyl)-propionamide | 33, 15 | 518 | 89 | 0 06 | 185 |
| 345 | 3-(1H-Indol-3-yl)-2-methyl-2-(4-methylsulfanyl-benzylamino)-N-(1-phenyl-ethyl)-propionamide | 31, 61 | 458 | 90 | 0 06 | 609 |
| 346 | 2-[(Anthracen-9-ylmethyl)-amino]-3-(1H-indol-3-yl)-2-methyl-N-(1-phenyl-ethyl)-propionamide | 17, 46 | 512 | 73 | 0 07 | >10,000 |
| 347 | 3-(1H-Indol-3-yl)-2-methyl-2-(4-phenoxy-benzylamino)-N-(1-phenyl-ethyl)-propionamide | 36, 52 | 504 | 95 | 0 06 | 3382 |
| 348 | 2-[(Biphenyl-4-ylmethyl)-amino]-3-(1H-indol-3-yl)-2-methyl-N-(1-phenyl-ethyl)-propionamide | 30, 82 | 488 | 93 | 0 06 | 5562 |
| 349 | 2-[(Benzo[1,3]dioxol-5-ylmethyl)-amino]-3-(1H-indol-3-yl)-2-methyl-N-(1-phenyl-ethyl)-propionamide | 33, 19 | 456 | 94 | 0 06 | 356 |
| 350 | 2-[2-(4-Chloro-phenylsulfanyl)-benzylamino]-3-(1H-indol-3-yl)-2-methyl-N-(1-phenyl-ethyl)-propionamide | 21, 92 | 554 | 90 | 0 07 | >10,000 |

TABLE 4-continued

Examples 309–359

| Ex. | Name | Yield (mg) | Mol. ion | Icms % purity | Icms Rt (min) | IC$_{50}$ (nM) hNK$_1$ |
|---|---|---|---|---|---|---|
| 351 | 3-(1H-Indol-3-yl)-2-methyl-N-(1-phenyl-ethyl)-2-(4-styryl-benzylamino)-propionamide | 22, 24 | 514 | 88 | 0 07 | >10,000 |
| 352 | 2-(2,6-Dimethyl-octa-2,6-dienylamino)-3-(1H-indol-3-yl)-2-methyl-N-(1-phenyl-ethyl)-propionamide | 30, 03 | 458 | 44 | 0 07 | 2212 |
| 353 | 3-(1H-Indol-3-yl)-2-methyl-2-{[5-(4-nitro-phenyl)-furan-2-ylmethyl]-amino}-N-(1-phenyl-ethyl)-propionamide | 38, 51 | 523 | 82 | 0 06 | 13 |
| 354 | 2-[(9H-Fluoren-2-ylmethyl)-amino]-3-(1H-indol-3-yl)-2-methyl-N-(1-phenyl-ethyl)-propionamide | 27, 91 | 500 | 92 | 0 06 | 1731 |
| 355 | 3-(1H-Indol-3-yl)-2-[(1H-indol-3-ylmethyl)-amino]-2-methyl-N-(1-phenyl-ethyl)-propionamide | 9, 83 | 451 | 69 | 0 06 | 1047 |
| 356 | 3-(1H-Indol-3-yl)-2-methyl-2-(2-pentyl-3-phenyl-allylamino)-N-(1-phenyl-ethyl)-propionamide | 33, 02 | 508 | 86 | 0 07 | >10,000 |
| 357 | 3-(1H-Indol-3-yl)-2-methyl-N-(1-phenyl-ethyl)-2-[(thiophen-2-ylmethyl)-amino]-propionamide | 18, 91 | 418 | 97 | 0 05 | 548 |
| 358 | 3-(1H-Indol-3-yl)-2-methyl-N-(1-phenyl-ethyl)-2-[(thiophen-3-ylmethyl)-amino]-propionamide | 18, 79 | 418 | 99 | 0 05 | 598 |
| 359 | 3-(1H-Indol-3-yl)-2-methyl-N-(1-phenyl-ethyl)-2-[(pyridin-4-ylmethyl)-amino]-propionamide | 7, 47 | 413 | 79 | 0 04 | 3712 |

TABLE 5

Examples 360–405

| Ex. | Name | Yield (mg) | Mol. ion | Icms % purity | Icms Rt (min) | IC$_{50}$ (nM) hNK$_1$ |
|---|---|---|---|---|---|---|
| 360 | 2-(3-Furan-2-yl-allylamino)-3-(1H-indo-3-yl)-N-(1-phenyl-ethyl) propionamide | 12, 16 | 414 | 59 | 0 06 | >10,000 |
| 361 | 3-(1H-Indol-3-yl)-N-(1-phenyl-ethyl)-2-[2-(pyridin-3-ylmethoxy)-benzyl-amino]-propionamide | 14, 01 | 505 | 79 | 0 04 | 729 |
| 362 | 3-(1H-Indol-3-yl)-N-(1-phenyl-ethyl)-2-[(5-styryl-furan-2-ylmethyl)-amino]-propionamide | 39, 92 | 490 | 36 | 0 08 | >10,000 |
| 363 | 2-(4-Chloro-3-methylsulfamoyl-benzylamino)-3-(1H-indol-3-yl)-N-(1-phenyl-ethyl)-propionamide | 18, 8 | 526 | 86 | 0 06 | 490 |
| 364 | 5-(4-{[2-(1H-Indol-3-yl)-1-(1-phenyl-ethylcarbamoyl)-ethylamino]-methyl}-phenoxy)-2,2-dimethyl-pentanoic acid | 12, 49 | 543 | 79 | 0 07 | 1247 |
| 365 | 2-{[4-(4-Hydroxy-4-methyl-pentyl)-cyclohex-3-enyl-methyl]-amino}-3-(1H-indol-3-yl)-N-(1-phenyl-ethyl)-propionamide | 31, 21 | 503 | 42 | 0 07 | 5278 |
| 366 | 3-(1H-Indol-3-yl)-2-{[4-(4-methyl-pent-2-enyl)-cyclohex-3-enylmethyl)-amino}-N-(1-phenyl-ethyl)-propionamide | 38, 13 | 484 | 65 | 0 09 | 4046 |
| 367 | (2-{[2-(1H-Indol-3-yl)-1-(1-phenyl-ethylcarbamoyl)-ethylamino]-methyl}-phenyl)-carbamic acid ethyl ester | 4, 86 | 485 | 82 | 0 07 | 236 |
| 368 | 2-(2-Chloro-4-morpholin-4-yl-benzylamino)-3-(1H-indol-3-yl)-N-(1-phenyl-ethyl)-propionamide | 14, 38 | 518 | 84 | 0 07 | 2239 |
| 369 | 2-(4-Chloro-2-methylsulfamoyl-benzylamino)-3-(1H-indol-3-yl)-N-(1-phenyl-ethyl)-propionamide | 53, 07 | 526 | 83 | 0 06 | 450 |

TABLE 5-continued

Examples 360–405

| Ex. | | Yield (mg) | Mol. ion | Lcms % purity | Lcms Rt (min) | IC$_{50}$ (nM) hNK$_1$ |
|---|---|---|---|---|---|---|
| 370 | 2-(2,3-Diphenyl-propylamino)-3-(1H-indol-3-yl)-N-(1-phenyl-ethyl)-propionamide | 11, 18 | 502 | 73 | 0 08 | 534 |
| 371 | 3-(1H-Indol-3-yl)-2-[(4-oxo-4H-chromen-3-yl-methyl)-amino]-N-(1-phenyl-ethyl)-propionamide | 16, 18 | 466 | 66 | 0 07 | >10,000 |
| 372 | 3-(1H-Indol-3-yl)-2-[(1-oxo-1,2,3,9-tetrahydro-4-thia-9-aza-fluoren-2-yl-methyl)-amino]-N-(1-phenyl-ethyl)-propionamide | 9 | 523 | 26 | 0 08 | >10,000 |
| 373 | 3-(1H-Indol-3-yl)-2-[(5-methyl-4-oxo-6-phenyl-4H-pyran-3-ylmethyl)-amino]-N-(1-phenyl-ethyl)-propionamide | 17, 38 | 506 | 2 | 0 07 | 507 |
| 374 | 4-{[2-(1H-Indol-3-yl)-1-(1-phenyl-ethylcarbamoyl)-ethylamino]-methyl}-benzoic acid methyl ester | 33, 82 | 456 | 95 | 0 06 | 1914 |
| 375 | 3-(1H-Indol-3-yl)-N-(1-phenyl-ethyl)-2-[(2-propyl-5-pyrrol-1-yl-3H-imidazol-4-yl-methyl)-amino]-propionamide | 28, 55 | 495 | 76 | 0 05 | 165 |
| 376 | 2-(2,3-Diphenyl-allylamino)-3-(1H-indol-3-yl)-N-(1-phenyl-ethyl)-propionamide | 14, 27 | 500 | 76 | 0 08 | >10,000 |
| 377 | 2-(3-Benzo[1,3]dioxol-5-yl-allyl-amino)-3-(1H-indol-3-yl)-N-(1-phenyl-ethyl)-propionamide | 14, 52 | 468 | 57 | 0 07 | 593 |
| 378 | 2-[3-(4-Benzyloxy-phenyl)-allylamino]-3-(1H-indol-3-yl)-N-(1-phenyl-ethyl)-propionamide | 8, 68 | 530 | 64 | 0 09 | 932 |
| 379 | 2-(4-Benzyloxy-benzylamino)-3-(1H-indol-3-yl)-N-(1-phenyl-ethyl)-propionamide | 15, 05 | 504 | 80 | 0 08 | 587 |
| 380 | 3-(1H-Indol-3-yl)-2-(3-naphthalen-1-yl-propylamino)-N-(1-phenyl-ethyl)-propionamide | 11, 18 | 476 | 46 | 0 08 | 500 |
| 381 | Toluene-4-sulfonic acid 3-{[2-(1H-indol-3-yl)-1-(1-phenyl-ethylcarbamoyl)-ethylamino]-methyl}-phenyl ester | 24, 84 | 568 | 92 | 0 08 | >10,000 |
| 382 | 2-(3-Benzyloxy-benzylamino)-3-(1H-indol-3-yl)-N-(1-phenyl-ethyl)-propionamide | 44, 62 | 504 | 91 | 0 08 | >10,000 |
| 383 | 3-(1H-Indol-3-yl)-2-(4-methylsulfanyl-benzylamino)-N-(1-phenyl-ethyl)-propionamide | 39, 33 | 444 | 69 | 0 07 | 252 |
| 384 | 3-(1H-Indol-3-yl)-2-(4-phenoxy-benzyl-amino)-N-(1-phenyl-ethyl)-propionamide | 32, 52 | 490 | 83 | 0 08 | 2350 |
| 385 | 2-[(Biphenyl-4-yl-methyl)-amino]-3-(1H-indol-3-yl)-N-(1-phenyl-ethyl)-propionamide | 24, 28 | 474 | 90 | 0 08 | 1463 |
| 386 | 2-[(Benzo[1,3]dioxol-5-ylmethyl)-amino]-3-(1H-indol-3-yl)-N-(1-phenyl-ethyl)-propionamide | 41, 91 | 442 | 78 | 0 06 | 240 |
| 387 | 2-[2-(4-Chloro-phenylsulfanyl)-benzylamino]-3-(1H-indol-3-yl)-N-(1-phenyl-ethyl)-propionamide | 48, 88 | 541 | 96 | 0 09 | 201 |
| 338 | 3-(3H-Indol-3-yl)-N-(1-phenyl-ethyl)-2-(4-styryl-benzyl-amino)-propion-amide | 12, 14 | 500 | 66 | 0 09 | >10,000 |
| 389 | 2-(2,6-Dimethyl-octa-2,6-dienyl-amino)-3-(1H-indol-3-yl)-N-(1-phenyl-ethyl)-propionamide | 50, 41 | 444 | 5 | 0 08 | 2573 |
| 390 | 3-(1H-Indol-3-yl)-2-{[5-(4-nitro-phenyl)-furan-2-yl-methyl]-amino}-N-(1-phenyl-ethyl)-propionamide | 7, 86 | 509 | 44 | 0 07 | 50 |
| 391 | 2-[(9H-Fluoren-2-ylmethyl)-amino]-3-(1H-indol-3-yl)-N-(1-phenyl-ethyl)-propionamide | 37, 84 | 486 | 85 | 0 08 | 846 |
| 392 | 2-[(2,5-Dimethyl-1-phenyl-1H-pyrrol-3-ylmethyl)-amino]-3-(1H-indol-3-yl)-N-(1-phenyl-ethyl)-propionamide | 5, 27 | 491 | 3 | 0 08 | >10,000 |
| 393 | 3-(1H-Indol-3-yl)-N-(1-phenyl-ethyl)-2-[(pyridin-3-yl-methyl)-amino]-propionamide | 03 2 | 399 | 71 | 0 04 | 802 |
| 394 | 3-(1H-Indol-3-yl)-2-[(naphthalen-2-yl-methyl)-amino]-N-(1-phenyl-ethyl)-propionamide | 03 7 | 448 | 88 | 0 06 | 158 |
| 395 | 3-(1H-Indol-3-yl)-N-(1-phenyl-ethyl)-2-[(pyridin-2-yl-methyl)-amino]-propionamide | 02 9 | 399 | 74 | 0 05 | >10,000 |
| 396 | 3-(1H-Indol-3-yl)-N-(1-phenyl-ethyl)-2-[(thiophen-2-yl-methyl)-amino]-propionamide | 04 3 | 404 | 98 | 0 05 | 1073 |

TABLE 5-continued

Examples 360–405

| Ex. | | Yield (mg) | Mol. ion | Icms % purity | Icms Rt (min) | IC$_{50}$ (nM) hNK$_1$ |
|---|---|---|---|---|---|---|
| 397 | 2-(3,4-Dimethoxy-benzylamino)-3-(1H-indol-3-yl)-N-(1-phenyl-ethyl)-propionamide | 03 3 | 458 | 65 | 0 05 | >10,000 |
| 398 | 2-(3,5-Bis-trifluoro-methyl-benzyl-amino)-3-(1H-indol-3-yl)-N-(1-phenyl-ethyl)-propionamide | 04 3 | 534 | 94 | 0 07 | >10,000 |
| 399 | 2-(3,5-Difluoro-benzylamino)-3-(1H-indol-3-yl)-N-(1-phenyl-ethyl)-propionamide | 03 5 | 434 | 92 | 0 06 | 140 |
| 400 | 2-(3-Chloro-benzyl-amino)-3-(1H-indol-3-yl)-N-(1-phenyl-ethyl)-propionamide | 03 4 | 432 | 86 | 0 06 | 13 |
| 401 | 2-(3-Fluoro-benzyl-amino)-3-(1H-indol-3-yl)-N-(1-phenyl-ethyl)-propionamide | 03 4 | 416 | 87 | 0 06 | 39 |
| 402 | 2-[(Furan-3-yl-methyl)-amino]-3-(1H-indol-3-yl)-N-(1-phenyl-ethyl)-propionamide | 03 0 | 388 | 84 | 0 05 | 881 |
| 403 | 3-(1H-Indol-3-yl)-N-(1-phenyl-ethyl)-2-(3-phenyl-propyl-amino)-propion-amide | 0 07 | 426 | 85 | 0 06 | 3907 |
| 404 | 3-(1H-Indol-3-yl)-N-(1-phenyl-ethyl)-2-[(thiophen-3-yl-methyl)-amino]-propionamide | 03 2 | 404 | 81 | 0 05 | 2390 |
| 405 | 2-[(Furan-2-yl-methyl)-amino]-3-(1H-indol-3-yl)-N-(1-phenyl-ethyl)-propionamide | 03 2 | 388 | 86 | 0 06 | 429 |

As noted above, the compounds of formula I will be best utilized in the form of pharmaceutical formulations. The following examples further illustrate specific formulations that are provided by the invention.

EXAMPLE 406

| Ingredient | Amount |
|---|---|
| 3-[(benzofuran-2-ylmethyl)-amino]-3-(1H-indol-3-yl)-2-methyl-N-(1-phenyl-ethyl)-propionamide,[(R-(R*,S*)] | 50 mg |
| potato starch | 100 mg |
| talc | 50 mg |
| magnesium carbonate | 20 mg |
| dextrose | 20 mg |
| | 240 mg |

The above ingredients are blended to uniformity and pressed into a tablet. Such tablets are administered to human subjects from one to four times a day for treatment of pain, depression and schizophrenia.

EXAMPLE 407

| Ingredient | Amount |
|---|---|
| The compound of Example 5 | 200 mg |
| Corn starch | 100 mg |
| Sodium benzoate | 10 mg |
| talc | 50 mg |
| | 360 mg |

The ingredients are blended to uniformity and encapsulated into gelatin telescoping capsules. The capsules are administered to a human at the rate of one to three each day for treatment of rheumatoid arthritis, atheroclerosis, aberrant neovascularization, and for the inhibition of tumor cell growth.

We claim:

1. A compound of Formula I

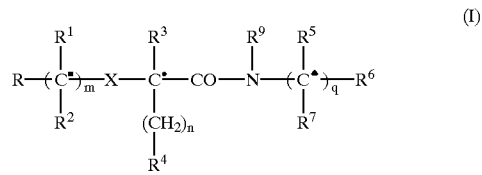

(I)

and the pharmaceutically acceptable salt thereof, wherein ■, ●, ▲, indicate all stereoisomers, R is:
  furyl
  benzofuryl, or
    benzoxazolyl, wherein each of the foregoing is unsubstitute, mono-, di- or trisubstituted by
      alkyl,
      hydroxy,
      alkoxy,
      halogen,
      —CF$_3$,
      carboxy,
      sulfonamide, or
      nitro;
$R^1$ and $R^2$ are each independently H or $C_1$–$C_4$ alkyl;
m is an integer from 0 to 3;
X is $NR^8$ where $R^8$ is H or $C_1$–$C_4$ alkyl;
$R^3$ is hydrogen or $C_1$–$C_4$ alkyl;
n is an integer from 1 to 2;
$R^4$ is indolyl, wherein said groups are substituted, mono, di- or trisubstituted by alkyl, hydroxy or formyl;
$R^9$ is hydrogen or $C_1$–$C_4$ alkyl;
$R^5$ and $R^7$ are each independently hydrogen or $(CH_2)_p R^{10}$ where:
  p is an integer of 1 to 3, and
  $R^{10}$ is H, $CH_3$, CN, OH, $OCH_3$, $CO_2CH_3$, $NH_2$, $NHCH_3$, or $N(CH_3)_2$;
q is integer of 0 to 4;
$R^6$ is phenyl,
  wherein the foregoing is unsubstituted, mono-, di- or trisubstituted by
    alkyl,
    hydroxy,
    alkoxy,
    halogen, CF$_3$,
NO$_2$,
N(CH$_3$)$_2$,
OCF$_3$,
SONH$_2$,
NH$_2$,
CONH$_2$,
CO$_2$CH$_3$, or
CO$_2$H, and R$^5$ and R$^6$ when joined by a bond, can form a ring.

2. A compound of claim 1 wherein R is selected from:
furyl,
benzofuryl,
benzoxazolyl, wherein each of the foregoing is unsubstituted, mono-, di- or trisubstituted by alkyl, hydroxy, alkoxy, halogen, or CF$_3$;
m is an integer from 1 to 3;
R$^6$ is phenyl,
  wherein the foregoing is a unsubstituted, mono-, di- or trisubstituted by
    alkyl,
    hydroxy,
    alkoxy,
    halogen,
    CF$_3$,
    NO$_2$,
    N(CH$_3$)$_2$,
    OCF$_3$,
    SON$_2$,
    NH$_2$,
    CONH$_2$,
    CO$_2$CH$_3$, or
    CO$_2$H,
  cycloalkyl of from 5 to 6 carbons or heterocycloalkyl, with up to one or two substituents selected from OH,
    CO$_2$H,
    N(CH$_3$)$_2$,
    NHCH$_3$ and
    CH$_3$; and R$^5$ and R$^6$ when joined by a bond can form a ring.

3. A compound according to claim 2 wherein R$^1$ and R$^2$ each are hydrogen.

4. A compound according to claim 3 wherein X is NR$^8$.

5. A compound according to claim 4, wherein
R is furyl,
  benzofuryl, or
  benzoxazolyl, where each of the foregoing is unsubstituted, mono-, di- or trisubstituted by alkyl, hydroxy, alkoxy, halogen, or —CF$_3$;
R$^1$ and R$^2$ are each H;
m is a integer from 1 to 3;
X is NR$^8$, where R$^8$ is H or methyl;
R$^9$ is hydrogen or alkyl of 1 to 3 carbon atoms;
R$^6$ is phenyl
  where the foregoing is unsubstituted, mono-, di- or trisubstituted by
    alkyl,
    hydroxy,
    alkoxy,
    halogen,
    CF$_3$,
    NO$_2$, or
    N(CH$_3$)$_2$;
  cyclohexyl or heterocycloalkyl, with up to one or two substituents selected from
    OH,
    CO$_2$H,
    N(CH$_3$)$_2$,
    NHCH$_3$ and
    CH$_3$; and R$^5$ and R$^6$, when joined by a bond, can form a ring.

6. A compound of the Formula II

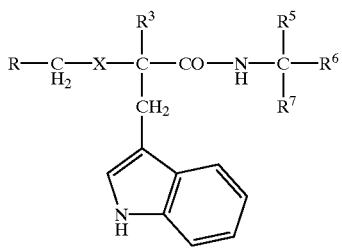

(II)

wherein:

R is
  benzofuryl, or
  benzoxazolyl;
R$^3$ is hydrogen or methyl;
X is NH or NHCONH;
R$^5$ and R$^7$ independently are hydrogen or CH$_2$R$^{10}$, where R$^{10}$ is H, CH$_3$ or OH;
R$^6$ is phenyl;

and the pharmaceutically acceptable salts thereof.

7. A compound of claim 6 selected from:

2-[(Benzofuran-2-ylmethyl)-amino]-3-(1H-indol-3-yl)-2-methyl-N-(1-phenyl-ethyl)-propionamide, [R-(R*,S*)];

2-[Benzofuran-2-ylmethyl)-amino]-3-(1H-indol-3-yl)-2-methyl-N-[1-(4-nitro-phenyl)-ethyl]-propionamide, [R-(R*,R*)];

2-(Benzofuran-2-ylmethyl)-amino]-N-(2-hydroxy-1-phenyl-ethyl)-3-(1H-indol-3-yl)-2-methyl-propionamide, [R-(R*,R*)];

[R-(R*,S*)]2-[(Benzofuran-2-ylmethyl)-amino]-3-(1H-indol-3-yl)-2methyl-N-(1-p-tolyl-ethyl)-propionamide;

2-[(Benzofuran-2-ylmethyl)-amino]-3-(1H-indol-3-yl)-N-(1-p-tolyl-ethyl)-propionamide, [R-(R*,S*)];

2-[(Benzofuran-2-ylmethyl)-amino]-3-(1H-indol-3-yl)-N-(1-phenyl-ethyl)-propionamide, [R-(R*,S*)];

2-[(Benzoxazol-2-ylmethyl)-amino]-3-(1H-indol-3-yl)-N-(1-phenyl-ethyl)-propionamide;

2-(2-Benzofuran-2-yl-ethylamino)-3-(1H-indol-3-yl)-N-(1-phenyl-ethyl)-propionamide, [R-(R*,S*)]; and 2-(3-Benzofuran-2-ylmethyl-ureido)-3-(1H-indol-3-yl)-2-methyl-N-(1-phenyl-ethyl)-propionamide, [R-(R*,S*)].

8. A pharmaceutical formulation comprising a compound of claim 1 admixed with a pharmaceutical acceptable diluent, carrier or excipient.

9. A formulation according to claim 8 employing a compound of Formula II

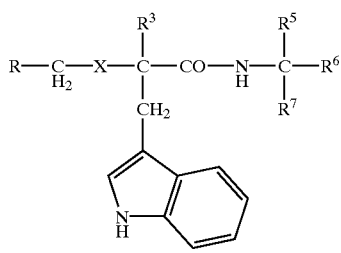

(II)

wherein:
R is
  benzofuryl, or
  benzoxazolyl;
$R^3$ is hydrogen or methyl;
X is NH or NHCONH;
$R^5$ and $R^7$ independently are hydrogen or $CH_2R^{10}$, where $R^{10}$ is H, $CH_3$ or OH;
$R^6$ is phenyl;
and the pharmaceutically acceptable salts thereof.

10. A formulation according to claim 9 employing a compound selected from:

2-[(Benzofuran-2-ylmethyl)-amino]-3-(1H-indol-3-yl)-2-methyl-N-(1-phenyl-ethyl)-propionamide, [R-(R*,S*)];

2-[(Benzofuran-2-ylmethyl)-amino]-3-(1H-indol-3-yl)-2-methyl-N-[1-(4-nitro-phenyl)-ethyl]-propionamide, [R-(R*,R*)];

2-[(Benzofuran-2-ylmethyl)-amino]-N-(2-hydroxy-1-phenyl-ethyl)-3-(1H-indol-3-yl)-2-methyl-propionamide, [R-(R*,R*)];

[R-(R*,S*)]2-[(Benzofuran-2-ylmethyl)-amino]-3-(1H-indol-3-yl)-2-methyl-N-(1-p-tolyl-ethyl)-propionamide;

2-[(Benzofuran-2-ylmethyl)-amino]-3-(1H-indol-3-yl)-N-(1-p-tolyl-ethyl)-propionamide, [R-(R*,S*)];

2-[(Benzofuran-2-ylmethyl)-amino]-3-(1H-indol-3-yl)-N-(1-phenyl-ethyl)-propionamide, [R-(R*,S*)];

2-[(Benzooxazol-2-ylmethyl)-amino]-3-(1H-indol-3-yl)-N-(1-phenyl-ethyl)propionamide;

2-(2Benzofuran-2-yl-ethylamino)-3-(1H-indol-3yl)-N-(1-phenyl-ethyl)-propionamide, [R-(R*,S*)] and 2-(3-Benzofuran-2-ylmethyl-ureido)-3-(1H-indol-3-yl)-2-methyl-N-(1-phenyl-ethyl)-propionamide, [R-(R*,S*)].

11. A method for antagonizing the $NK_1$ receptor in a mammal comprising administering a compound of claim 1.

12. A method for treating a CNS disorder in a mammal in need of treatment comprising administering an effective amount of a compound of claim 1.

13. A method according to claim 12 wherein the CNS disorder is selected from pain, anxiety, depression or schizophrenia.

14. A method according to claim 12 wherein the CNS disorder is selected from neuralgia, stress, sexual dysfunction, bipolar disorders, movement disorders, cognitive disorders, obesity, and addiction disorders.

15. A method for treating an allergic or inflammatory disorder in a mammal in need of treatment comprising administering an effective amount of a compound of claim 1.

16. A method according to claim 15 wherein the allergic or inflammatory disorder is selected from arthritis, asthma, bronchitis, psoriasis, eczema, rhinitis, colitis or Crohn's disease.

17. A method for treating a neuropathological disorder in a mammal in need of treatment comprising administering an effective amount of a compound of claim 1.

18. A method according to claim 17 wherein the neuropathological disorder is selected from scleroderma or emesis.

* * * * *

UNITED STATES PATENT AND TRADEMARK OFFICE
CERTIFICATE OF CORRECTION

PATENT NO.    : 6,472,418 B1
DATED         : October 29, 2002
INVENTOR(S)   : Creswell et al.

It is certified that error appears in the above-identified patent and that said Letters Patent is hereby corrected as shown below:

Column 80,
Line 36, "unsubstitute," should read -- unsubstituted, --.
Line 51, "substituted" should read -- unsubstituted --.

Column 81,
Line 30, "SON2" should read -- SONH2 --.

Column 82,
Line 50, "indol-3-yl)-2methyl-" should read -- indol-3-yl)-2-methyl- --.
Line 55, "2-[(Benzoxazol-" should read -- 2-[(Benzooxazol- --.
Line 64, "pharmaceutical" should read -- pharmaceutically --.

Column 84,
Line 5, "2-(2Benzofuran-2-yl-ethylamino)-3-(1H-indol-3yl)-N-(1-" should read
-- 2-(2-Benzofuran-2-yl-ethylamino)-3-(1H-indol-3yl)-N-(1- --.

Signed and Sealed this

Sixth Day of May, 2003

JAMES E. ROGAN
*Director of the United States Patent and Trademark Office*